US012577233B2

(12) United States Patent
Gagnon et al.

(10) Patent No.: US 12,577,233 B2
(45) Date of Patent: Mar. 17, 2026

(54) SOLID FORMS OF APOL1 INHIBITOR AND METHODS OF USING SAME

(71) Applicant: VERTEX PHARMACEUTICALS INCORPORATED, Boston, MA (US)

(72) Inventors: Kevin James Gagnon, Acton, MA (US); Jicong Li, Cambridge, MA (US); Ales Medek, Winchester, MA (US); Jack Raphael Minchom, Somerville, MA (US); Yi Shi, Natick, MA (US); Muna Shrestha, Belmont, MA (US); Faith Witkos, Attleboro, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 616 days.

(21) Appl. No.: 18/001,371

(22) PCT Filed: Jun. 11, 2021

(86) PCT No.: PCT/US2021/036960
§ 371 (c)(1),
(2) Date: Dec. 9, 2022

(87) PCT Pub. No.: WO2021/252863
PCT Pub. Date: Dec. 16, 2021

(65) Prior Publication Data

US 2023/0250087 A1 Aug. 10, 2023

Related U.S. Application Data

(60) Provisional application No. 63/038,271, filed on Jun. 12, 2020.

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC .......................... C07D 403/12; C07B 2200/13
See application file for complete search history.

(56) References Cited

U.S. PATENT DOCUMENTS

| | | | |
|---|---|---|---|
| 5,849,764 | A | 12/1998 | Goulet et al. |
| 6,486,153 | B1 | 11/2002 | Pineiro et al. |

(Continued)

FOREIGN PATENT DOCUMENTS

| | | | |
|---|---|---|---|
| EP | 0924209 | B1 | 6/1999 |
| EP | 0934941 | | 8/1999 |

(Continued)

OTHER PUBLICATIONS

Balasubramanian, M. et al. (1970) "Studies on Conformation: Part X -Addition of Grignard Reagents to 4-Piperidones." *Indian J. Chem.*, vol. 8, May 1, 1970, pp. 420-422.

(Continued)

*Primary Examiner* — Brandon J Fetterolf

(74) *Attorney, Agent, or Firm* — Finnegan, Henderson, Farabow, Garrett & Dunner, LLP

(57) ABSTRACT

The disclosure provides novel solid state forms of Compound I selected from ethanol solvate Form A, ethanol solvate Form B, citric acid cocrystal Form A, and Form B, compositions comprising the same, and methods of making and using the same, including use in treating APOL1 mediated kidney disease. (I).

(Continued)

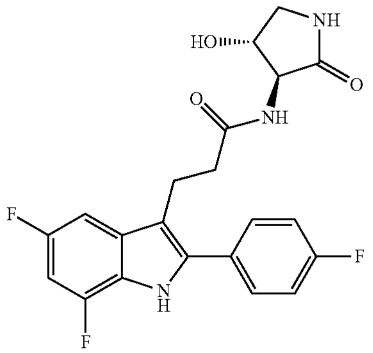

(I)

28 Claims, 15 Drawing Sheets

(56) References Cited

U.S. PATENT DOCUMENTS

| | | | |
|---|---|---|---|
| 6,518,273 | B1 | 2/2003 | Chapman et al. |
| 6,605,633 | B1 | 8/2003 | Paquet et al. |
| 7,674,816 | B2 | 3/2010 | Tao et al. |
| 8,815,903 | B2 | 8/2014 | Tatani et al. |
| 11,618,746 | B2 | 4/2023 | Cao et al. |
| 11,801,234 | B2 | 10/2023 | Mallalieu et al. |
| 11,866,446 | B2 | 1/2024 | Ahn et al. |
| 12,060,346 | B2 | 8/2024 | Cao et al. |
| 12,116,343 | B2 | 10/2024 | Dakin et al. |
| 12,281,102 | B2 | 4/2025 | Dakin et al. |
| 2001/0039286 | A1 | 11/2001 | Dinnell et al. |
| 2004/0006237 | A1 | 1/2004 | Dolitzky et al. |
| 2004/0138287 | A1 | 7/2004 | Barth et al. |
| 2005/0100902 | A1 | 5/2005 | Barth et al. |
| 2008/0153861 | A1 | 6/2008 | Bissantz et al. |
| 2008/0249128 | A1 | 10/2008 | Oberboersch et al. |
| 2010/0317661 | A1 | 12/2010 | Wang et al. |
| 2012/0195902 | A1 | 8/2012 | Friedman et al. |
| 2013/0237532 | A1 | 9/2013 | Kim et al. |
| 2018/0118681 | A1 | 5/2018 | Ross et al. |
| 2020/0377479 | A1* | 12/2020 | Cao et al. |
| 2021/0246121 | A1 | 8/2021 | Lai et al. |
| 2021/0275496 | A1 | 9/2021 | Mallalieu et al. |
| 2022/0106327 | A1 | 4/2022 | Ahn et al. |
| 2022/0340523 | A1 | 10/2022 | Dakin et al. |
| 2023/0011118 | A1 | 1/2023 | Dakin et al. |
| 2023/0014907 | A1 | 1/2023 | Dakin et al. |
| 2023/0119114 | A1 | 4/2023 | Daniel et al. |
| 2023/0201201 | A1 | 6/2023 | Skorecki et al. |
| 2023/0203000 | A1 | 6/2023 | Dakin et al. |
| 2023/0250087 | A1 | 8/2023 | Gagnon et al. |
| 2024/0277661 | A1 | 8/2024 | Mallalieu et al. |
| 2025/0084094 | A1 | 3/2025 | Senter et al. |

FOREIGN PATENT DOCUMENTS

| | | | |
|---|---|---|---|
| EP | 2905278 | A1 | 8/2015 |
| FR | 2315272 | A1 | 1/1977 |
| WO | WO 96-40640 | | 12/1996 |
| WO | WO 1997/021703 | A1 | 6/1997 |
| WO | WO 2000/051984 | A1 | 9/2000 |
| WO | WO 2001/017965 | A2 | 3/2001 |
| WO | WO 2001/038305 | A2 | 5/2001 |
| WO | WO 2002/028831 | A1 | 4/2002 |
| WO | WO 2002/092568 | A1 | 11/2002 |
| WO | WO 2003/004027 | A1 | 1/2003 |
| WO | WO 2003/104180 | A1 | 12/2003 |
| WO | WO 2004/058717 | A1 | 7/2004 |
| WO | WO 2005/021505 | A1 | 3/2005 |
| WO | WO 2005/115983 | | 4/2005 |
| WO | WO 2005/092854 | A1 | 10/2005 |
| WO | WO 2007/061763 | A2 | 5/2007 |
| WO | WO 2008/092231 | A1 | 8/2008 |
| WO | WO 2008/155132 | A1 | 12/2008 |
| WO | WO 2011/060035 | A1 | 11/2010 |
| WO | WO 2011/060217 | A1 | 11/2010 |
| WO | WO 2010/137351 | A1 | 12/2010 |
| WO | WO 2012/025155 | A1 | 3/2012 |
| WO | WO 2012/102255 | A1 | 8/2012 |
| WO | WO 2012/166415 | A1 | 12/2012 |
| WO | WO 2014/085154 | A1 | 6/2014 |
| WO | WO 2015/048301 | A1 | 4/2015 |
| WO | WO 2015/147639 | A1 | 10/2015 |
| WO | WO 2016/055517 | A1 | 4/2016 |
| WO | WO 2016/078770 | A1 | 5/2016 |
| WO | WO 2017/033093 | A1 | 3/2017 |
| WO | WO 2017/137334 | A1 | 8/2017 |
| WO | WO 2019/213148 | A1 | 11/2019 |
| WO | WO 2019/226611 | A1 | 11/2019 |
| WO | WO 2020/131807 | A1 | 6/2020 |
| WO | WO 2020/186220 | A1 | 9/2020 |
| WO | WO 2021/216665 | A1 | 4/2021 |
| WO | WO 2021/127337 | A1 | 6/2021 |
| WO | WO 2021/154997 | A1 | 8/2021 |
| WO | WO 2021/158666 | A1 | 8/2021 |
| WO | WO 2021/178768 | A1 | 9/2021 |
| WO | WO 2021/224927 | A1 | 9/2021 |
| WO | WO 2021/220178 | A1 | 11/2021 |
| WO | WO 2021/252849 | A1 | 12/2021 |
| WO | WO 2021/252859 | A1 | 12/2021 |
| WO | WO 2021/252863 | A1 | 12/2021 |
| WO | WO 2022/047031 | A1 | 3/2022 |
| WO | WO 2023/028237 | A1 | 3/2023 |
| WO | WO 2023/101981 | A1 | 6/2023 |
| WO | WO 2023/154309 | A1 | 8/2023 |
| WO | WO 2023/154310 | A1 | 8/2023 |
| WO | WO 2023/154314 | A1 | 8/2023 |
| WO | WO 2023/154344 | A1 | 8/2023 |

OTHER PUBLICATIONS

Bartolucci, S. et al. (2015), "Iridium-Catalyzed Direct Synthesis of Tryptamine Derivatives from Indoles: Exploiting N-Protected Amino Alcohols as Alkylating Agents," *J. Org. Chem*, 2015, 80, 3217-3222.

Campbell K.N., et al. (1949) "Studies on γ-Pyrones. II. Synthesis of 4-Piperidinols from Pyrones," J. Org. Chem. 15(2), 337-342.

Casy, A.F. et al. (1976), "Reversed ester analogues of pethidine: isomeric 4-acetoxy-1,2,6-trimethyl-4-phenyrpiperidines." *JPP*, vol. 28, No. 2, pp. 106-110.

Casy, A.F., et al. (1972) "Diastereoisomeric esters of 1,2-dimethyl-4-phenylpiperidin-4-ol and related compounds," J. Chem. Soc., Perkin Trans. 1, 726-731.

Database Registry (2002), Chembridge Corporation: 4-Piperidinol, 4-(2-methoxyphenyl)-1-methyl-2,6-diphenyl-II XP093022694, Database accession No. 471293-86-4 compound with Registry No. 471293-86-4.

Database Registry (2011), Aurora Fine Chemicals: "Spiro[isobenzofuran-1(3H),4'-piperidine]-3-carboxamide, N, N-dimethyl-1'-[(5-methyl-2-furanyl)methyl]-2,2,2-trifluoroacetate (1:1)", XP093038422, retrieved from STN Database accession No. 2649946-46-1 abstract.

Database Registry (2016), Aurora Fine Chemicals: "Piperidine, 4-[(I,3-diethyl-IH-pyrazol-5-yl)methyl]-2, 6-dimethyl," XP093022702, Database accession No. 1993174-76-7 compounds with Registry Nos. 1993174-76-7, 1993166-16-7 and 1993166-02-1.

Database Registry (2018), Aurora Fine Chemicals: "Spiro[isobenzofuran-1(3H),4'-piperidine]-3-carboxamide,N,N-climethy1-1'-(3-thieny1methy1)-", XP093038444, retrieved from STN Database accession No. 2184532-71-4 abstract.

Database Registry (2018), Aurora Fine Chemicals: "4-Piperidinol, 1,2,6-trimethyl-4-(2-methylphenyl)-", XP093022693, Database accession No. 2182802-01-1 compound with Registry No. 2182802-01-1.

(56) References Cited

OTHER PUBLICATIONS

Database Registry (2018), Aurora Fine Chemicals: "Spiro[isobenzofuran-1(3H),4'-piperidine]-3-carboxamide,N,N-climethy1-1'-[(1-methyl-1H-imidazo1-2-yl) methyl]-", XP093038484, retrieved from Database accession No. 2182642-77-7.
Database Registry (2018), Aurora Fine Chemicals: "Spiro[isobenzofuran-1(3H),4'-piperidine]-3-carboxamide,N,N-dimethyl-1'-(2-thiazolylmethyl)-", XP093038443, retrieved from STN Database accession No. 2185335-69-5 abstract.
Database Registry (2018), Aurora Fine Chemicals: "Spiro[isobenzofuran-1(3H),4'-piperidine]-3-carboxamide,N,N-dimethyl-1'-[(5-methyl-2-furanyl)methy1)-, 2,2,2-trifluoroacetate (1:1)", XP093038441, retrieved from STN Database accesion No. 2185363-22-6 abstract.
Database Registry (2021), "2'-Cyclopropyl-6,7-dihydro-6,6'-dimethyls piro[I,7-naphthyridine-8(5H),4'-piperidine]," XP093024335, retrieved from STN Database accession No. 2644543-73-5 abstract.
Database Registry (2021), "2'-Cyclopropyl-7,8-dihydro-6'-methylspiro [I,6-naphthyridine-5(6H),4'-piperidine]," XP093024331, retrieved from STN Database accession No. 2645191-67-7 abstract.
Database Registry (2021), Anonymous: "2'-Cyclopropyl-3,4-dihydro-3,6'-dimethyls piro[2,6-naphthyridine-1(2H),4'piperidine]," XP093024352, retrieved from STN Database accession No. 2620609-98-3 abstract.
Database Registry (2021), Anonymous: "2'-Cyclopropyl-3,4-dihydro-6'-methylspiro [isoquinoline-1(2H),4'-piperidin]-7-ol," XP093024340, retrieved from STN Database accession No. 2631256-91-0 abstract.
Database Registry (2021), Anonymous: "2'-Cyclopropyl-6,7-dihydro-6'-methylspiro [1,7-naphthyridine-8(5H),4' piperidine]-5-methanol," XP093024350, retrieved from STN Database accession No. 2617381-98-1 abstract.
Database Registry (2021), Anonymous: "2'-Cyclopropyl-6,7-dihydro-6'-methylspiro [1,7-naphthyridine-8(5H),4' piperidine]-6-methanol," XP093024346, retrieved from STN Database accession No. 2626788-69-8 abstract.
Database Registry (2021), Anonymous: "2-Cyclopropyl-7',8'-dihydro-2',6-dimethyl spiro[piperidine-4,5'(3'H)-pyrido[4,3-d]py rimidin]-4' (6 'H) -one", XP093024343, retrieved from STN Database accession No. 2631119-41-8 abstract.
Database Registry (2021), Anonymous: "Name not yet assigned", XP093024338, retrieved from STN Database accession No. 2642534-36-7 abstract.
Database Registry (2021), Anonymous: "Name not yet assigned", XP093024344, retrieved from STN Database accession No. 2630494-88-9 abstract.
Database Registry (2021), Anonymous: "rel-(2'R,6'R)-3,4-Dihydro-7-methoxy-2',6' -dimethylspiro[2,6-naphthyridine1(2H), 4'-p iperidine], "XP093024348, retrieved from STN Database accession No. 2625380-27-8 abstract.
Dummer, P.D. et al. (2015), "APOL1 kidney disease risk variants—an evolving landscape," Semin Nephrol. 35(3):222-236. HHS Public Access Author Manuscript; available in PMC May 1, 2016 (25 pages).
Harish, B. et al. (2017) "N-Heterocyclic carbene (NHC)-catalysed atom economical construction of 2,3-disubstituted indoles," Chem. Commun, 2017, 53, 3338-3341.
Harper N.J. et al. (1960) "Some isomeric hydroxypiperidines." J. Am. Chem. Soc., Jan. 1, 1960, pp. 2704-2711.
Harriman, G.C.B., et al. (2000) "Synthesis of 4-substituted 4-arylpiperidines," Tet. Lett. 41(46), 8853-8856.
International Search Report and Written Opinion for International Application No. PCT/US2021/036960, mailed Sep. 29, 2021 (11 pages).
Jones, A.J. et al. (1973), "Carbon-13 Magnetic Resonance: the Stereochemistry of 1,2- and 1,3-Dimethyl-4-phenylpiperidine Derivatives." *Can. J. Chem.*, vol. 41, No. 11, pp. 1782-1789.
Kagabu, S. et al. (2009), "N-Thiophenylethyl-2,2-dichloro-1-cyclopropanecarboxamides: modification of the amide part of carpropamid and examination of fungicidal activity," J. Pestic. Sci. 34(3) 161-172.
Kozikowski, A.P. et al. (1993), "Chemistry, binding affinities, and behavioral properties of a new class of "antineophobic" mitochondrial DBI receptor complex (mDRC) ligands," *J. Med. Chem.* 36(20):2908-2920.
Lennox, A. (2018) "Electrochemical Aminoxyl-Mediated α-Cyanation of Secondary Piperidines for Pharmaceutical Building Block Diversification" J. Am. Chem. Soc. 140, 11227-11231.
Lin, J. et al. (2021), "Oncogene APOL1 promotes proliferation and inhibits apoptosis via activating NOTCH1 signaling pathway in pancreatic cancer," *Cell Death and Disease* 12:760 (11 pages).
Manimekalai, A. et al. (2007), "Benzyl group conformation in 4-benzyl-4-hydroxypiperidines," *J. Struct. Chem.*, vol. 48, No. 6, pp. 1036-1045.
Meyers, A.L. et al. (1985), ".alpha.-Amino carbanions. Preparation, metalation, and alkylation of enamidines. Synthesis of piperidine and pyrrolidine natural products and homologation of carbonyl compounds," *J. Org. Chem.*, vol. 50, No. 7, pp. 1019-1026.
Nitta, A. et al. (2008) "(3R)-3-Amino-4-(2,4,5-trifluorophenyl)-N-{4-[6-(2-methoxyethoxy)benzothiazol-2-yl]tetrahydropyran-4-yl}butanamide as a potent dipeptidyl peptidase IV inhibitor for the treatment of type 2 diabetes," Bioorg. Med. Chem. Lett. 18(2008), 5435-5438.
Nitta, A. et al. (2012) "Pyrrolidinyl phenylurea derivatives as novel CCR3 antagonists," Bioorg. Med. Chem. Lett. 22(2012), 6876-6881.
Pedregal, A. et al. (2012) "Development of LC-MS/MS-Based Receptor Occupancy Tracers and Positron Emission Tomography Radioligands for the Nociceptin/Orphanin FQ (NOP) Receptor," J. Med. Chem. 55, 4955-4967.
Prostakov, N.S. et al. (1975) "Synthesis of 3-Alkyl-2, 4, 6-Triphenylpyridines and 1, 3-Diphenyl-4- and -2-Azafluorenes." Chem Heterocycl Compd, vol. 11, pp. 971-975.
Takai, K. et al., (2014) "Discovery of N-substituted 7-azaindoline derivatives as potent, orally available M1 and M4 muscarinic acetylcholine receptors selective agonist," Bioorg. Med. Chem. Lett. 24(2014), 3189-3193.
Takasawa, R. et al. (2011), "Discovery of a new type inhibitor of human glyoxalase I by myricetin-based 4-point pharmacophore," *Bioorganic Med. Chem. Lett.* 21:4337-4342.
Trotter, B.W. et al. (2001) "2-Arylindole-3-acetamides: FPP-Competitive Inhibitors of Farnesyl Protein Transferase," Bioorg. Med. Chem. Lett. 11(2001) 865-869.
Turnu, F. et al. (2019) "Catalytic Tandem Friedel—Crafts Alkylation/C4—C3 Ring-Contraction Reaction: an Efficient Route for the Synthesis of Indolyl Cyclopropanecarbaldehydes and Ketones," *Org. Lett.* 21:7329-7332, (4 pages).
U.S. Appl. No. 17/923,508, filed Nov. 11, 2022, by Skorecki, et al.
U.S. Appl. No. 18/071,153, filed Nov. 29, 2022, by Dakin et al.
U.S. Appl. No. 18/106,569, filed Feb. 7, 2023, by Dakin et al.
Vajgel, G. et al. (2020), "A single APOL1 nephropathy variant increases risk of advanced lupus nephritis in Brazilians," *J Rheumatol.* 47(8):1209-1217. HHS Public Access Author Manuscript; available in PMC Aug. 1, 2021 (18 pages).
Valles, D.A. et al. (2021), "[alpha], [alpha] '-C—H Bond Difunctionalization of Unprotected Alicyclic Amines," *Org. Lett.*, vol. 23, No. 16, pp. 6367-6371.
Van Wijngaarden, I. et al. (1987) "2-Phenylpyrroles as conformationally restricted benzamide analogs. A new class of potential antipsychotics," J. Med. Chem. 30(11), 2099-2104.
*Vertex Announces Positive Results From Phase 2 Study of VX-147 in APOL1-Mediated Focal Segmental Glomerulosclerosis*, Vertex (Dec. 1, 2021), https://news.vrtx.com/press-release/vertex-announces-positive-results-phase-2-study-vx-147-apol1-mediated-focal-segmental (6 pages).
Winters, M.P. et al. (2008), "Carboxylic acid bioisosteres acylsulfonamides, acylsulfamides, and sulfonylureas as novel antagonists of the CXCR2 receptor," *Bioorganic Med. Chem. Lett.* 18:1926-1930.
Brittain H. G. et al., (2001) "X-Ray Diffraction III: Pharmaceutical Applications of X-ray Powder Diffraction," Spectroscopy, 16(7), pp. 14-18.
CAS Registry No. 539793-33-4 (Year: 2003).
CAS Registry No. 924466-70-6 (Year: 2007).

(56) References Cited

OTHER PUBLICATIONS

Database Registry (2005) Anonymous, CAplus Registry No. RN 847480-40-4, A88:A93A94A88:A90A88:A97A94A88:AA88:A91.
Database Registry (2007), Chemical Abstracts Service, Columbus, Ohio, Accession No. RN 930014-44-1, Entered STN: Apr. 13, 2007.
Database Registry (2007), Chemical Abstracts Service, Columbus, Ohio, Accession No. RN 1391756-29-8, Entered STN: Aug. 16, 2012.
Database Registry (2007), Chemical Abstracts Service, Columbus, Ohio, Accession No. RN 1391756-83-4, Entered STN: Aug. 16, 2012.
Horner, et al. DE 1266763 (abstract) retrieved from STN Accession No. 1968:506703, CAPLUS, Apr. 25, 1968.
Johansson, H. et al. (2013), "3-Substituted 2-phenyl-indoles: privileged structures for medicinal chemistry" RSC Adv, 3, 945-960.
Joshi, K.C. et al. (1978), "Synthesis and CNS Activity of Some Fluorine Containing 3-Indolylglyoxamides and Tryptamines" Agric. Biol. Chem., 42(9), pp. 1723-1726.
Kang H. et al. (2018), "Potent aromatase inhibitors and molecular mechanism of inhibitory action," European Journal of Medicinal Chemistry, 143, 426-437.
Naik M. et al. (2014), "2-Phenylindole and arylsulfonamide: novel scaffolds bactericidal against *Mycobacterium tuberculosis*" ACS Med. Chem. Lett. 2014, 5, 9, 1005-1009.
Notice of Allowance and Fee(s) Due for U.S. Appl. No. 17/161,474, mailed Mar. 5, 2024.
Notice of Allowance and Fee(s) Due for U.S. Appl. No. 17/161,474, mailed May 28, 2024.
Shaw D. et al. (2001), "2-Aryl Indole NK1 Antagonists: Optimisation of the Amide Substituent," Bioorg. Med. Chem. Lett., 11, 3031-3034.
The United States Pharmacopeia, Jan. 1, 1995, 23rd Revision, USP 23/NF 18, General Chapter on X-ray diffraction, pp. 1843-1844.
U.S. Appl. No. 18/504,559, filed Nov. 8, 2023.
Z. Linxiang, "Chemical Pharmaceutical Technology," p. 405, China Medical Science Press, Aug. 2015.
Zhang, G.-N. et al. (2019), "An Efficient Synthesis of N-Aryl-2-(Indol-3-yl)-Acetamides via Multi-Component Reactions," Heterocycles, 98(4), 535-543.
CAS Registry No. 850916-71-1 (Year: 2005).
CAS Registry No. 920692-07-5 (Year: 2007).
Croscarmellose Sodium; www.drugs.com/inactive/croscarmellose-sodium-204.html; archived via Wayback Machine on Dec. 27, 2011 (Year: 2011).
Hölzer AW et al. (1979) "Evaluation of sodium stearyl fumarate as a tablet lubricant," International Journal of Pharmaceutics, 1979, 2, pp. 145-153.
Lv J. et al. (2009) "Combination therapy of prednisone and ACE inhibitor versus ACE-inhibitor therapy alone in patients with IgA nephropathy: a randomized controlled trial." Am. J. Kidney Dis. 2009, 53(1):26-32.
Momoniat T. et al. (2019) ACE inhibitors and ARBs: Managing potassium and renal function. Cleveland Clinic J. Med., 2019, 86 (9) 601-607.
Remington, "Tablet Ingredients", Remington: the Science and Practice of Pharmacy, 21st Edition, Beringer et al. Editors, 2005, pp. 891-894 (Year: 2005).
Topham, P. (2009) "Proteinuric renal disease," Clin. Med., 2009, 9(3):284-287.
CAS Registry No. 221281-66-9 (Year: 2007).
Charlet-Fagnere, C. et al. (1996), "Studies on the Dimerization of Melatonin (5-Methoxy-N-acetyltryptamine) and Related Compounds in Acid Medium. Oxidation of 2-Arylindolines into 2-Arylindoles" Bulletin de la Societe Chimique de France, 133(1), 39-50.
Cooper, L.C. et al. (2001) "2-Aryl Indole NK1 Receptor Antagonists: Optimisation of Indole Substitution" Bioorganic & Medicinal Chemistry Letters, 11(9), 1233-1236.
Remington, "Tablet Ingredients", Remington: the Science and Practice of Pharmacy, 21st Edition, Beringer et al., 2005, pp. 891-894 (Year: 2005).
Wu, K. et al. (2018) "Rhll-Catalyzed Intermolecular C—H Arylation of Aromatics with Diazo Quinones" Chem. Eur. J., 24, 4815.

* cited by examiner

SOLID FORMS OF APOL1 INHIBITOR AND METHODS OF USING SAME

This application claims the benefit of priority of U.S. Provisional Application No. 63/038,271, filed Jun. 12, 2020, the contents of which are incorporated by reference herein in its entirety.

This disclosure provides solid forms of a compound that may inhibit apolipoprotein L1 (APOL1) and methods of using those solid forms to treat APOL1 mediated kidney disease, including focal segmental glomerulosclerosis (FSGS) and/or non-diabetic kidney disease (NDKD). In some embodiments, the FSGS and/or NDKD is associated with common APOL1 genetic variants (G1: S342G:I384M and G2: N388del:Y389del).

FSGS is a disease of the podocyte (glomerular visceral epithelial cells) responsible for proteinuria and progressive decline in kidney function. NDKD is a disease characterized by hypertension and progressive decline in kidney function. Human genetics support a causal role for the G1 and G2 APOL1 variants in inducing kidney disease. Individuals with two APOL1 risk alleles are at increased risk of developing end-stage kidney disease (ESKD), including FSGS, human immunodeficiency virus (HIV)-associated nephropathy, NDKD, arterionephrosclerosis, lupus nephritis, microalbuminuria, and chronic kidney disease. See, P. Dummer et al., *Semin Nephrol.* 35(3): 222-236 (2015).

APOL1 is a 44 kDa protein that is only expressed in humans, gorillas, and baboons. APOL1 is produced mainly by the liver and contains a signal peptide that allows for secretion into the bloodstream, where it circulates bound to a subset of high-density lipoproteins. APOL1 is responsible for protection against the invasive parasite, *Trypanosoma brucei brucei* (T. b. *brucei*). APOL1 G1 and G2 variants confer additional protection against *trypanosoma* species that cause sleeping sickness. Although normal plasma concentrations of APOL1 are relatively high and can vary at least 20-fold in humans, circulating APOL1 is not causally associated with kidney disease.

However, APOL1 in the kidney is thought to be responsible for the development of kidney diseases, including FSGS and NDKD. Under certain circumstances, APOL1 protein synthesis can be increased by approximately 200-fold by pro-inflammatory cytokines such as interferons or tumor necrosis factor-α. In addition, several studies have shown that APOL1 protein can form pH-gated $Na^+/K^+$ pores in the cell membrane, resulting in a net efflux of intracellular $K^+$, ultimately resulting in activation of local and systemic inflammatory responses, cell swelling, and death.

The risk of ESKD is substantially higher in people of recent sub-Saharan African ancestry as compared to those of European ancestry. In the United States, ESKD is responsible for nearly as many lost years of life in women as from breast cancer and more lost years of life in men than from colorectal cancer. Currently, FSGS and NDKD are managed with symptomatic treatment (including blood pressure control using blockers of the renin angiotensin system), and patients with FSGS and heavy proteinuria may be offered high dose steroids. Corticosteroids induce remission in a minority of patients and are associated with numerous and, at times, severe side effects, and are often poorly tolerated. These patients, and particularly individuals of recent sub-Saharan African ancestry with two APOL1 risk alleles, experience faster disease progression leading to ESKD.

Thus, there is an unmet medical need for treatment for APOL1 mediated kidney diseases, including FSGS, NDKD, and ESKD. In view of evidence that APOL1 plays a causative role in inducing and accelerating the progression of kidney disease, inhibition of APOL1 should have a positive impact on patients with APOL1 mediated kidney disease, particularly those who carry two APOL1 risk alleles (i.e., are homozygous or compound heterozygous for the G1 or G2 alleles).

Compound I, its method of preparation, and physicochemical data are disclosed as Compound 2 in U.S. Provisional Application No. 62/780,667, filed on Dec. 17, 2018, the entirety of which is incorporated herein by reference. Additional information, such as solid state forms (e.g., Form A), are disclosed as Compound 2 in U.S. application Ser. No. 16/717,099 and PCT International Application No. PCT/US2019/066746, both of which were filed on Dec. 17, 2019, the entirety of each of which is incorporated herein by reference.

One aspect of the disclosure provides a new solid state form, ethanol solvate Form A, of Compound I, which can be employed in the treatment of diseases mediated by APOL1, such as FSGS and NDKD, and methods of making the same.

(I)

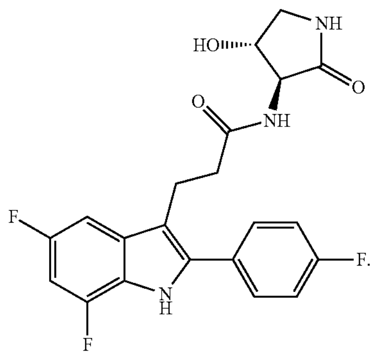

Another aspect of the disclosure provides a new solid state form, ethanol solvate Form B, of Compound I, which can be employed in the treatment of diseases mediated by APOL1, such as FSGS and NDKD, and methods of making the same.

Another aspect of the disclosure provides a new solid state form, citric acid cocrystal Form A, of Compound I, which can be employed in the treatment of diseases mediated by APOL1, such as FSGS and NDKD, and methods of making the same.

Another aspect of the disclosure provides a new solid state form, Form B, of Compound I, which can be employed in the treatment of diseases mediated by APOL1, such as FSGS and NDKD, and methods of making the same.

Another aspect of the disclosure provides novel methods of preparing Form A of Compound I.

In some embodiments, the disclosure provides a method of preparing Form A of Compound I comprising:

repeated distillation of Compound I in 2-methyltetrahydrofuran;

heating to 62.5° C. in a solvent comprising methanol for about 35 minutes;

cooling to 25° C.; and isolating Form A of Compound I.

In some embodiments, the solvent comprising methanol is methanol. In some embodiments, the solvent comprising methanol further comprises ethanol. In some embodiments, the solvent comprising methanol further comprises propanol. In some embodiments, the solvent comprising methanol further comprises 1-propanol.

In some embodiments, the method provides Compound I Form A with reduced agglomeration, improved dissolution, and improved processability (e.g., improved filtration and drying properties).

In some embodiments, the disclosure provides a method of preparing Form A of Compound I comprising:

- mixing Compound I in 2-methyltetrahydrofuran and a solvent comprising methanol;
- heating to 62.5° C. for about 20 minutes;
- charging with heptane over about 1 hour;
- adding seed crystals of Form A of Compound I;
- holding at 62.5° C. for about 1 hour;
- charging with heptane over about 5.5 hours;
- cooling to 25° C.; and
- isolating Form A of Compound I.

In some embodiments, the solvent comprising methanol is methanol. In some embodiments, the solvent comprising methanol further comprises ethanol. In some embodiments, the solvent comprising methanol further comprises propanol. In some embodiments, the solvent comprising methanol further comprises 1-propanol.

In some embodiments, the method provides Compound I Form A with reduced agglomeration, improved dissolution, and improved processability (e.g., improved filtration and drying properties).

In some embodiments, the disclosure provides a method of preparing Form A of Compound I comprising:

- mixing Compound I in 2-methyltetrahydrofuran and a solvent comprising ethanol;
- heating to 62.5° C. for about 20 minutes;
- charging with heptane over about 5 minutes;
- adding seed crystals of Form A of Compound I;
- holding at 62.5° C. for about 1 hour;
- charging with heptane over about 12 hours;
- cooling to 25° C.; and
- isolating Form A of Compound I.

In some embodiments, the solvent comprising ethanol is ethanol.

In some embodiments, the method provides Compound I Form A with reduced agglomeration, improved dissolution, and improved processability (e.g., improved filtration and drying properties).

Another aspect of the disclosure provides methods of treating FSGS and/or NDKD comprising administering to a subject in need thereof, a solid form of Compound I selected from Compound I ethanol solvate Form A, Compound I ethanol solvate Form B, Compound I citric acid cocrystal Form A, and Compound I Form B, or a pharmaceutical composition comprising the same. In some embodiments, the solid form of Compound I is selected from Compound I ethanol solvate Form A, Compound I ethanol solvate Form B, and Compound I citric acid cocrystal Form A.

In some embodiments, the methods of treatment include administration of at least one additional active agent to the subject in need thereof, either in the same pharmaceutical composition as a solid form of Compound I selected from Compound I ethanol solvate Form A, Compound I ethanol solvate Form B, Compound I citric acid cocrystal Form A, and Compound I Form B, or as separate compositions. In some embodiments, the solid form of Compound I is selected from Compound I ethanol solvate Form A, Compound I ethanol solvate Form B, and Compound I citric acid cocrystal Form A.

In some embodiments, the solid form of Compound I and the at least one additional active agent are co-administered in the same pharmaceutical composition. In some embodiments, the solid form of Compound I and the at least one additional active agent are co-administered in separate pharmaceutical compositions. In some embodiments, the solid form of Compound I and the at least one additional active agent are co-administered simultaneously. In some embodiments, the solid form of Compound I and the at least one additional active agent are co-administered sequentially.

Also provided are methods of inhibiting APOL1, comprising administering to a subject in need thereof, a solid form of Compound I selected from Compound I ethanol solvate Form A, Compound I ethanol solvate Form B, Compound I citric acid cocrystal Form A, and Compound I Form B, or a pharmaceutical composition comprising the same. In some embodiments, the solid form of Compound I is selected from Compound I ethanol solvate Form A, Compound I ethanol solvate Form B, and Compound I citric acid cocrystal Form A.

Also disclosed herein is a solid form of Compound I selected from Compound I ethanol solvate Form A, Compound I ethanol solvate Form B, Compound I citric acid cocrystal Form A, and Compound I Form B for use in therapy. In some embodiments, the solid form of Compound I is combined with at least one additional active agent for simultaneous, separate, or sequential use in therapy. In some embodiments, when the use is simultaneous, the solid form of Compound I and the at least one additional active agent are in separate pharmaceutical compositions. In some embodiments, when the use is simultaneous, the solid form of Compound I and the at least one additional active agent are together in the same pharmaceutical composition.

Also disclosed herein is a pharmaceutical composition comprising a solid form of Compound I selected from Compound I ethanol solvate Form A, Compound I ethanol solvate Form B, Compound I citric acid cocrystal Form A, and Compound I Form B for use in therapy.

It should be understood that references herein to methods of treatment and/or inhibition (e.g., methods of treating FSGS and/or NDKD, methods of inhibiting APOL1) using one or more compounds (e.g., one or more solid forms of Compound I, e.g., Compound I ethanol solvate Form A, Compound I ethanol solvate Form B, Compound I citric acid cocrystal Form A, or Compound I Form B) should also be interpreted as references to:

- one or more compounds (e.g., one or more solid forms of Compound I, e.g., Compound I ethanol solvate Form A, Compound I ethanol solvate Form B, Compound I citric acid cocrystal Form A, or Compound I Form B), for use in methods of treatment and/or inhibition; and/or
- the use of one or more compounds (e.g., one or more solid forms of Compound I, e.g., Compound I ethanol solvate Form A, Compound I ethanol solvate Form B, Compound I citric acid cocrystal Form A, or Compound I Form B) in the manufacture of a medicament for treatment and/or inhibition.

DEFINITIONS

Figure 1:
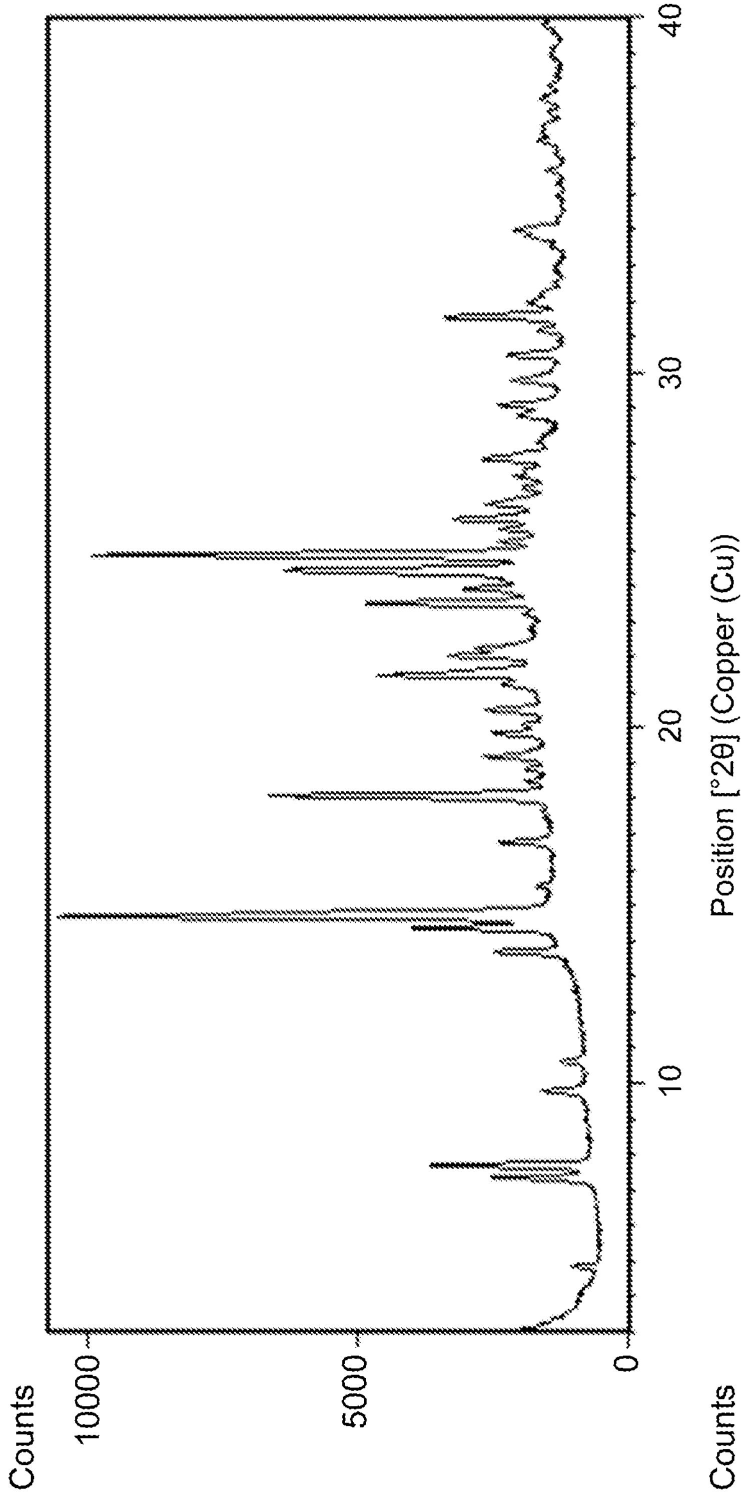
FIG. 1 depicts an XRPD diffractogram of Ethanol Solvate Form A of Compound I.

The term "APOL1," as used herein, means apolipoprotein L1 protein, and the term "APOL1" means apolipoprotein L1 gene.

The term "APOL1 mediated kidney disease" refers to a disease or condition that impairs kidney function and can be attributed to APOL1. In some embodiments APOL1 mediated kidney disease is associated with patients having two APOL1 risk alleles, e.g., patients who are homozygous or compound heterozygous for the G1 or G2 alleles. In some embodiments, the APOL1 mediated kidney disease is selected from ESKD, NDKD, FSGS, HIV-associated nephropathy, arterionephrosclerosis, lupus nephritis, microalbuminuria, and chronic kidney disease.

The term "FSGS," as used herein, means focal segmental glomerulosclerosis, which is a disease of the podocyte (glomerular visceral epithelial cells) responsible for proteinuria and progressive decline in kidney function. In some embodiments, FSGS is associated with two APOL1 risk alleles.

The term "NDKD," as used herein, means non-diabetic kidney disease, which is characterized by severe hypertension and progressive decline in kidney function. In some embodiments, NDKD is associated with two APOL1 risk alleles.

The terms "ESKD" and "ESRD" are used interchangeably herein to refer to end stage kidney disease or end stage renal disease. ESKD/ESRD is the last stage of kidney disease, i.e., kidney failure, and means that the kidneys have stopped working well enough for the patient to survive without dialysis or a kidney transplant. In some embodiments, ESKD/ESRD is associated with two APOL1 risk alleles.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above the relative amount of such isotopologues in total will be less than 49.9% of the compound. In other embodiments, the relative amount of such isotopologues in to will be less than 47.5%, less than 40%, less than 32.5%, less than 25%, less than 17.5%, less than 10%, less than 5%, less than 3%, less than 1%, or less than 0.5% of the compound.

Non-limiting examples of suitable solvents that may be used in this disclosure include water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptanes, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Non-limiting examples of suitable bases that may be used in this disclosure include 1,8-diazabicyclo[5.4.0]undec-7-ene (DBU), potassium tert-butoxide (KOtBu), potassium carbonate ($K_2CO_3$), N-methylmorpholine (NMN), triethylamine ($Et_3N$; TEA), diisopropyl-ethyl amine ($i\text{-}Pr_2EtN$; DIPEA), pyridine, potassium hydroxide (KOH), sodium hydroxide (NaOH), lithium hydroxide (LiOH) and sodium methoxide (NaOMe; $NaOCH_3$).

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. In some embodiments, the term "about" refers to a value ±10%, ±8%, ±6%, ±5%, ±4%, ±2%, or ±1% of a referenced value.

The terms "patient" and "subject" are used interchangeably herein and refer to an animal, including a human. In some embodiments, the subject is a human.

The terms "effective dose" and "effective amount" are used interchangeably herein and refer to that amount of compound that produces the desired effect for which it is administered (e.g., improvement in symptoms of FSGS and/or NDKD, lessening the severity of FSGS and/NDKD or a symptom of FSGS and/or NDKD, and/or reducing progression of FSGS and/or NDKD or a symptom of FSGS and/or NDKD). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treatment" and its cognates refer to slowing or stopping disease progression. "Treatment" and its cognates, as used herein, include, but are not limited to, the following: eliminating or reducing the severity of any symptom of the kidney disease, complete or partial remission, lower risk of kidney failure (e.g., ESRD), and disease-related complications (e.g., edema, susceptibility to infections, or thrombo-embolic events). Improvements in or lessening the severity of any of the symptoms of APOL1 mediated kidney can be readily assessed according to methods and techniques known in the art or subsequently developed. In some embodiments, the terms "treat," "treating," and "treatment" refer to the lessening of severity of one or more symptoms of FSGS and/or NDKD.

The solid forms of Compound I disclosed herein may be administered once daily, twice daily, or three times daily, for example, for the treatment of FSGS. In some embodiments, the solid form of Compound I selected from Compound I ethanol solvate Form A, Compound I ethanol solvate Form B, Compound I citric acid cocrystal Form A, and Compound I Form B (such as, e.g., the solid form of Compound I selected from Compound I ethanol solvate Form A, Compound I ethanol solvate Form B, and Compound I citric acid cocrystal Form A) is administered once daily. In some embodiments, the solid form of Compound I selected from Compound I ethanol solvate Form A, Compound I ethanol solvate Form B, Compound I citric acid cocrystal Form A, and Compound I Form B (such as, e.g., the solid form of Compound I selected from Compound I ethanol solvate Form A, Compound I ethanol solvate Form B, and Compound I citric acid cocrystal Form A) is administered twice daily. In some embodiments, the solid form of Compound I selected from Compound I ethanol solvate Form A, Compound I ethanol solvate Form B, Compound I citric acid cocrystal Form A, and Compound I Form B (such as, e.g., the solid form of Compound I selected from Compound I ethanol solvate Form A, Compound I ethanol solvate Form B, and Compound I citric acid cocrystal Form A) is administered three times daily.

In some embodiments, 2 mg to 1500 mg of the solid form of Compound I selected from Compound I ethanol solvate Form A, Compound I ethanol solvate Form B, Compound I citric acid cocrystal Form A, and Compound I Form B (such as, e.g., the solid form of Compound I selected from Compound I ethanol solvate Form A, Compound I ethanol solvate Form B, and Compound I citric acid cocrystal Form A) is administered once daily, twice daily, or three times daily.

As used herein, the term "ambient conditions" means room temperature, open air, and uncontrolled humidity condition.

As used herein, the terms "crystalline form" and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, solid state nuclear magnetic resonance (SSNMR), differential scanning calorimetry (DSC), infrared radiation (IR), and/or thermogravimetric analysis (TGA). Accordingly, as used herein, the term "crystalline Form B of Compound I" refers to a unique crystalline form that can be identified and distinguished from other crystalline forms of Compound I by one or more characterization techniques including, for example, X-ray powder diffraction (XRPD), single crystal X-ray diffraction, SSNMR, differential scanning calorimetry (DSC), infrared radiation (IR), and/or thermogravimetric analysis (TGA). In some embodiments, the novel crystalline Form B of Compound I is characterized by an X-ray powder diffractogram having one or more signals at one or more specified two-theta values (°2θ).

As used herein, the term "SSNMR" refers to the analytical characterization method of solid state nuclear magnetic resonance. SSNMR spectra can be recorded at ambient conditions on any magnetically active isotope present in the sample. The typical examples of active isotopes for small molecule active pharmaceutical ingredients include $^{1}H$, $^{2}H$, $^{13}C$, $^{19}F$, $^{31}P$, $^{15}N$, $^{14}N$, $^{35}Cl$, $^{11}B$, $^{7}Li$, $^{17}O$, $^{23}Na$, $^{79}Br$, and $^{195}Pt$.

As used herein, the term "XRPD" refers to the analytical characterization method of X-ray powder diffraction. XRPD patterns can be recorded under ambient conditions in transmission or reflection geometry using a diffractometer.

As used herein, the terms "X-ray powder diffractogram," "X-ray powder diffraction pattern," and "XRPD pattern" interchangeably refer to an experimentally obtained pattern plotting signal positions (on the abscissa) versus signal intensities on the ordinate). For an amorphous material, an X-ray powder diffractogram may include one or more broad signals; and for a crystalline material, an X-ray powder diffractogram may include one or more signals, each identified by its angular value as measured in degrees 2θ (°2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) selected from . . . ."

A "signal" or "peak," as used herein, refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [a] two-theta value [ ] of . . . ," and/or "a signal at at least . . . two-theta value(s) selected from . . . " refer to X-ray reflection positions as measured and observed in X-ray powder diffraction experiments (°2θ).

The repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta).

As used herein, the terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

The terms "X-ray powder diffractogram having a signal at . . . two-theta values" and "X-ray powder diffractogram comprising a signal at . . . two-theta values" are used interchangeably herein and refer to an XRPD pattern that contains X-ray reflection positions as measured and observed in X-ray powder diffraction experiments (°2θ).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal positions in XRPD diffractograms (in degrees two-theta (°2θ) referred to herein) generally mean that value reported is ±0.2 degrees 2θ of the reported value, an art-recognized variance.

As used herein, an SSNMR spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the signal positions in SSNMR spectra (in ppm) referred to herein generally mean that value reported is ±0.2 ppm of the reported value, an art-recognized variance.

As used herein, a DSC curve is "substantially similar to that in [a particular] Figure" when at least 90%, such as at least 95%, at least 98%, or at least 99%, of the features in the two curves overlap. In determining "substantial similarity," one of ordinary skill in the art will understand that there may be variation in the intensities and/or peak (e.g., endotherm or exotherm) positions in DSC curves even for the same solid form.

As used herein, a TGA thermogram is "substantially similar to that in [a particular] Figure" when at least 90%, such as at least 95%, at least 98%, or at least 99%, of the features in the two thermograms overlap. In determining "substantial similarity," one of ordinary skill in the art will understand that there may be variation in the intensities and/or peak (e.g., degradation peak) positions in TGA thermograms even for the same solid form.

As used herein, a crystalline form is "substantially pure" when it accounts for an amount by weight equal to or greater than 90% of the sum of all solid form(s) in a sample as determined by a method in accordance with the art, such as, e.g., quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, the term "DSC" refers to the analytical method of Differential Scanning Calorimetry.

As used herein, the term "TGA" refers to the analytical method of Thermo Gravimetric (or thermogravimetric) Analysis.

Compound I is disclosed as Compound 2 in U.S. application Ser. No. 16/717,099, filed on Dec. 17, 2019, and PCT International Application No. PCT/US2019/066746, filed on Dec. 17, 2019, the entire contents of each of which are incorporated herein by reference.

Compound I is depicted as follows:

(I)

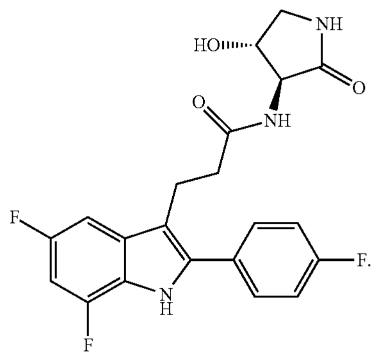

Forms of Compound I, such as Form A, Hydrate Form A, Hydrate Form B, Hydrate Form C, Hydrate Form D, Hydrate Form E, Hydrate Form F, MTBE Solvate Form A, DMF Solvate Form A, and Amorphous Form of Compound I, are disclosed in U.S. application Ser. No. 16/717,099 and PCT International Application No PCT/US2019/066746, both of which were filed on Dec. 17, 2019 and both of which are incorporated herein by reference.

Ethanol Solvate Form A of Compound I

One embodiment of the disclosure provides an ethanol solvate Form A of Compound I. In some embodiments, the ethanol solvate Form A of Compound I is substantially pure.

In some embodiments, the ethanol solvate Form A of Compound I is characterized by an X-ray powder diffractogram having a signal at 14.4±0.2 and/or 21.5±0.2 two-theta. In some embodiments, the ethanol solvate Form A of Compound I is characterized by an X-ray powder diffractogram having (a) a signal at 14.4±0.2 and/or 21.5±0.2 two-theta; and (b) a signal at 23.5±0.2 and/or 24.8±0.2 two-theta.

In some embodiments, the ethanol solvate Form A of Compound I is characterized by an X-ray powder diffractogram having a signal at one or more two-theta values selected from 14.4±0.2, 21.5±0.2, 23.5±0.2, and 24.8±0.2. In some embodiments, ethanol solvate Form A of Compound I is characterized by an X-ray powder diffractogram having a signal at the following two-theta values: 14.4±0.2, 21.5±0.2, 23.5±0.2, and 24.8±0.2. In some embodiments, the ethanol solvate Form A of Compound I is characterized by an X-ray powder diffractogram having (a) a signal at the following two-theta values: 14.4±0.2, 21.5±0.2, 23.5±0.2, and 24.8±0.2; and (b) a signal at one or more two-theta values selected from 14.7±0.2, 14.8±0.2, 18.1±0.2, and 24.4±0.2. In some embodiments, the ethanol solvate Form A of Compound I is characterized by an X-ray powder diffractogram having signals at the following two-theta values: 14.4±0.2, 14.7±0.2, 14.8±0.2, 18.1±0.2, 21.5±0.2, 23.5±0.2, 24.4±0.2, and 24.8±0.2.

In some embodiments, the ethanol solvate Form A is characterized by an X-ray powder diffractogram substantially similar to that in FIG. 1.

In some embodiments, the ethanol solvate Form A of Compound I is characterized by a $^{13}C$ NMR spectrum having one or more signals selected from 18.0±0.2 ppm, 57.5±0.2 ppm, 58.0±0.2 ppm, 116.7±0.2 ppm, and 128.0±0.2 ppm. In some embodiments, the ethanol solvate Form A of Compound I is characterized by a $^{13}C$ NMR spectrum having signals at 18.0±0.2 ppm, 57.5±0.2 ppm, 58.0±0.2 ppm, 116.7±0.2 ppm, and 128.0±0.2 ppm. In some embodiments, the ethanol solvate Form A of Compound I is characterized by a $^{13}C$ NMR spectrum having (a) signals at 18.0±0.2 ppm, 57.5±0.2 ppm, 58.0±0.2 ppm, 116.7±0.2 ppm, and 128.0±0.2 ppm and (b) one or more signals selected from 18.9±0.2 ppm, 112.4±0.2 ppm, 120.6±0.2 ppm, 126.4±0.2 ppm, and 131.2±0.2 ppm. In some embodiments, the ethanol solvate Form A of Compound I is characterized by a $^{13}C$ NMR spectrum having signals at 18.0±0.2 ppm, 18.9±0.2 ppm, 57.5±0.2 ppm, 58.0±0.2 ppm, 112.4±0.2 ppm, 116.7±0.2 ppm, 120.6±0.2 ppm, 126.4±0.2 ppm, 128.0±0.2 and 131.2±0.2 ppm.

Figure 2:
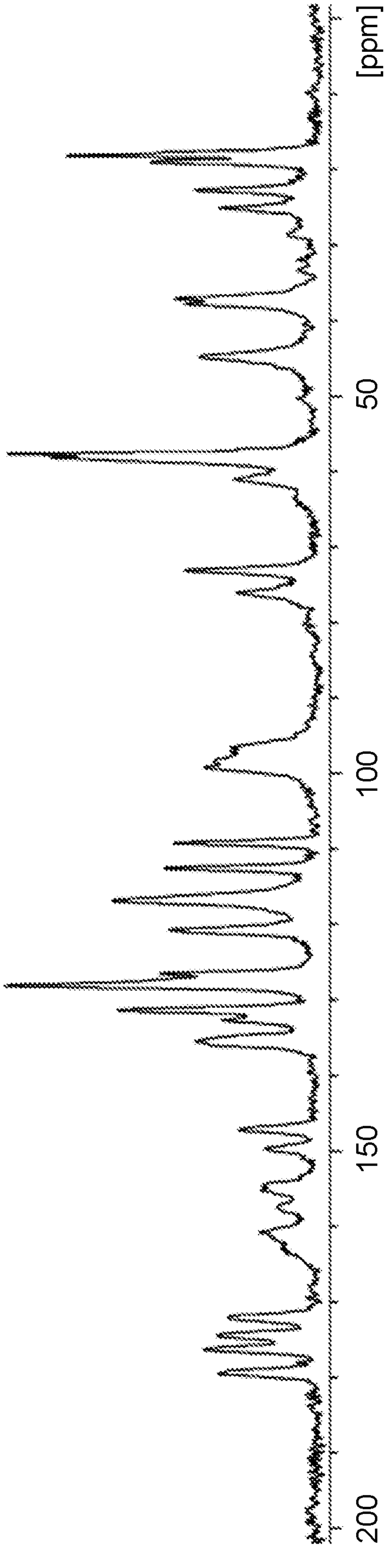
FIG. 2 depicts a solid state $^{13}C$ NMR spectrum of Ethanol Solvate Form A of Compound I.

In some embodiments, the ethanol solvate Form A is characterized by a $^{13}C$ NMR spectrum substantially similar to that in FIG. 2.

In some embodiments, the ethanol solvate Form A of Compound I is characterized by a $^{19}F$ NMR spectrum having a signal at one or more ppm values selected from −136.0±0.2 ppm, −131.2±0.2 ppm, −126.0±0.2 ppm, −122.9±0.2 ppm, −113.0±0.2 ppm, and −111.5±0.2 ppm. In some embodiments, the ethanol solvate Form A of Compound I is characterized by a $^{19}$F NMR spectrum having signals at −136.0±0.2 ppm, −131.2±0.2 ppm, −126.0±0.2 ppm, −122.9±0.2 ppm, −113.0±0.2 ppm, and −111.5±0.2 ppm.

Figure 3:
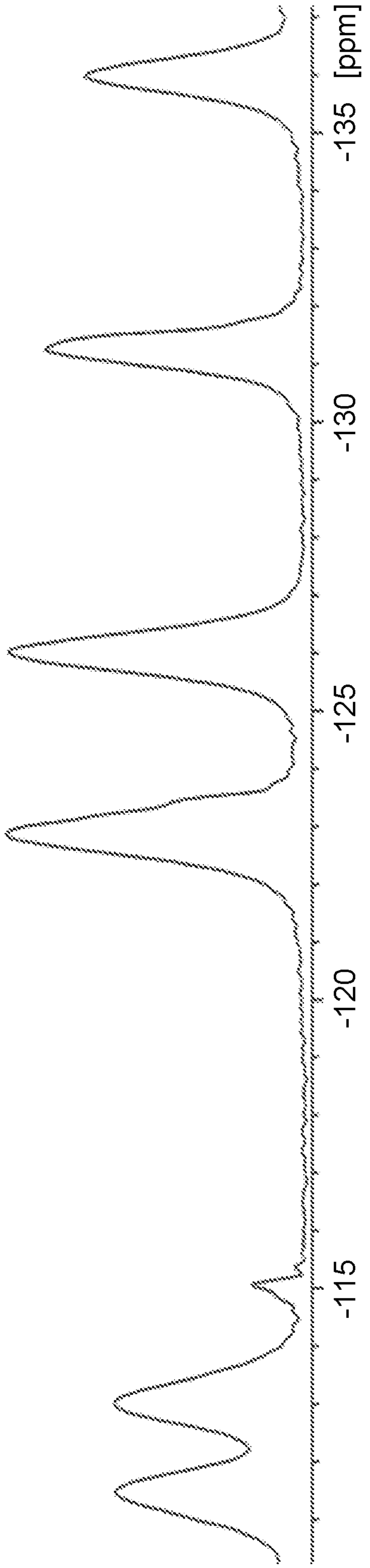
FIG. 3 depicts a solid state $^{19}F$ NMR spectrum of Ethanol Solvate Form A of Compound I.

In some embodiments, the ethanol solvate Form A is characterized by a $^{19}$F NMR spectrum substantially similar to that in FIG. 3.

Ethanol Solvate Form B of Compound I

One embodiment of the disclosure provides an ethanol solvate Form B of Compound I. In some embodiments, the ethanol solvate Form B of Compound I is substantially pure.

In some embodiments, the ethanol solvate Form B of Compound I is characterized by an X-ray powder diffractogram having a signal at 11.4±0.2 and/or 15.3±0.2 two-theta. In some embodiments, the ethanol solvate Form B of Compound I is characterized by an X-ray powder diffractogram having (a) a signal at 11.4±0.2 and/or 15.3±0.2 two-theta; and (b) a signal at 19.5±0.2 two-theta.

In some embodiments, the ethanol solvate Form B of Compound I is characterized by an X-ray powder diffractogram having a signal at one or more two-theta values selected from 11.4±0.2, 15.3±0.2, and 19.5±0.2. In some embodiments, ethanol solvate Form B of Compound I is characterized by an X-ray powder diffractogram having a signal at the following two-theta values: 11.4±0.2, 15.3±0.2, and 19.5±0.2. In some embodiments, the ethanol solvate Form B of Compound I is characterized by an X-ray powder diffractogram having (a) a signal at the following two-theta values: 11.4±0.2, 15.3±0.2, and 19.5±0.2; and (b) a signal at one or more two-theta values selected from 7.6±0.2, 15.1±0.2, 15.6±0.2, and 24.0±0.2. In some embodiments, the ethanol solvate Form B of Compound I is characterized by an X-ray powder diffractogram having signals at the following two-theta values: 7.6±0.2, 11.4±0.2, 15.1±0.2, 15.3±0.2, 15.6±0.2, 19.5±0.2, and 24.0±0.2.

Figure 4:
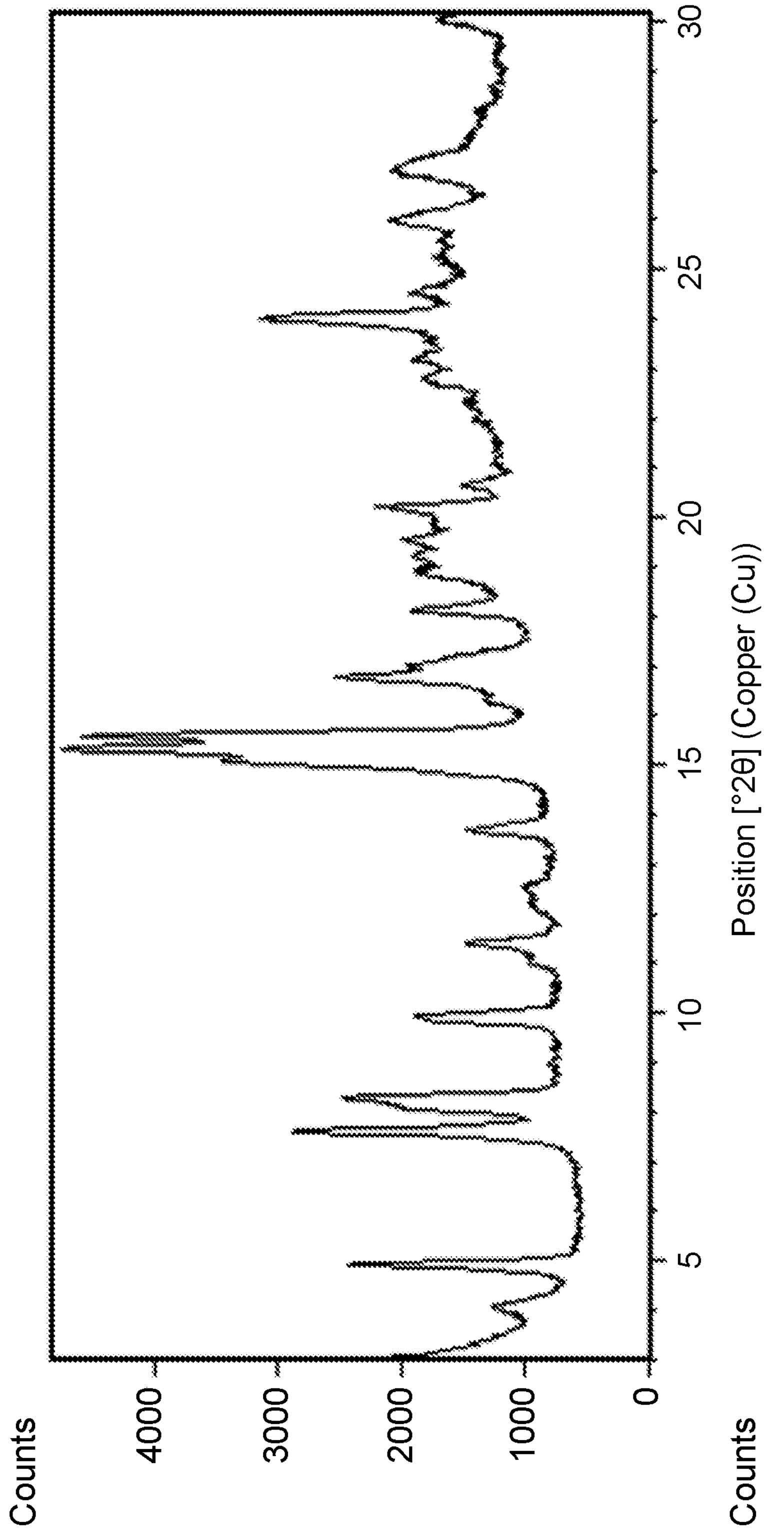
FIG. 4 depicts an XRPD diffractogram of Ethanol Solvate Form B of Compound I.

In some embodiments, the ethanol solvate Form B is characterized by an X-ray powder diffractogram substantially similar to that in FIG. 4.

In some embodiments, the ethanol solvate Form B is characterized by a TGA thermogram showing multiple weight loss from ambient temperature to 135° C. of about 3%.

Figure 5:
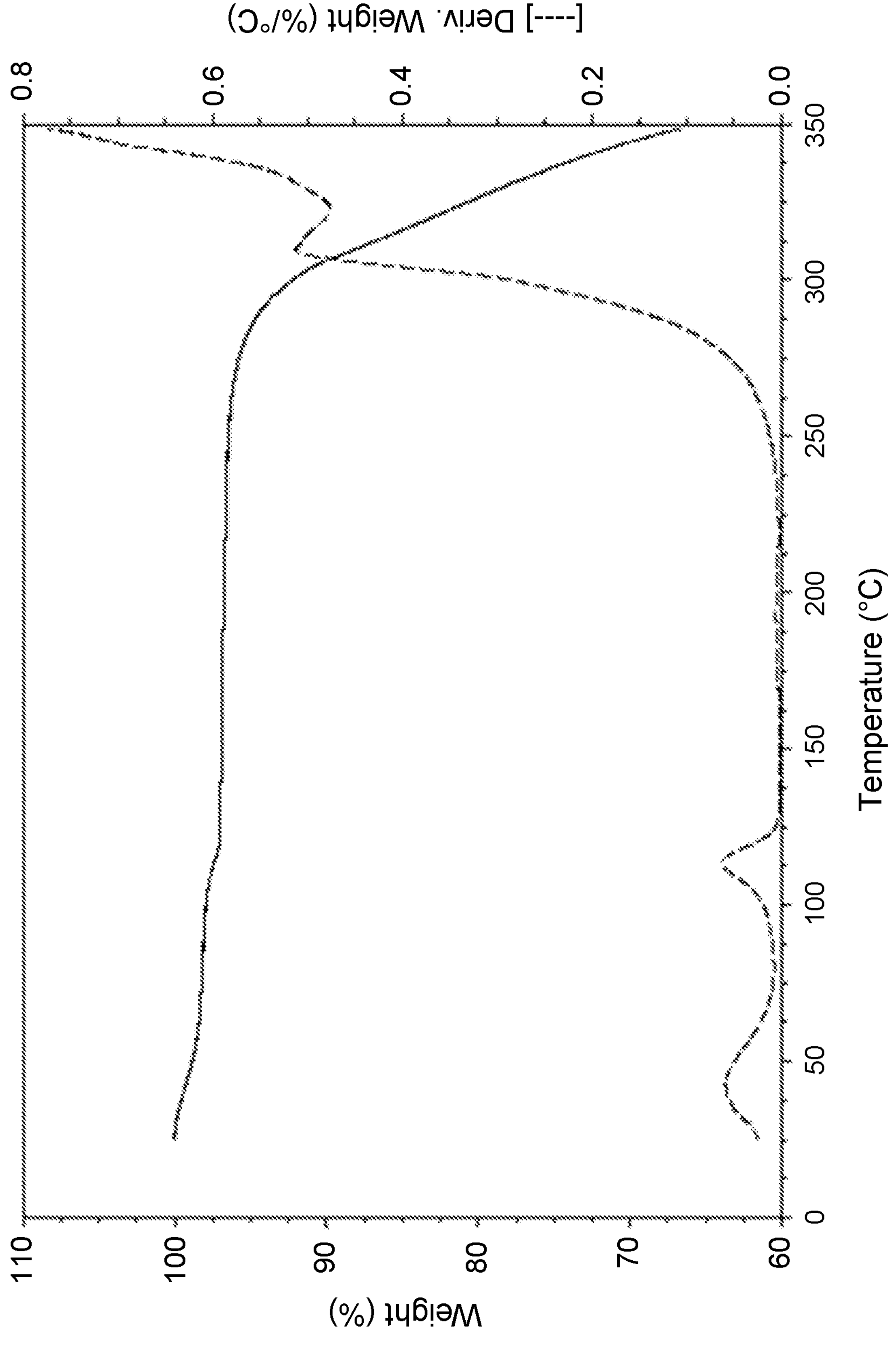
FIG. 5 depicts a TGA thermogram of Ethanol Solvate Form B of Compound I.

In some embodiments, the ethanol solvate Form B is characterized by a TGA thermogram substantially similar to that in FIG. 5.

In some embodiments, the ethanol solvate Form B is characterized by a DSC curve having multiple endothermic and exothermic peaks at about 78° C., about 128° C., about 148° C., and about 197° C.

Figure 6:
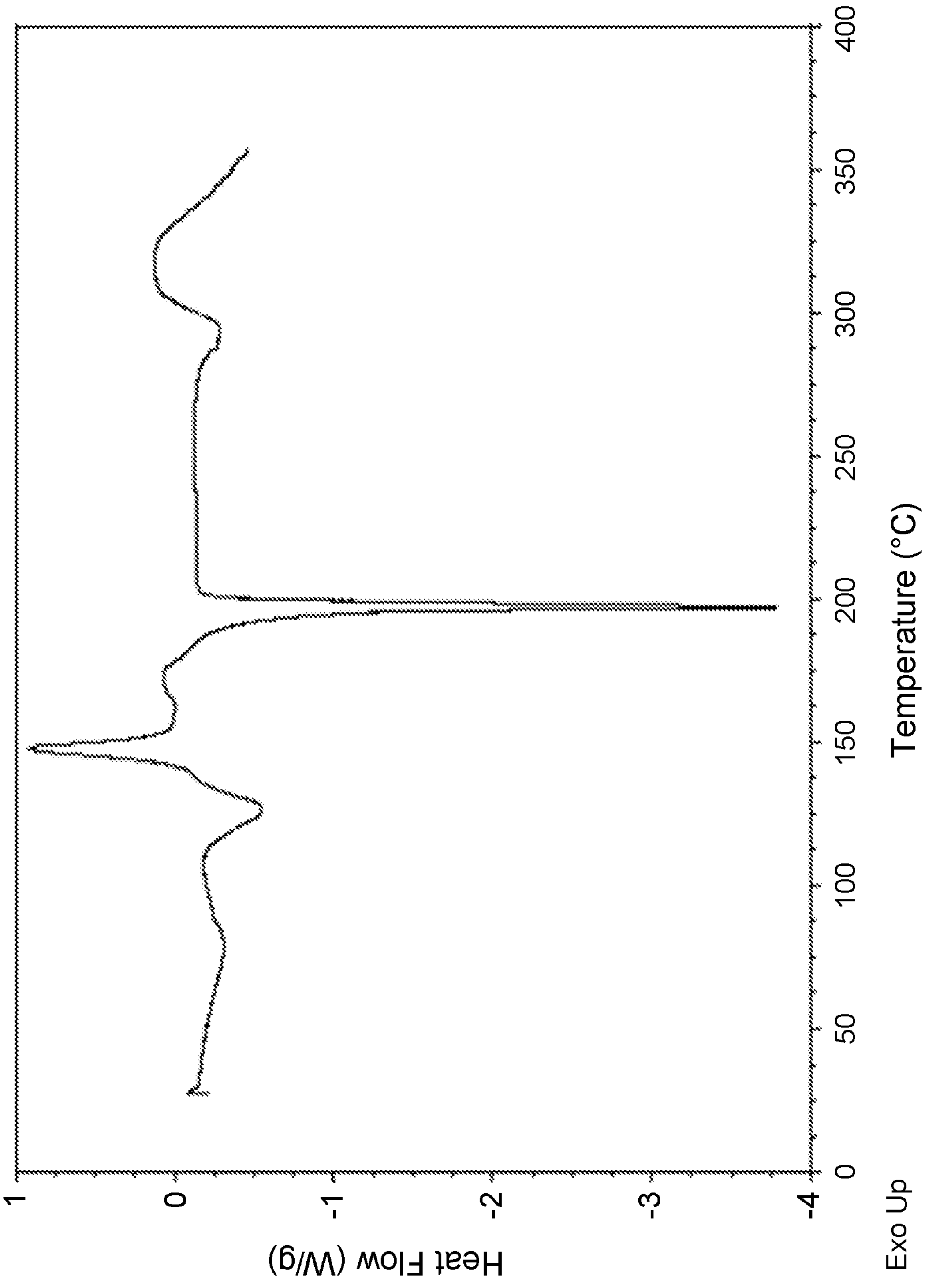
FIG. 6 depicts a DSC curve of Ethanol Solvate Form B of Compound I.

In some embodiments, the ethanol solvate Form B is characterized by a DSC curve substantially similar to that in FIG. 6.

Citric Acid Cocrystal Form A of Compound I

One embodiment of the disclosure provides a citric acid cocrystal Form A of Compound I. In some embodiments, the citric acid cocrystal Form A of Compound I is substantially pure.

In some embodiments, the citric acid cocrystal Form A of Compound I is characterized by an X-ray powder diffractogram having a signal at one or more two-theta values selected from 4.7±0.2, 18.8±0.2, 21.9±0.2, and 23.5±0.2. In some embodiments, the citric acid cocrystal Form A of Compound I is characterized by an X-ray powder diffractogram having a signal at the following two-theta values: 4.7±0.2, 18.8±0.2, 21.9±0.2, and 23.5±0.2. In some embodiments, the citric acid cocrystal Form A of Compound I is characterized by an X-ray powder diffractogram having (a) a signal at the following two-theta values: 4.7±0.2, 18.8±0.2, 21.9±0.2, and 23.5±0.2; and (b) a signal at one or more two-theta values selected from 17.7±0.2, 18.1±0.2, 21.5±0.2, 22.5±0.2, and 27.0±0.2. In some embodiments, the citric acid cocrystal Form A of Compound I is characterized by an X-ray powder diffractogram having signals at the following two-theta values: 4.7±0.2, 17.7±0.2, 18.1±0.2, 18.8±0.2, 21.5±0.2, 21.9±0.2, 22.5±0.2, 23.5±0.2, and 27.0±0.2.

Figure 7:
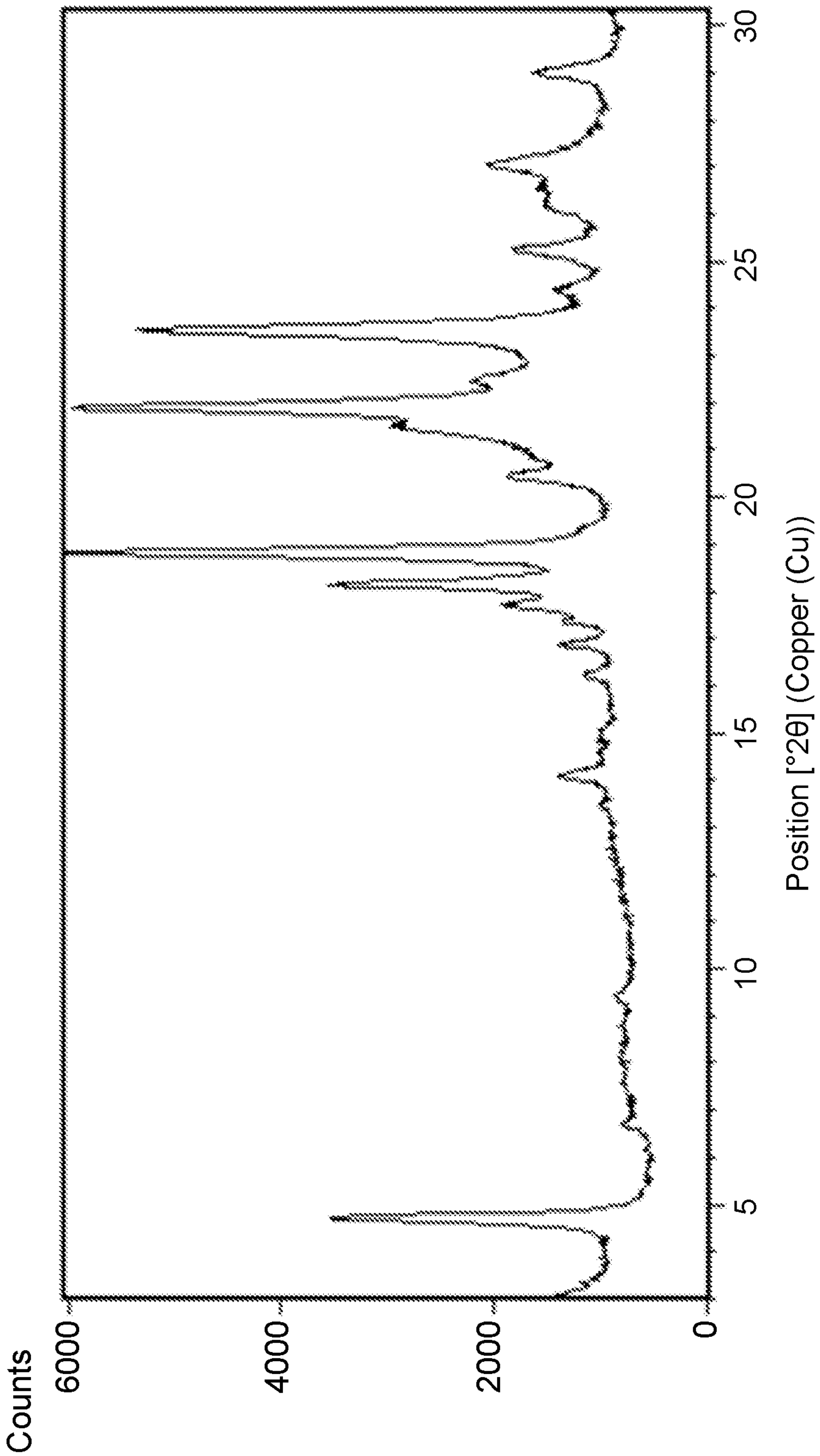
FIG. 7 depicts an XRPD diffractogram of Citric Acid Cocrystal Form A of Compound I.

In some embodiments, the citric acid cocrystal Form A is characterized by an X-ray powder diffractogram substantially similar to that in FIG. 7.

In some embodiments, the citric acid cocrystal Form A is characterized by a TGA thermogram showing a gradual weight loss from ambient temperature until thermal degradation.

Figure 8:
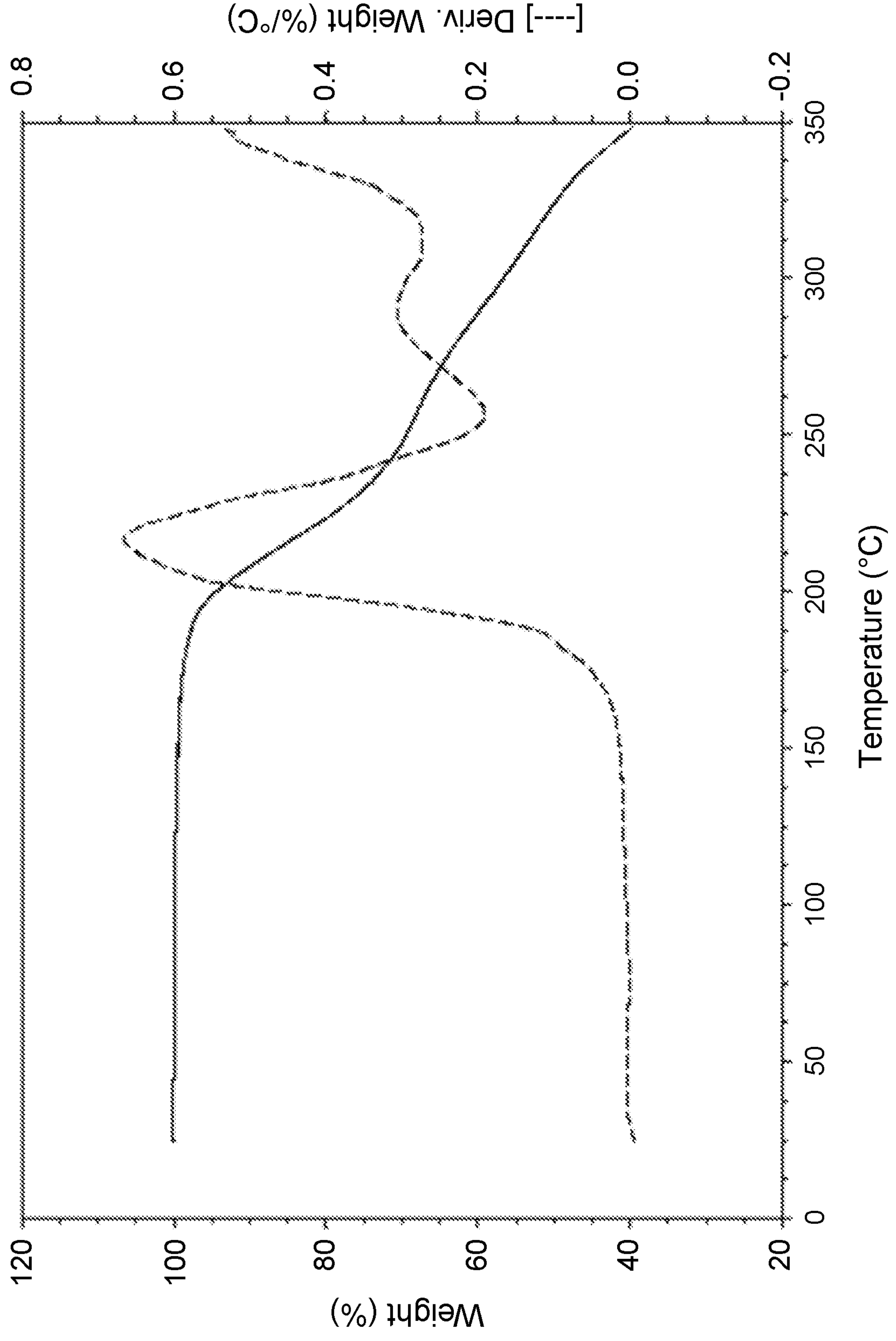
FIG. 8 depicts a TGA thermogram of Citric Acid Cocrystal Form A of Compound I.

In some embodiments, the citric acid cocrystal Form A is characterized by a TGA thermogram substantially similar to that in FIG. 8.

In some embodiments, the citric acid cocrystal Form A is characterized by a DSC curve having an endothermic peak at about 185° C.

Figure 9:
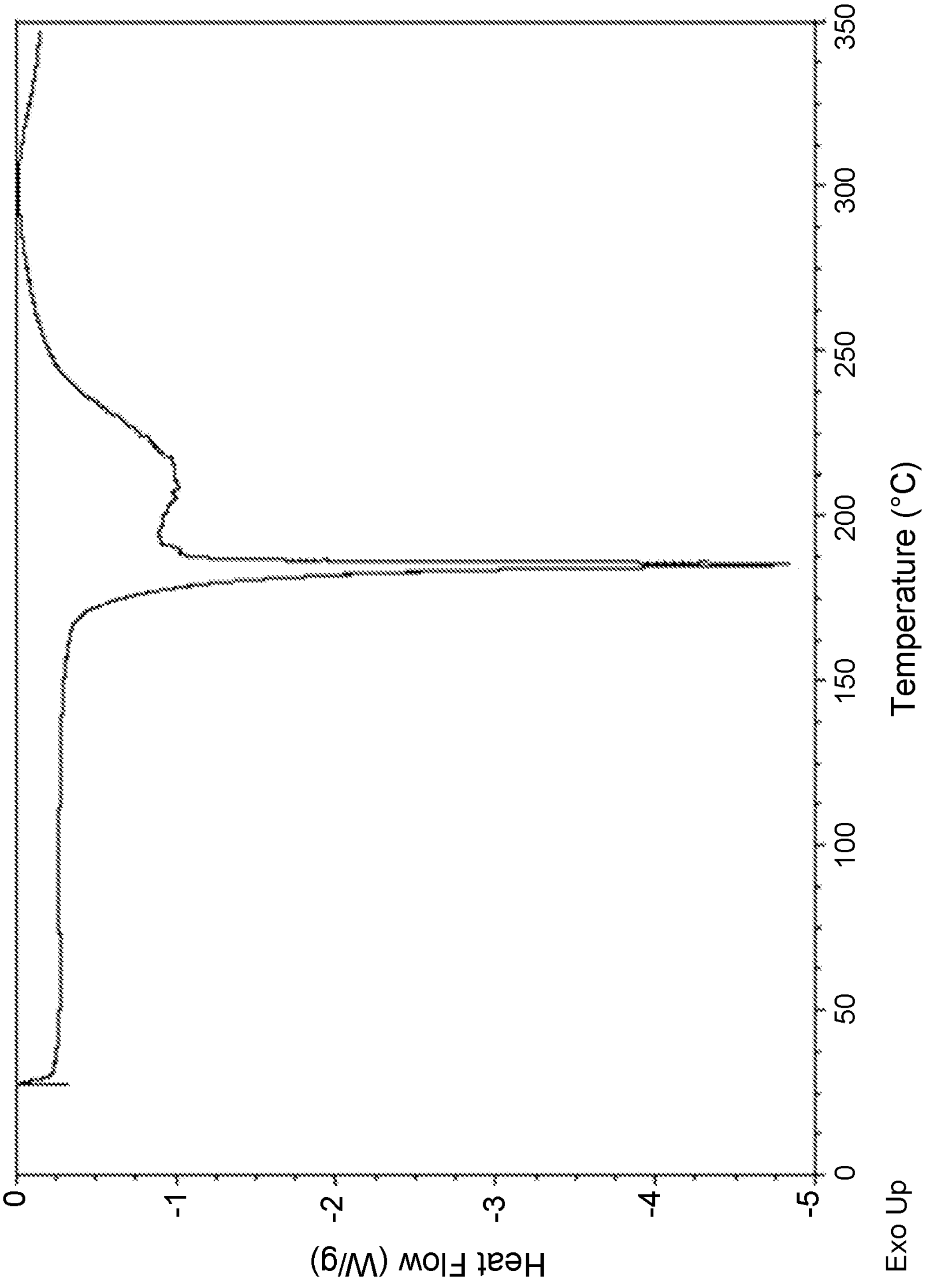
FIG. 9 depicts a DSC curve of Citric Acid Cocrystal Form A of Compound I

In some embodiments, the citric acid cocrystal Form A is characterized by a DSC curve substantially similar to that in FIG. 9.

Form B of Compound I

One embodiment of the disclosure provides Form B of Compound I. In some embodiments, Form B of Compound I is substantially pure.

In some embodiments, Form B of Compound I is characterized by an X-ray powder diffractogram having a signal at 11.8±0.2, 12.2±0.2, and/or 13.5±0.2 two-theta. In some embodiments, Form B of Compound I is characterized by an X-ray powder diffractogram having a signal at 11.8±0.2, 12.2±0.2, and 13.5±0.2 two-theta.

In some embodiments, Form B of Compound I is characterized by an X-ray powder diffractogram having a signal at 11.8±0.2, 12.2±0.2, 13.5±0.2, 19.9±0.2 and/or 23.1±0.2 two-theta. In some embodiments, Form B of Compound I is characterized by an X-ray powder diffractogram having (a) a signal at 11.8±0.2, 12.2±0.2, and/or 13.5±0.2 two-theta; and (b) a signal at 11.3±0.2, 19.9±0.2, and/or 23.1±0.2 two-theta. In some embodiments, Form B of Compound I is characterized by an X-ray powder diffractogram having (a) a signal at the following two-theta values: 11.8±0.2, 12.2±0.2, and 13.5±0.2; and (b) a signal at one or two-theta values selected from 11.3±0.2, 19.9±0.2, and/or 23.1±0.2. In some embodiments, Form B of Compound I is characterized by an X-ray powder diffractogram having (a) a signal at the following two-theta values: 11.8±0.2, 12.2±0.2, and 13.5±0.2; and (b) a signal at two or two-theta values selected from 11.3±0.2, 19.9±0.2, and/or 23.1±0.2.

In some embodiments, Form B of Compound I is characterized by an X-ray powder diffractogram having (a) a signal at 11.8±0.2, 12.2±0.2, 13.5±0.2, 19.9±0.2 and/or 23.1±0.2 two-theta; and (b) a signal at 11.3±0.2 two-theta.

In some embodiments, Form B of Compound I is characterized by an X-ray powder diffractogram having a signal at one or more (such as, e.g., two or more, three or more, four or more, five or more) two-theta values selected from 11.3±0.2, 11.8±0.2, 12.2±0.2, 13.5±0.2, 19.9±0.2, and 23.1±0.2. In some embodiments, Form B of Compound I is characterized by an X-ray powder diffractogram having a signal at the following two-theta values: 11.3±0.2, 11.8±0.2, 12.2±0.2, 13.5±0.2, 19.9±0.2, and 23.1±0.2. In some embodiments, Form B of Compound I is characterized by an X-ray powder diffractogram having (a) a signal at the following two-theta values: 11.3±0.2, 11.8±0.2, 12.2±0.2, 13.5±0.2, 19.9±0.2, and 23.1±0.2; and (b) a signal at one or more two-theta values selected from 11.6±0.2, 17.0±0.2, 22.0±0.2, and 27.1±0.2. In some embodiments, Form B of Compound I is characterized by an X-ray powder diffractogram having signals at the following two-theta values: 11.3±0.2, 11.6±0.2, 11.8±0.2, 12.2±0.2, 13.5±0.2, 17.0±0.2, 19.9±0.2, 22.0±0.2, 23.1±0.2, and 27.1±0.2.

Figure 10:
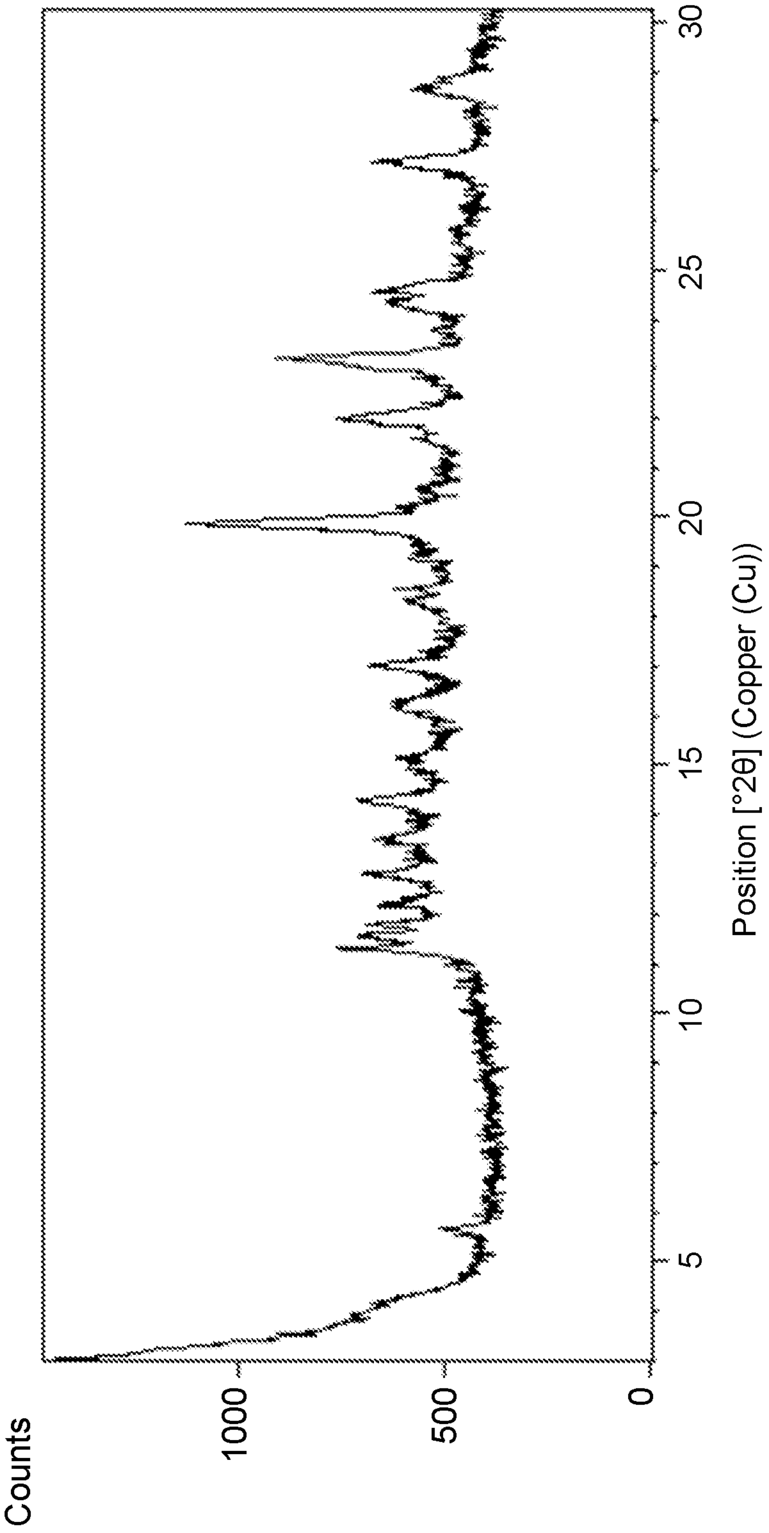
FIG. 10 depicts an XRPD diffractogram of Form B of Compound I.

In some embodiments, Form B is characterized by an X-ray powder diffractogram substantially similar to that in FIG. 10.

In some embodiments, Form B of Compound I is characterized by a $^{13}C$ NMR spectrum having one or more signals selected from 177.0±0.2 ppm, 139.8±0.2 ppm, 131.2±0.2 ppm, 116.1±0.2 ppm, 76.4±0.2 ppm, and 20.9±0.2 ppm. In some embodiments, Form B of Compound I is characterized by a $^{13}C$ NMR spectrum having signals at 177.0±0.2 ppm, 139.8±0.2 ppm, 131.2±0.2 ppm, 116.1±0.2 ppm, 76.4±0.2 ppm, and 20.9±0.2 ppm. In some embodiments, Form B of Compound I is characterized by a $^{13}C$ NMR spectrum having (a) signals at 177.0±0.2 ppm, 139.8±0.2 ppm, 131.2±0.2 ppm, 116.1±0.2 ppm, 76.4±0.2 ppm, and 20.9±0.2 ppm and (b) one or more signals selected from 172.6±0.2 ppm, 132.9±0.2 ppm, 129.2±0.2 ppm, 109.7±0.2 ppm, and 35.5±0.2 ppm. In some embodiments, Form B of Compound I is characterized by a $^{13}C$ NMR spectrum having signals at 177.0±0.2 ppm, 172.6±0.2 ppm, 139.8±0.2 ppm, 132.9±0.2 ppm, 131.2±0.2 ppm, 129.2±0.2 ppm, 116.1±0.2 ppm, 109.7±0.2 ppm, 76.4±0.2 ppm, 35.5±0.2 ppm, and 20.9±0.2 ppm.

Figure 13:
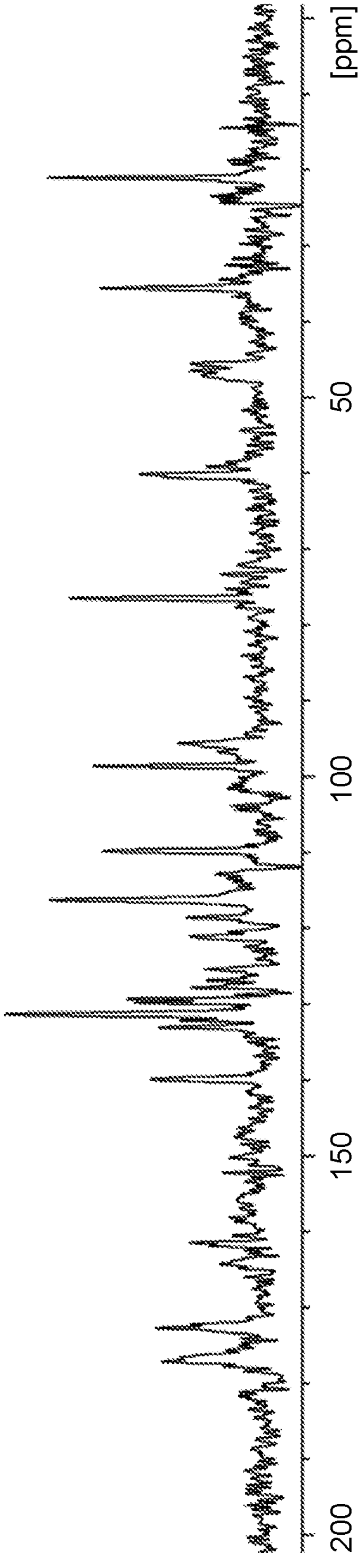
FIG. 13 depicts a solid state $^{13}C$ NMR spectrum of Form B of Compound I.

In some embodiments, Form B is characterized by a $^{13}C$ NMR spectrum substantially similar to that in FIG. 13.

In some embodiments, Form B of Compound I is characterized by a $^{19}F$ NMR spectrum having a signal at one or more ppm values selected from −129.1±0.2 ppm, −128.4±0.2 ppm, −120.6±0.2 ppm, −115.3±0.2 ppm, and −107.9±0.2 ppm. In some embodiments, Form B of Compound I is characterized by a $^{19}F$ NMR spectrum having signals at −129.1±0.2 ppm, −128.4±0.2 ppm, −120.6±0.2 ppm, −115.3±0.2 ppm, and −107.9±0.2 ppm.

Figure 15:
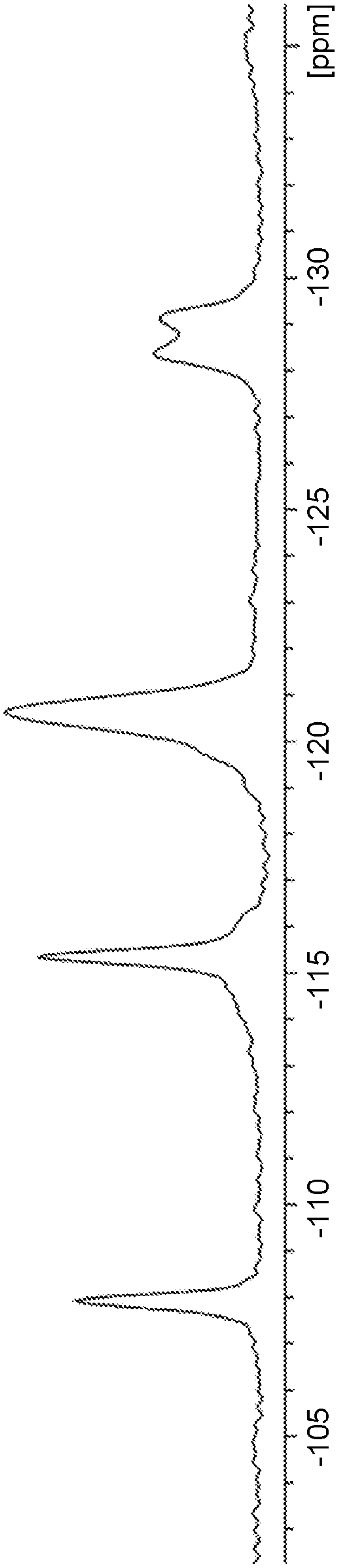
FIG. 15 depicts a solid state $^{19}F$ NMR spectrum of Form B of Compound I.

In some embodiments, Form B is characterized by a $^{19}F$ NMR spectrum substantially similar to that in FIG. 15.

In some embodiments, Form B is characterized by a DSC curve having multiple endothermic and exothermic peaks at about 69° C., about 190° C., and about 195° C.

Figure 11:
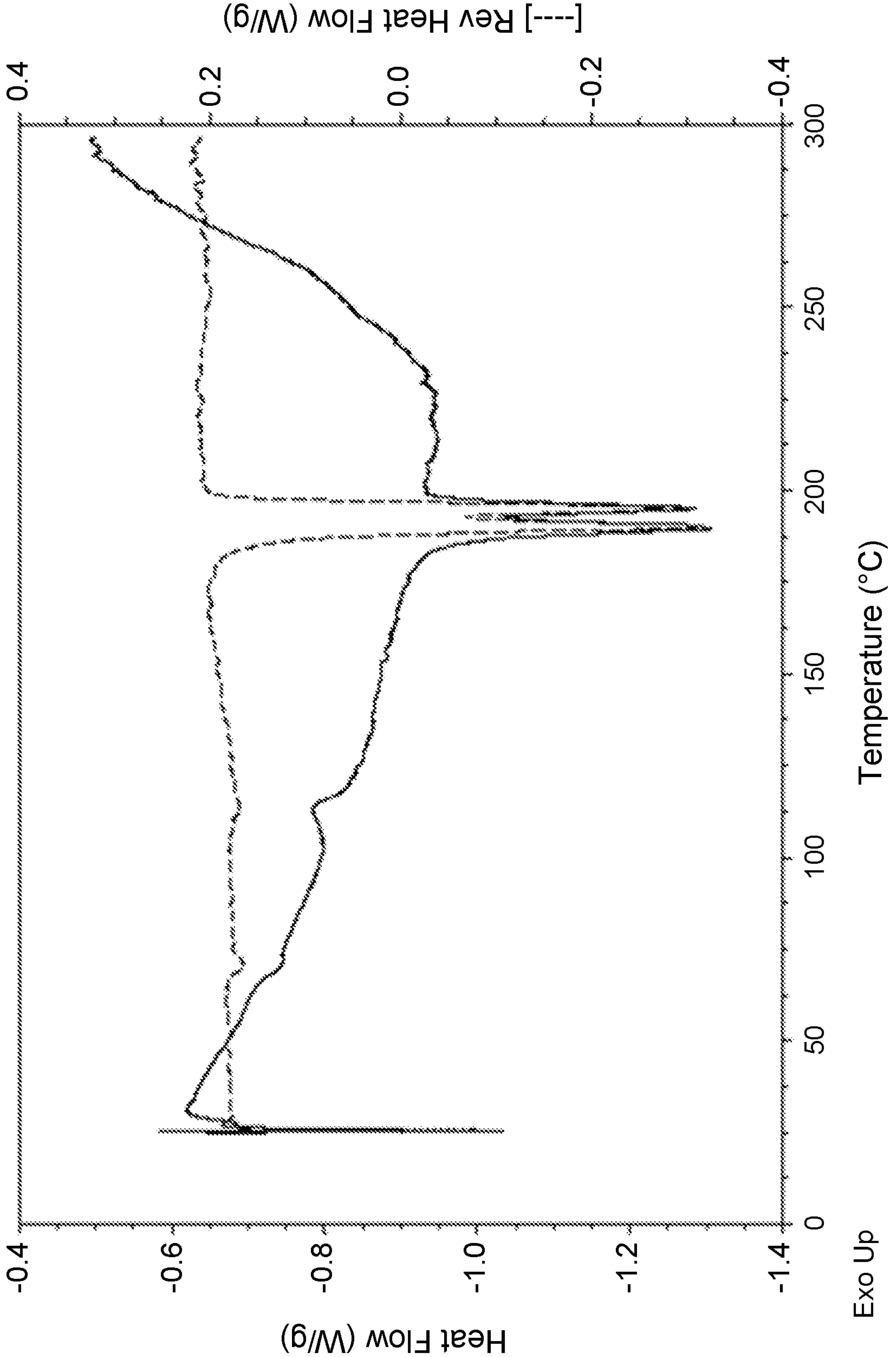
FIG. 11 depicts a DSC curve of Form B of Compound I.

In some embodiments, Form B is characterized by a DSC curve substantially similar to that in FIG. 11.

Another aspect of the disclosure provides pharmaceutical compositions comprising a solid form of Compound I selected from Compound I ethanol solvate Form A, Compound I ethanol solvate Form B, Compound I citric acid cocrystal Form A, and Compound I Form B. In some embodiments, the pharmaceutical composition comprising a solid form of Compound I selected from Compound I ethanol solvate Form A, Compound I ethanol solvate Form B, Compound I citric acid cocrystal Form A, and Compound I Form B is administered to a patient in need thereof. In some embodiments, the solid form of Compound I is selected from Compound I ethanol solvate Form A, Compound I ethanol solvate Form B, and Compound I citric acid cocrystal Form A.

A pharmaceutical composition may further comprise at least one pharmaceutically acceptable carrier. In some embodiments, the at least one pharmaceutically acceptable carrier is selected from pharmaceutically acceptable vehicles and pharmaceutically acceptable adjuvants. In some embodiments, the at least one pharmaceutically acceptable is selected from pharmaceutically acceptable fillers, disintegrants, surfactants, binders, lubricants.

It will also be appreciated that a pharmaceutical composition of this disclosure can be employed in combination therapies; that is, the pharmaceutical compositions described herein can further include at least one additional active therapeutic agent. Alternatively, a pharmaceutical composition comprising a solid form of Compound I selected from Compound I ethanol solvate Form A, Compound I ethanol solvate Form B, Compound I citric acid cocrystal Form A, and Compound I Form B can be administered as a separate composition concurrently with, prior to, or subsequent to, a composition comprising at least one other active therapeutic agent. In some embodiments, a pharmaceutical composition comprising a solid form of Compound I selected from Compound I ethanol solvate Form A, Compound I ethanol solvate Form B, Compound I citric acid cocrystal Form A, and Compound I Form B can be administered as a separate composition concurrently with, prior to, or subsequent to, a composition comprising at least one other active therapeutic agent. In some embodiments, the solid form of Compound I is selected from Compound I ethanol solvate Form A, Compound I ethanol solvate Form B, and Compound I citric acid cocrystal Form A.

As described above, pharmaceutical compositions disclosed herein may optionally further comprise at least one pharmaceutically acceptable carrier. The at least one pharmaceutically acceptable carrier may be selected from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include ion exchangers, alumina, aluminum stearate, lecithin, serum proteins (such as, e.g., human serum albumin), buffer substances (such as, e.g., phosphates, glycine, sorbic acid, and potassium sorbate), partial glyceride mixtures of saturated vegetable fatty acids, water, salts, and electrolytes (such as, e.g., protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as, e.g., lactose, glucose, and sucrose), starches (such as, e.g., corn starch and potato starch), cellulose and its derivatives (such as, e.g., sodium carboxymethyl cellulose, ethyl cellulose, and cellulose acetate), powdered tragacanth, malt, gelatin, talc, excipients (such as, e.g., cocoa butter and suppository waxes), oils (such as, e.g., peanut oil, cottonseed oil, safflower oil, sesame oil, olive oil, corn oil and soybean oil), glycols (such as, e.g., propylene glycol and polyethylene glycol), esters (such as, e.g., ethyl oleate and ethyl laurate), agar, buffering agents (such as, e.g., magnesium hydroxide and aluminum hydroxide), alginic acid, pyrogen-free water, isotonic saline, Ringer's solution, ethyl alcohol, phosphate buffer solutions, non-toxic compatible lubricants (such as, e.g., sodium lauryl sulfate and magnesium stearate), coloring agents, releasing agents, coating agents, sweetening agents, flavoring agents, perfuming agents, preservatives, and antioxidants.

In some embodiments, the solid form of Compound I is a crystalline solid consisting of 1% to 99% ethanol solvate Form A relative to the total weight of the crystalline solid Compound I. In some embodiments, the crystalline solid consists of 2% to 99% ethanol solvate Form A relative to the total weight of the crystalline solid Compound I. In some embodiments, the crystalline solid consists of 5% to 99% ethanol solvate Form A relative to the total weight of the crystalline solid Compound I. In some embodiments, the crystalline solid consists of 10% to 99% ethanol solvate Form A relative to the total weight of the crystalline solid Compound I. In some embodiments, the crystalline solid consists of 15% to 99% ethanol solvate Form A relative to the total weight of the crystalline solid Compound I. In some embodiments, the crystalline solid consists of 20% to 99% ethanol solvate Form A relative to the total weight of the crystalline solid Compound I. In some embodiments, the crystalline solid consists of 25% to 99% ethanol solvate Form A relative to the total weight of the crystalline solid Compound I. In some embodiments, the crystalline solid consists of 30% to 99% ethanol solvate Form A relative to the total weight of the crystalline solid Compound I. In some embodiments, the crystalline solid consists of 35% to 99% ethanol solvate Form A relative to the total weight of the crystalline solid Compound I. In some embodiments, the crystalline solid consists of 45% to 99% ethanol solvate Form A relative to the total weight of the crystalline solid Compound I. In some embodiments, the crystalline solid consists of 50% to 99% ethanol solvate Form A relative to the total weight of the crystalline solid Compound I. In some embodiments, the crystalline solid consists of 55% to 99% ethanol solvate Form A relative to the total weight of the crystalline solid Compound I. In some embodiments, the crystalline solid consists of 60% to 99% ethanol solvate Form A relative to the total weight of the crystalline solid Compound I. In some embodiments, the crystalline solid consists of 65% to 99% ethanol solvate Form A relative to the total weight of the crystalline solid Compound I. In some embodiments, the crystalline solid consists of 70% to 99% ethanol solvate Form A relative to the total weight of the crystalline solid Compound I. In some embodiments, the crystalline solid consists of 75% to 99% ethanol solvate Form A relative to the total weight of the crystalline solid Compound I. In some embodiments, the crystalline solid consists of 80% to 99% ethanol solvate Form A relative to the total weight of the crystalline solid Compound I. In some embodiments, the crystalline solid consists of 85% to 99% ethanol solvate Form A relative to the total weight of the crystalline solid Compound I. In some embodiments, the crystalline solid consists of 90% to 99% ethanol solvate Form A relative to the total weight of the crystalline solid Compound I. In some embodiments, the crystalline solid consists of 95% to 99% ethanol solvate Form A relative to the total weight of the crystalline solid Compound I.

In some embodiments, the solid form of Compound I is a crystalline solid consisting of 1% to 99% ethanol solvate Form B relative to the total weight of the crystalline solid Compound I. In some embodiments, the crystalline solid consists of 2% to 99% ethanol solvate Form B relative to the total weight of the crystalline solid Compound I. In some embodiments, the crystalline solid consists of 5% to 99% ethanol solvate Form B relative to the total weight of the crystalline solid Compound I. In some embodiments, the crystalline solid consists of 10% to 99% ethanol solvate Form B relative to the total weight of the crystalline solid Compound I. In some embodiments, the crystalline solid consists of 15% to 99% ethanol solvate Form B relative to the total weight of the crystalline solid Compound I. In some embodiments, the crystalline solid consists of 20% to 99% ethanol solvate Form B relative to the total weight of the crystalline solid Compound I. In some embodiments, the crystalline solid consists of 25% to 99% ethanol solvate Form B relative to the total weight of the crystalline solid Compound I. In some embodiments, the crystalline solid consists of 30% to 99% ethanol solvate Form B relative to the total weight of the crystalline solid Compound I. In some embodiments, the crystalline solid consists of 35% to 99% ethanol solvate Form B relative to the total weight of the crystalline solid Compound I. In some embodiments, the crystalline solid consists of 45% to 99% ethanol solvate Form B relative to the total weight of the crystalline solid Compound I. In some embodiments, the crystalline solid consists of 50% to 99% ethanol solvate Form B relative to the total weight of the crystalline solid Compound I. In some embodiments, the crystalline solid consists of 55% to 99% ethanol solvate Form B relative to the total weight of the crystalline solid Compound I. In some embodiments, the crystalline solid consists of 60% to 99% ethanol solvate Form B relative to the total weight of the crystalline solid Compound I. In some embodiments, the crystalline solid consists of 65% to 99% ethanol solvate Form B relative to the total weight of the crystalline solid Compound I. In some embodiments, the crystalline solid consists of 70% to 99% ethanol solvate Form B relative to the total weight of the crystalline solid Compound I. In some embodiments, the crystalline solid consists of 75% to 99% ethanol solvate Form B relative to the total weight of the crystalline solid Compound I. In some embodiments, the crystalline solid consists of 80% to 99% ethanol solvate Form B relative to the total weight of the crystalline solid Compound I. In some embodiments, the crystalline solid consists of 85% to 99% ethanol solvate Form B relative to the total weight of the crystalline solid Compound I. In some embodiments, the crystalline solid consists of 90% to 99% ethanol solvate Form B relative to the total weight of the crystalline solid Compound I. In some embodiments, the crystalline solid consists of 95% to 99% ethanol solvate Form B relative to the total weight of the crystalline solid Compound I.

In some embodiments, the solid form of Compound I is a crystalline solid consisting of 1% to 99% citric acid cocrystal Form A relative to the total weight of the crystalline solid Compound I. In some embodiments, the crystalline solid consists of 2% to 99% citric acid cocrystal Form A relative to the total weight of the crystalline solid Compound I. In some embodiments, the crystalline solid consists of 5% to 99% citric acid cocrystal Form A relative to the total weight of the crystalline solid Compound I. In some embodiments, the crystalline solid consists of 10% to 99% citric acid cocrystal Form A relative to the total weight of the crystalline solid Compound I. In some embodiments, the crystalline solid consists of 15% to 99% citric acid cocrystal Form A relative to the total weight of the crystalline solid Compound I. In some embodiments, the crystalline solid consists of 20% to 99% citric acid cocrystal Form A relative to the total weight of the crystalline solid Compound I. In some embodiments, the crystalline solid consists of 25% to 99% citric acid cocrystal Form A relative to the total weight of the crystalline solid Compound I. In some embodiments, the crystalline solid consists of 30% to 99% citric acid cocrystal Form A relative to the total weight of the crystalline solid Compound I. In some embodiments, the crystalline solid consists of 35% to 99% citric acid cocrystal Form A relative to the total weight of the crystalline solid Compound I. In some embodiments, the crystalline solid consists of 45% to 99% citric acid cocrystal Form A relative to the total weight of the crystalline solid Compound I. In some embodiments, the crystalline solid consists of 50% to 99% citric acid cocrystal Form A relative to the total weight of the crystalline solid Compound I. In some embodiments, the crystalline solid consists of 55% to 99% citric acid cocrystal Form A relative to the total weight of the crystalline solid Compound I. In some embodiments, the crystalline solid consists of 60% to 99% citric acid cocrystal Form A relative to the total weight of the crystalline solid Compound I. In some embodiments, the crystalline solid consists of 65% to 99% citric acid cocrystal Form A relative to the total weight of the crystalline solid Compound I. In some embodiments, the crystalline solid consists of 70% to 99% citric acid cocrystal Form A relative to the total weight of the crystalline solid Compound I. In some embodiments, the crystalline solid consists of 75% to 99% citric acid cocrystal Form A relative to the total weight of the crystalline solid Compound I. In some embodiments, the crystalline solid consists of 80% to 99% citric acid cocrystal Form A relative to the total weight of the crystalline solid Compound I. In some embodiments, the crystalline solid consists of 85% to 99% citric acid cocrystal Form A relative to the total weight of the crystalline solid Compound I. In some embodiments, the crystalline solid consists of 90% to 99% citric acid cocrystal Form A relative to the total weight of the crystalline solid Compound I. In some embodiments, the crystalline solid consists of 95% to 99% citric acid cocrystal Form A relative to the total weight of the crystalline solid Compound I.

In some embodiments, the solid form of Compound I is a crystalline solid consisting of 1% to 99% Form B relative to the total weight of the crystalline solid Compound I. In some embodiments, the crystalline solid consists of 2% to 99% Form B relative to the total weight of the crystalline solid Compound I. In some embodiments, the crystalline solid consists of 5% to 99% Form B relative to the total weight of the crystalline solid Compound I. In some embodiments, the crystalline solid consists of 10% to 99% Form B relative to the total weight of the crystalline solid Compound I. In some embodiments, the crystalline solid consists of 15% to 99% Form B relative to the total weight of the crystalline solid Compound I. In some embodiments, the crystalline solid consists of 20% to 99% Form B relative to the total weight of the crystalline solid Compound I. In some embodiments, the crystalline solid consists of 25% to 99% Form B relative to the total weight of the crystalline solid Compound I. In some embodiments, the crystalline solid consists of 30% to 99% Form B relative to the total weight of the crystalline solid Compound I. In some embodiments, the crystalline solid consists of 35% to 99% Form B relative to the total weight of the crystalline solid Compound I. In some embodiments, the crystalline solid consists of 45% to 99% Form B relative to the total weight of the crystalline solid Compound I. In some embodiments, the crystalline solid consists of 50% to 99% Form B relative to the total weight of the crystalline solid Compound I. In some embodiments, the crystalline solid consists of 55% to 99% Form B relative to the total weight of the crystalline solid Compound I. In some embodiments, the crystalline solid consists of 60% to 99% Form B relative to the total weight of the crystalline solid Compound I. In some embodiments, the crystalline solid consists of 65% to 99% Form B relative to the total weight of the crystalline solid Compound I. In some embodiments, the crystalline solid consists of 70% to 99% Form B relative to the total weight of the crystalline solid Compound I. In some embodiments, the crystalline solid consists of 75% to 99% Form B relative to the total weight of the crystalline solid Compound I. In some embodiments, the crystalline solid consists of 80% to 99% Form B relative to the total weight of the crystalline solid Compound I. In some embodiments, the crystalline solid consists of 85% to 99% Form B relative to the total weight of the crystalline solid Compound I. In some embodiments, the crystalline solid consists of 90% to 99% Form B relative to the total weight of the crystalline solid Compound I. In some embodiments, the crystalline solid consists of 95% to 99% Form B relative to the total weight of the crystalline solid Compound I.

In some embodiments of the disclosure, a solid form of Compound I selected from Compound I ethanol solvate Form A, Compound I ethanol solvate Form B, Compound I citric acid cocrystal Form A, and Compound I Form B (such as, e.g., a solid form of Compound I selected from Compound I ethanol solvate Form A, Compound I ethanol solvate Form B, and Compound I citric acid cocrystal Form A) is used APOL1 mediated kidney disease. In some embodiments, the APOL1 mediated kidney disease is selected from ESKD, FSGS, HIV-associated nephropathy, NDKD, arterionephrosclerosis, lupus nephritis, microalbuminuria, and chronic kidney disease. In some embodiments, the APOL1 mediated kidney disease treated with a solid form of Compound I selected from Compound I ethanol solvate Form A, Compound I ethanol solvate Form B, Compound I citric acid cocrystal Form A, and Compound I Form B is FSGS. In some embodiments, the APOL1 mediated kidney disease treated with a solid form of Compound I selected from Compound I ethanol solvate Form A, Compound I ethanol solvate Form B, Compound I citric acid cocrystal Form A, and Compound I Form B is NDKD. In some embodiments, the APOL1 mediated kidney disease treated with a solid form of Compound I selected from Compound I ethanol solvate Form A, Compound I ethanol solvate Form B, Compound I citric acid cocrystal Form A, and Compound I Form B is ESKD. In some embodiments, the patient with APOL1 mediated kidney disease to be treated with a solid form of Compound I selected from Compound I ethanol solvate Form A, Compound I ethanol solvate Form B, Compound I citric acid cocrystal Form A, and Compound I Form B has two APOL1 risk alleles. In some embodiments, the patient with APOL1 mediated kidney disease is homozygous for APOL1 genetic risk alleles G1: S342G:I384M. In some embodiments, the patient with APOL1 mediated kidney disease is homozygous for APOL1 genetic risk alleles G2: N388del:Y389del. In some embodiments, the patient with APOL1 mediated kidney disease is heterozygous for APOL1 genetic risk alleles G1: S342G: I384M and G2: N388del:Y389del.

In some embodiments, the methods of the disclosure comprise administering a solid form of Compound I selected from Compound I ethanol solvate Form A, Compound I ethanol solvate Form B, Compound I citric acid cocrystal Form A, and Compound I Form B (such as, e.g., a solid form of Compound I selected from Compound I ethanol solvate Form A, Compound I ethanol solvate Form B, and Compound I citric acid cocrystal Form A) to a patient in need thereof. In some embodiments, said patient in need thereof possesses APOL1 genetic variants, i.e., G1: S342G:I384M and G2: N388del:Y389del.

Another aspect of the disclosure provides methods of inhibiting APOL1 activity comprising contacting said APOL1 with a solid form of Compound I selected from Compound I ethanol solvate Form A, Compound I ethanol solvate Form B, Compound I citric acid cocrystal Form A, and Compound I Form B. In some embodiments, the solid form of Compound I is selected from Compound I ethanol solvate Form A, Compound I ethanol solvate Form B, Compound I citric acid cocrystal Form A. In some embodiments, the solid form of Compound I is Form B of Compound I.

NON-LIMITING EXEMPLARY EMBODIMENTS

Without limitation, some embodiments of this disclosure include:

1. Ethanol solvate Form A of Compound I.
2. Ethanol solvate Form A of Compound I according to Embodiment 1, characterized by an X-ray powder diffractogram having a signal at 14.4±0.2 and/or 21.5±0.2 two-theta.
3. Ethanol solvate Form A of Compound I according to Embodiment 1 or 2, characterized by an X-ray powder diffractogram having (a) a signal at 14.4±0.2 and/or 21.5±0.2 two-theta; and (b) a signal at 23.5±0.2 and/or 24.8±0.2 two-theta.
4. Ethanol solvate Form A of Compound I according to any one of Embodiments 1-3, characterized by an X-ray powder diffractogram having a signal at three or more two-theta values selected from 14.4±0.2, 21.5±0.2, 23.5±0.2, and 24.8±0.2.
5. Ethanol solvate Form A of Compound I according to any one of Embodiments 1-4, characterized by an X-ray powder diffractogram having signals at 14.4±0.2, 21.5±0.2, 23.5±0.2, and 24.8±0.2 two-theta.
6. Ethanol solvate Form A of Compound I according to any one of Embodiments 1-5, characterized by an X-ray powder diffractogram having (a) a signal at the following two-theta values: 14.4±0.2, 21.5±0.2, 23.5±0.2, and 24.8±0.2; and (b) a signal at one or more two-theta values selected from 14.7±0.2, 14.8±0.2, 18.1±0.2, and 24.4±0.2.
7. Ethanol solvate Form A of Compound I according to any one of Embodiments 1-6, characterized by an X-ray powder diffractogram having (a) a signal at the following two-theta values: 14.4±0.2, 21.5±0.2, 23.5±0.2, and 24.8±0.2; and (b) a signal at two or more two-theta values selected from 14.7±0.2, 14.8±0.2, 18.1±0.2, and 24.4±0.2.
8. Ethanol solvate Form A of Compound I according to any one of Embodiments 1-7, characterized by an X-ray powder diffractogram having (a) a signal at the following two-theta values: 14.4±0.2, 21.5±0.2, 23.5±0.2, and 24.8±0.2; and (b) a signal at three or more two-theta values selected from 14.7±0.2, 14.8±0.2, 18.1±0.2, and 24.4±0.2.
9. Ethanol solvate Form A of Compound I according to any one of Embodiments 1-8, characterized by an X-ray powder diffractogram having signals at 14.4±0.2, 14.7±0.2, 14.8±0.2, 18.1±0.2, 21.5±0.2, 23.5±0.2, 24.4±0.2, and 24.8±0.2 two-theta.
10. Ethanol solvate Form A of Compound I according to Embodiment 1, characterized by an X-ray powder diffractogram substantially similar to that in FIG. 1.
11. Ethanol solvate Form A of Compound I according to any one of Embodiments 1-10, characterized by a $^{13}C$ NMR spectrum having one or more signals selected from 18.0±0.2 ppm, 57.5±0.2 ppm, 58.0±0.2 ppm, 116.7±0.2 ppm, and 128.0±0.2 ppm.
12. Ethanol solvate Form A of Compound I according to any one of Embodiments 1-11, characterized by a $^{13}C$ NMR spectrum having two or more signals selected from 18.0±0.2 ppm, 57.5±0.2 ppm, 58.0±0.2 ppm, 116.7±0.2 ppm, and 128.0±0.2 ppm.
13. Ethanol solvate Form A of Compound I according to any one of Embodiments 1-12, characterized by a $^{13}C$ NMR spectrum having three or more signals selected from 18.0±0.2 ppm, 57.5±0.2 ppm, 58.0±0.2 ppm, 116.7±0.2 ppm, and 128.0±0.2 ppm.
14. Ethanol solvate Form A of Compound I according to any one of Embodiments 1-13, characterized by a $^{13}C$ NMR spectrum signals at 18.0±0.2 ppm, 57.5±0.2 ppm, 58.0±0.2 ppm, 116.7±0.2 ppm, and 128.0±0.2 ppm.
15. Ethanol solvate Form A of Compound I according to any one of Embodiments 1-14, characterized by a $^{13}C$ NMR spectrum having (a) signals at 18.0±0.2 ppm, 57.5±0.2 ppm, 58.0±0.2 ppm, 116.7±0.2 ppm, and 128.0±0.2 ppm and (b) one or more signals selected from 18.9±0.2 ppm, 112.4±0.2 ppm, 120.6±0.2 ppm, 126.4±0.2 ppm, and 131.2±0.2 ppm.
16. Ethanol solvate Form A of Compound I according to any one of Embodiments 1-15, characterized by a $^{13}C$ NMR spectrum having (a) signals at 18.0±0.2 ppm, 57.5±0.2 ppm, 58.0±0.2 ppm, 116.7±0.2 ppm, and 128.0±0.2 ppm and (b) two or more signals selected from 18.9±0.2 ppm, 112.4±0.2 ppm, 120.6±0.2 ppm, 126.4±0.2 ppm, and 131.2±0.2 ppm.
17. Ethanol solvate Form A of Compound I according to any one of Embodiments 1-16, characterized by a $^{13}C$ NMR spectrum having (a) signals at 18.0±0.2 ppm, 57.5±0.2 ppm, 58.0±0.2 ppm, 116.7±0.2 ppm, and 128.0±0.2 ppm and (b) three or more signals selected from 18.9±0.2 ppm, 112.4±0.2 ppm, 120.6±0.2 ppm, 126.4±0.2 ppm, and 131.2±0.2 ppm.
18. Ethanol solvate Form A of Compound I according to any one of Embodiments 1-17, characterized by a $^{13}C$ NMR spectrum having signals at 18.0±0.2 ppm, 18.9±0.2 ppm, 57.5±0.2 ppm, 58.0±0.2 ppm, 112.4±0.2 ppm, 116.7±0.2 ppm, 120.6±0.2 ppm, 126.4±0.2 ppm, 128.0±0.2 and 131.2±0.2 ppm.
19. Ethanol solvate Form A of Compound I according to Embodiment 1, characterized by a $^{13}C$ NMR spectrum substantially similar to that in FIG. 2.
20. Ethanol solvate Form A of Compound I according to any one of Embodiments 1-19, characterized by a $^{19}F$ NMR spectrum having a signal at one or more ppm values selected from −136.0±0.2 ppm, −131.2±0.2 ppm, −126.0±0.2 ppm, −122.9±0.2 ppm, −113.0±0.2 ppm, and −111.5±0.2 ppm.
21. Ethanol solvate Form A of Compound I according to any one of Embodiments 1-20, characterized by a $^{19}F$ NMR spectrum having a signal at two or more ppm values selected from −136.0±0.2 ppm, −131.2±0.2 ppm, −126.0±0.2 ppm, −122.9±0.2 ppm, −113.0±0.2 ppm, and −111.5±0.2 ppm.
22. Ethanol solvate Form A of Compound I according to any one of Embodiments 1-21, characterized by a $^{19}F$ NMR spectrum having a signal at three or more ppm values selected from −136.0±0.2 ppm, −131.2±0.2 ppm, −126.0±0.2 ppm, −122.9±0.2 ppm, −113.0±0.2 ppm, and −111.5±0.2 ppm.

23. Ethanol solvate Form A of Compound I according to any one of Embodiments 1-22, characterized by a $^{19}F$ NMR spectrum having a signal at four or more ppm values selected from −136.0±0.2 ppm, −131.2±0.2 ppm, −126.0±0.2 ppm, −122.9±0.2 ppm, −113.0±0.2 ppm, and −111.5±0.2 ppm.
24. Ethanol solvate Form A of Compound I according to any one of Embodiments 1-23, characterized by a $^{19}F$ NMR spectrum having signals at −136.0±0.2 ppm, −131.2±0.2 ppm, −126.0±0.2 ppm, −122.9±0.2 ppm, −113.0±0.2 ppm, and −111.5±0.2 ppm.
25. Ethanol solvate Form A of Compound I according to Embodiment 1, characterized by a $^{19}F$ NMR spectrum substantially similar to that in FIG. 3.
26. A pharmaceutical composition comprising ethanol solvate Form A of Compound I according to any one of Embodiments 1-25 and a pharmaceutically acceptable carrier.
27. A method of treating APOL1 mediated kidney disease comprising administering to a patient in need thereof ethanol solvate Form A of Compound I according to any one of Embodiments 1-25 or a pharmaceutical composition according to Embodiment 26.
28. The method according to Embodiment 27, wherein the APOL1 mediated kidney disease is selected from ESKD, NDKD, FSGS, HIV-associated nephropathy, arterionephrosclerosis, lupus nephritis, microalbuminuria, and chronic kidney disease.
29. The method according to Embodiment 27 or 28, wherein the APOL1 mediated kidney disease is FSGS or NDKD.
30. The method according to any one of Embodiments 27-29, wherein the APOL1 mediated kidney disease is associated with APOL1 genetic alleles selected from homozygous G1: S342G:I384M and homozygous G2: N388del:Y389del.
31. The method according to any one of Embodiments 27-29, wherein the APOL1 mediated kidney disease is associated with compound heterozygous G1: S342G: I384M and G2: N388del:Y389del APOL1 genetic alleles.
32. A method of inhibiting APOL1 activity comprising contacting said APOL1 with ethanol solvate Form A of Compound I according to any one of Embodiments 1-25 or a pharmaceutical composition according to Embodiment 26.
33. The method according to Embodiment 32, wherein the APOL1 is associated with APOL1 genetic alleles selected from homozygous G1: S342G:I384M and homozygous G2: N388del:Y389del.
34. The method according to Embodiment 32, wherein the APOL1 is associated with compound heterozygous G1: S342G:I384M and G2: N388del:Y389del APOL1 genetic alleles.
35. Use of ethanol solvate Form A of Compound I according to any one of Embodiments 1-25 in the manufacture of a medicament for treating APOL1 mediated kidney disease.
36. Ethanol solvate Form A of Compound I according to any one of Embodiments 1-25 for use in treating APOL1 mediated kidney disease.
37. A method of preparing ethanol solvate Form A of Compound I comprising:
mixing Compound I Form A with anhydrous ethanol;
cooling to 5° C. and stirring for about 2 weeks; and
isolating ethanol solvate Form A of Compound I.
38. Ethanol solvate Form B of Compound I.
39. Ethanol solvate Form B of Compound I according to Embodiment 38, characterized by an X-ray powder diffractogram having a signal at 11.4±0.2 and/or 15.3±0.2 two-theta.
40. Ethanol solvate Form B of Compound I according to Embodiment 38 or 39, characterized by an X-ray powder diffractogram having (a) a signal at 11.4±0.2 and/or 15.3±0.2 two-theta; and (b) a signal at 19.5±0.2 two-theta.
41. Ethanol solvate Form B of Compound I according to any one of Embodiments 38-40, characterized by an X-ray powder diffractogram having a signal at two or more two-theta values selected from 11.4±0.2, 15.3±0.2, and 19.5±0.2.
42. Ethanol solvate Form B of Compound I according to any one of Embodiments 38-41, characterized by an X-ray powder diffractogram having signals at 11.4±0.2, 15.3±0.2, and 19.5±0.2 two-theta.
43. Ethanol solvate Form B of Compound I according to any one of Embodiments 38-42, characterized by an X-ray powder diffractogram having (a) a signal at the following two-theta values: 11.4±0.2, 15.3±0.2, and 19.5±0.2; and (b) a signal at one or more two-theta values selected from 7.6±0.2, 15.1±0.2, 15.6±0.2, and 24.0±0.2.
44. Ethanol solvate Form B of Compound I according to any one of Embodiments 38-43, characterized by an X-ray powder diffractogram having (a) a signal at the following two-theta values: 11.4±0.2, 15.3±0.2, and 19.5±0.2; and (b) a signal at two or more two-theta values selected from 7.6±0.2, 15.1±0.2, 15.6±0.2, and 24.0±0.2.
45. Ethanol solvate Form B of Compound I according to any one of Embodiments 38-44, characterized by an X-ray powder diffractogram having (a) a signal at the following two-theta values: 11.4±0.2, 15.3±0.2, and 19.5±0.2; and (b) a signal at three or more two-theta values selected from 7.6±0.2, 15.1±0.2, 15.6±0.2, and 24.0±0.2.
46. Ethanol solvate Form B of Compound I according to any one of Embodiments 38-45, characterized by an X-ray powder diffractogram having signals at 7.6±0.2, 11.4±0.2, 15.1±0.2, 15.3±0.2, 15.6±0.2, 19.5±0.2, and 24.0±0.2 two-theta.
47. Ethanol solvate Form B of Compound I according to Embodiment 38, characterized by an X-ray powder diffractogram substantially similar to that in FIG. 4.
48. Ethanol solvate Form B of Compound I according to any one of Embodiments 38-47, characterized by a DSC curve substantially similar to that in FIG. 6.
49. Ethanol solvate Form B of Compound I according to any one of Embodiments 38-47, characterized by a DSC curve having multiple endothermic and exothermic peaks at about 78° C., about 128° C., about 148° C., and/or about 197° C.
50. Ethanol solvate Form B of Compound I according to any one of Embodiments 38-49, characterized by a TGA thermogram substantially similar to that in FIG. 5.
51. Ethanol solvate Form B of Compound I according to any one of Embodiments 38-49, characterized by a TGA thermogram showing multiple weight loss from ambient temperature to 135° C. of about 3%.
52. A pharmaceutical composition comprising ethanol solvate Form B of Compound I according to any one of Embodiments 38-51 and a pharmaceutically acceptable carrier.

53. A method of treating APOL1 mediated kidney disease comprising administering to a patient in need thereof ethanol solvate Form B of Compound I according to any one of Embodiments 38-51 or a pharmaceutical composition according to Embodiment 52.
54. The method according to Embodiment 53, the APOL1 mediated kidney disease is selected from ESKD, NDKD, FSGS, HIV-associated nephropathy, arterionephrosclerosis, lupus nephritis, microalbuminuria, and chronic kidney disease.
55. The method according to Embodiment 53 or 54, the APOL1 mediated kidney disease is FSGS or NDKD.
56. The method according to any one of Embodiments 53-55, wherein the APOL1 mediated kidney disease is associated with APOL1 genetic alleles selected from homozygous G1: S342G:I384M and homozygous G2: N388del:Y389del.
57. The method according to any one of Embodiments 53-55, wherein the APOL1 mediated kidney disease is associated with compound heterozygous G1: S342G: I384M and G2: N388del:Y389del APOL1 genetic alleles.
58. A method of inhibiting APOL1 activity comprising contacting said APOL1 with ethanol solvate Form B of Compound I according to any one of Embodiments 38-51 or a pharmaceutical composition according to Embodiment 52.
59. The method according to Embodiment 58, wherein the APOL1 is associated with APOL1 genetic alleles selected from homozygous G1: S342G:I384M and homozygous G2: N388del:Y389del.
60. The method according to Embodiment 58, wherein the APOL1 is associated with compound heterozygous G1: S342G:I384M and G2: N388del:Y389del APOL1 genetic alleles.
61. Use of ethanol solvate Form B of Compound I according to any one of Embodiments 38-51 in the manufacture of a medicament for treating APOL1 mediated kidney disease.
62. Ethanol solvate Form B of Compound I according to any one of Embodiments 38-51 for use in treating APOL1 mediated kidney disease.
63. A method of preparing ethanol solvate Form B of Compound I comprising:
mixing Compound I Form A with anhydrous ethanol;
cooling to 5° C. and stirring for about 2 weeks;
isolating the wet cake;
drying under vacuum at 45° C.; and
isolating ethanol solvate Form B of Compound I.
64. Citric acid cocrystal Form A of Compound I.
65. Citric acid cocrystal Form A of Compound I according to Embodiment 64, characterized by an X-ray powder diffractogram having a signal at one or more two-theta values selected from 4.7±0.2, 18.8±0.2, 21.9±0.2, and 23.5±0.2.
66. Citric acid cocrystal Form A of Compound I according to Embodiment 64 or 65, characterized by an X-ray powder diffractogram having a signal at two or more two-theta values selected from 4.7±0.2, 18.8±0.2, 21.9±0.2, and 23.5±0.2.
67. Citric acid cocrystal Form A of Compound I according to any one of Embodiments 64-66, characterized by an X-ray powder diffractogram having a signal at three or more two-theta values selected from 4.7±0.2, 18.8±0.2, 21.9±0.2, and 23.5±0.2.
68. Citric acid cocrystal Form A of Compound I according to any one of Embodiments 64-67, characterized by an X-ray powder diffractogram having signals at 4.7±0.2, 18.8±0.2, 21.9±0.2, and 23.5±0.2 two-theta.
69. Citric acid cocrystal Form A of Compound I according to any one of Embodiments 64-68, characterized by an X-ray powder diffractogram having (a) a signal at the following two-theta values: 4.7±0.2, 18.8±0.2, 21.9±0.2, and 23.5±0.2; and (b) a signal at one or more two-theta values selected from 17.7±0.2, 18.1±0.2, 21.5±0.2, 22.5±0.2, and 27.0±0.2.
70. Citric acid cocrystal Form A of Compound I according to any one of Embodiments 64-69, characterized by an X-ray powder diffractogram having (a) a signal at the following two-theta values: 4.7±0.2, 18.8±0.2, 21.9±0.2, and 23.5±0.2; and (b) a signal at two or more two-theta values selected from 17.7±0.2, 18.1±0.2, 21.5±0.2, 22.5±0.2, and 27.0±0.2.
71. Citric acid cocrystal Form A of Compound I according to any one of Embodiments 64-70, characterized by an X-ray powder diffractogram having (a) a signal at the following two-theta values: 4.7±0.2, 18.8±0.2, 21.9±0.2, and 23.5±0.2; and (b) a signal at three or more two-theta values selected from 17.7±0.2, 18.1±0.2, 21.5±0.2, 22.5±0.2, and 27.0±0.2.
72. Citric acid cocrystal Form A of Compound I according to any one of Embodiments 64-70, characterized by an X-ray powder diffractogram having signals at 4.7±0.2, 17.7±0.2, 18.1±0.2, 18.8±0.2, 21.5±0.2, 21.9±0.2, 22.5±0.2, 23.5±0.2, and 27.0±0.2 two-theta.
73. Citric acid cocrystal Form A of Compound I according to Embodiment 64, characterized by an X-ray powder diffractogram substantially similar to that in FIG. 7.
74. Citric acid cocrystal Form A of Compound I according to any one of Embodiments 64-73, characterized by a DSC curve substantially similar to that in FIG. 9.
75. Citric acid cocrystal Form A of Compound I according to any one of Embodiments 64-73, characterized by a DSC curve having an endothermic peak at about 185° C.
76. Citric acid cocrystal Form A of Compound I according to any one of Embodiments 64-75, characterized by a TGA thermogram substantially similar to that in FIG. 8.
77. Citric acid cocrystal Form A of Compound I according to any one of Embodiments 64-75, characterized by a TGA thermogram showing a gradual weight loss from ambient temperature until thermal degradation.
78. A pharmaceutical composition comprising citric acid cocrystal Form A of Compound I according to any one of Embodiments 64-77 and a pharmaceutically acceptable carrier.
79. A method of treating APOL1 mediated kidney disease comprising administering to a patient in need thereof citric acid cocrystal Form A of Compound I according to any one of Embodiments 64-77 or a pharmaceutical composition according to Embodiment 78.
80. The method according to Embodiment 79, wherein the APOL1 mediated kidney disease is selected from ESKD, NDKD, FSGS, HIV-associated nephropathy, arterionephrosclerosis, lupus nephritis, microalbuminuria, and chronic kidney disease.
81. The method according to Embodiment 79 or 80, wherein the APOL1 mediated kidney disease is FSGS or NDKD.
82. The method according to any one of Embodiments 79-81, wherein the APOL1 mediated kidney is associated with APOL1 genetic alleles selected from homozygous G1: S342G:I384M and homozygous G2: N388del:Y389del.

83. The method according to any one of Embodiments 79-81, wherein the APOL1 mediated kidney disease is associated with compound heterozygous G1: S342G: I384M and G2: N388del:Y389del APOL1 genetic alleles.
84. A method of inhibiting APOL1 activity comprising contacting said APOL1 with citric acid cocrystal Form A of Compound I according to any one of Embodiments 64-77 or a pharmaceutical composition according to Embodiment 78.
85. The method according to Embodiment 84, wherein the APOL1 is associated with APOL1 genetic alleles selected from homozygous G1: S342G:I384M and homozygous G2: N388del:Y389del.
86. The method according to Embodiment 84, wherein the APOL1 is associated with compound heterozygous G1: S342G:I384M and G2: N388del:Y389del APOL1 genetic alleles.
87. Use of citric acid cocrystal Form A of Compound I according to any one of Embodiments 64-77 in the manufacture of a medicament for treating APOL1 mediated kidney disease.
88. Citric acid cocrystal Form A of Compound I according to any one of Embodiments 64-77 for use in treating APOL1 mediated kidney disease.
89. A method of preparing citric acid cocrystal Form A of Compound I comprising:
combining Compound I Form A and citric acid in a ball mill vessel with 2-propanol/water;
shaking at 15 Hz for about 30 minutes; and
isolating citric acid cocrystal Form A of Compound I.
90. Form B of Compound I.
91. Form B of Compound I according to Embodiment 90, characterized by an X-ray powder diffractogram having a signal at one or more two-theta values selected from 11.8±0.2, 12.2±0.2, and 13.5±0.2.
92. Form B of Compound I according to Embodiment 90 or 91, characterized by an X-ray powder diffractogram having a signal at two or more two-theta values selected from 11.8±0.2, 12.2±0.2, 13.5±0.2.
93. Form B of Compound I according to any one of Embodiments 90-92, characterized by an X-ray powder diffractogram having signals at 11.8±0.2, 12.2±0.2, and 13.5±0.2 two-theta.
94. Form B of Compound I according to any one of Embodiments 90-93, characterized by an X-ray powder diffractogram having (a) a signal at the following two-theta values: 11.8±0.2, 12.2±0.2, and 13.5±0.2; and (b) a signal at one or more two-theta values selected from 11.3 0.2, 11.6±0.2, 17.0±0.2, 19.9±0.2, 22.0±0.2, 23.1±0.2, and 27.1±0.2.
95. Form B of Compound I according to any one of Embodiments 90-94, characterized by an X-ray powder diffractogram having (a) a signal at the following two-theta values: 11.8±0.2, 12.2±0.2, and 13.5±0.2; and (b) a signal at two or more two-theta values selected from 11.3 0.2, 11.6±0.2, 17.0±0.2, 19.9±0.2, 22.0±0.2, 23.1±0.2, and 27.1±0.2.
96. Form B of Compound I according to any one of Embodiments 90-95, characterized by an X-ray powder diffractogram having (a) a signal at the following two-theta values: 11.8±0.2, 12.2±0.2, and 13.5±0.2; and (b) a signal at three or more two-theta values selected from 11.3±0.2, 11.6±0.2, 17.0±0.2, 19.9±0.2, 22.0±0.2, 23.1±0.2, and 27.1±0.2.
97. Form B of Compound I according to any one of Embodiments 90-96, characterized by an X-ray powder diffractogram having signals at the following two-theta values: 11.3±0.2, 11.6 0.2, 11.8±0.2, 12.2±0.2, 13.5±0.2, 17.0±0.2, 19.9±0.2, 22.0±0.2, 23.1±0.2, and 27.1±0.2.
98. Form B of Compound I according to Embodiment 90, characterized by an X-ray powder diffractogram substantially similar to that in FIG. 10.
99. Form B of Compound I according to any one of Embodiments 90-98, characterized by a $^{13}C$ NMR spectrum having one or more signals selected from 177.0±0.2 ppm, 139.8±0.2 ppm, 131.2±0.2 ppm, 116.1±0.2 ppm, 76.4±0.2 ppm, and 20.9±0.2 ppm.
100. Form B of Compound I according to any one of Embodiments 90-99, characterized by a $^{13}C$ NMR spectrum having two or more signals selected from 177.0±0.2 ppm, 139.8±0.2 ppm, 131.2±0.2 ppm, 116.1±0.2 ppm, 76.4±0.2 ppm, and 20.9±0.2 ppm.
101. Form B of Compound I according to any one of Embodiments 90-100, characterized by a $^{13}C$ NMR spectrum having three or more signals selected from 177.0±0.2 ppm, 139.8±0.2 ppm, 131.2±0.2 ppm, 116.1±0.2 ppm, 76.4±0.2 ppm, and 20.9±0.2 ppm.
102. Form B of Compound I according to any one of Embodiments 90-101, characterized by a $^{13}C$ NMR spectrum signals at 177.0±0.2 ppm, 139.8±0.2 ppm, 131.2±0.2 ppm, 116.1±0.2 ppm, 76.4±0.2 ppm, and 20.9±0.2 ppm.
103. Form B of Compound I according to any one of Embodiments 90-102, characterized by a $^{13}C$ NMR spectrum having (a) signals at 177.0±0.2 ppm, 139.8±0.2 ppm, 131.2±0.2 ppm, 116.1±0.2 ppm, 76.4±0.2 ppm, and 20.9±0.2 ppm and (b) one or more signals selected from 172.6±0.2 ppm, 132.9±0.2 ppm, 129.2±0.2 ppm, 109.7±0.2 ppm, and 35.5±0.2 ppm.
104. Form B of Compound I according to any one of Embodiments 90-103, characterized by a $^{13}C$ NMR spectrum having (a) signals at 177.0±0.2 ppm, 139.8±0.2 ppm, 131.2±0.2 ppm, 116.1±0.2 ppm, 76.4±0.2 ppm, and 20.9±0.2 ppm and (b) two or more signals selected from 172.6±0.2 ppm, 132.9±0.2 ppm, 129.2±0.2 ppm, 109.7±0.2 ppm, and 35.5±0.2 ppm.
105. Form B of Compound I according to any one of Embodiments 90-104, characterized by a $^{13}C$ NMR spectrum having (a) signals at 177.0±0.2 ppm, 139.8±0.2 ppm, 131.2±0.2 ppm, 116.1±0.2 ppm, 76.4±0.2 ppm, and 20.9±0.2 ppm and (b) three or more signals selected from 172.6±0.2 ppm, 132.9±0.2 ppm, 129.2±0.2 ppm, 109.7±0.2 ppm, and 35.5±0.2 ppm.
106. Form B of Compound I according to any one of Embodiments 90-105, characterized by a $^{13}C$ NMR spectrum having (a) signals at 177.0±0.2 ppm, 139.8±0.2 ppm, 131.2±0.2 ppm, 116.1±0.2 ppm, 76.4±0.2 ppm, and 20.9±0.2 ppm and (b) four or more signals selected from 172.6±0.2 ppm, 132.9±0.2 ppm, 129.2±0.2 ppm, 109.7±0.2 ppm, and 35.5±0.2 ppm.
107. Form B of Compound I according to any one of Embodiments 90-106, characterized by a $^{13}C$ NMR spectrum having signals at 177.0±0.2 ppm, 172.6±0.2 ppm, 139.8±0.2 ppm, 132.9±0.2 ppm, 131.2±0.2 ppm, 129.2±0.2 ppm, 116.1±0.2 ppm, 109.7±0.2 ppm, 76.4±0.2 ppm, 35.5±0.2 ppm, and 20.9±0.2 ppm.
108. Form B of Compound I according to any one of Embodiments 90-98, characterized by a $^{13}C$ NMR spectrum substantially similar to that in FIG. 13.
109. Form B of Compound I according to any one of Embodiments 90-108, characterized by a $^{19}F$ NMR spectrum having a signal at one or more ppm values selected from −129.1±0.2 ppm, −128.4±0.2 ppm, −120.6±0.2 ppm, −115.3±0.2 ppm, and −107.9±0.2 ppm.

110. Form B of Compound I according to any one of Embodiments 90-109, characterized by a $^{19}$F NMR spectrum having a signal at two or more ppm values selected from −129.1±0.2 ppm, −128.4±0.2 ppm, −120.6±0.2 ppm, −115.3±0.2 ppm, and −107.9±0.2 ppm.

111. Form B of Compound I according to any one of Embodiments 90-110, characterized by a $^{19}$F NMR spectrum having a signal at three or more ppm values selected from −129.1±0.2 ppm, −128.4±0.2 ppm, −120.6±0.2 ppm, −115.3±0.2 ppm, and −107.9±0.2 ppm.

112. Form B of Compound I according to any one of Embodiments 90-111, characterized by a $^{19}$F NMR spectrum having a signal at four or more ppm values selected from −129.1±0.2 ppm, −128.4±0.2 ppm, −120.6±0.2 ppm, −115.3±0.2 ppm, and −107.9±0.2 ppm.

113. Form B of Compound I according to any one of Embodiments 90-112, characterized by a $^{19}$F NMR spectrum having signals at −129.1±0.2 ppm, −128.4±0.2 ppm, −120.6±0.2 ppm, −115.3±0.2 ppm, and −107.9±0.2 ppm.

114. Form B of Compound I according to any one of Embodiments 90-108, characterized by a $^{19}$F NMR spectrum substantially similar to that in FIG. 15.

115. Form B of Compound I according to any one of Embodiments 90-114, characterized by a DSC curve substantially similar to that in FIG. 11.

116. Form B of Compound I according to any one of Embodiments 90-114, characterized by a DSC curve having multiple endothermic and exothermic peaks at about 69° C., about 190° C., and/or about 195° C.

117. A pharmaceutical composition comprising Form B of Compound I according to any one of Embodiments 90-116 and a pharmaceutically acceptable carrier.

118. A method of treating APOL1 mediated kidney disease comprising administering to a patient in need thereof. Form B of Compound I according to any one of Embodiments 90-116 or a pharmaceutical composition according to Embodiment 117.

119. The method according to Embodiment 118, wherein the APOL1 mediated kidney disease is selected from ESKD, NDKD, FSGS, HIV-associated nephropathy, arterionephrosclerosis, lupus nephritis, microalbuminuria, and chronic kidney disease.

120. The method according to Embodiment 118 or 119, wherein the APOL1 mediated kidney disease is FSGS or NDKD.

121. The method according to any one of Embodiments 118-120, wherein the APOL1 mediated kidney is associated with APOL1 genetic alleles selected from homozygous G1: S342G:I384M and homozygous G2: N388del:Y389del.

122. The method according to any one of Embodiments 118-120, wherein the APOL1 mediated kidney disease is associated with compound heterozygous G1: S342G: I384M and G2: N388del:Y389del APOL1 genetic alleles.

123. A method of inhibiting APOL1 activity comprising contacting said APOL1 with Form B of Compound I according to any one of Embodiments 90-116 or a pharmaceutical composition according to Embodiment 117.

124. The method according to Embodiment 123, wherein the APOL1 is associated with APOL1 genetic alleles selected from homozygous G1: S342G:I384M and homozygous G2: N388del:Y389del.

125. The method according to Embodiment 123, wherein the APOL1 is associated with compound heterozygous G1: S342G:I384M and G2: N388del:Y389del APOL1 genetic alleles.

126. Use of Form B of Compound I according to any one of Embodiments 90-116 in the manufacture of a medicament for treating APOL1 mediated kidney disease.

127. Form B of Compound I according to any one of Embodiments 90-116 for use in treating APOL1 mediated kidney disease.

128. A method of preparing Form B of Compound I comprising:
exposing Compound I Amorphous Form to heptane vapor at ambient temperature for about 1 month; and
isolating Form B of Compound I.

129. A method of preparing Form A of Compound I comprising:
repeated distillation of Compound I in 2-methyltetrahydrofuran;
heating to 62.5° C. in a solvent comprising methanol for about 35 minutes;
cooling to 25° C.; and
isolating Form A of Compound I.

130. A method of preparing Form A of Compound I comprising:
mixing Compound I in 2-methyltetrahydrofuran and a solvent comprising methanol;
heating to 62.5° C. for about 20 minutes;
charging with heptane over about 1 hour;
adding seed crystals of Form A of Compound I;
holding at 62.5° C. for about 1 hour;
charging with heptane over about 5.5 hours;
cooling to 25° C.; and
isolating Form A of Compound I.

131. The method according to Embodiment 129 or 130, wherein the solvent comprising methanol is methanol.

132. The method according to Embodiment 129 or 130, wherein the solvent comprising methanol further comprises ethanol.

133. The method according to Embodiment 129 or 130, wherein the solvent comprising methanol further comprises propanol.

134. The method according to Embodiment 129 or 130, wherein the solvent comprising methanol further comprises 1-propanol.

135. A method of preparing Form A of Compound I comprising:
mixing Compound I in 2-methyltetrahydrofuran and a solvent comprising ethanol;
heating to 62.5° C. for about 20 minutes;
charging with heptane over about 5 minutes;
adding seed crystals of Form A of Compound I;
holding at 62.5° C. for about 1 hour;
charging with heptane over about 12 hours;
cooling to 25° C.; and
isolating Form A of Compound I.

136. The method according to Embodiment 135, wherein the solvent comprising ethanol is ethanol.

EXAMPLES

In order that the disclosure described herein may be more fully understood, the following examples are set forth. It should be understood that these examples are for illustrative purposes only and are not to be construed as limiting this disclosure in any manner.

Methods of preparation, along with the structure of and physicochemical data for Compound I, are reported in U.S. Provisional Application No. 62/780,667 filed on Dec. 17, 2018, U.S. application Ser. No. 16/717,099 filed on Dec. 17, 2019, and PCT International Application No. PCT/US2019/066746 filed on Dec. 17, 2019, the contents of each of which are incorporated herein by reference.

The compounds of the disclosure may be made according to standard chemical practices or as described herein. Throughout the following synthetic schemes and in the descriptions for preparing compounds, the following abbreviations are used:

Abbreviations

AIBN=Azobisisobutyronitrile
ARP=assay ready plate
BBBPY=4,4'-Di-tert-butyl-2,2'-dipyridyl
CBzCl=Benzyl chloroformate
CDMT=2-Chloro-4,6-dimethoxy-1,3,5-triazine
DIPEA=N,N-Diisopropylethylamine or N-ethyl-N-isopropyl-propan-2-amine
DMAP=dimethylamino pyridine
DMA=dimethyl acetamide
DME=dimethoxyethane
DMEM=Dulbecco's modified Eagle's medium
DMF=dimethylformamide
DMSO=dimethyl sulfoxide
DPPA=diphenylphosphoryl azide
EtOAc=Ethyl Acetate
EtOH=ethanol
FBS=fetal bovine serum
FLU=fluorescent values
HATU=[dimethylamino(triazolo[4,5-b]pyridin-3-yloxy)methylene]-dimethyl-ammonium (Phosphorus Hexafluoride Ion)
HDMC=N-[(5-Chloro-3-oxido-1H-benzotriazol-1-yl)-4-morpholinylmethylene]-N-methylmethanaminium hexafluorophosphate
HEPES=4-(2-hydroxyethyl)-1-piperazineethanesulfonic acid
HBSS=Hank's balanced salt solution
IPA=isopropyl alcohol
LDA=lithium diisopropyl amide
LED=light emitting diode
MeOH=methanol
MTBE=Methyl tert-butyl ether
NMM=N-methyl morpholine
NMP=N-methyl pyrrolidine
PBS=phosphate-buffered saline
$Pd(dppf)_2Cl_2$=[1,1'-Bis(diphenylphosphino)ferrocene]dichloropalladium(II)
$PdCl_2(PPh_3)_2$=Bis(triphenylphosphine)palladium(II) dichloride
PP=polypropylene
PTSA=p-Toluenesulfonic acid monohydrate
T3P=2,4,6-Tripropyl-1,3,5,2,4,6-trioxatriphosphorinane-2,4,6-trioxide
TEA=triethylamine
Tet=tetracycline
TFA=trifluoroacetic acid
THF=tetrahydrofuran
THP=tetrahydropyran
TMSS=Tris(trimethylsilyl)silane Example 1: Synthesis of Compound I 1. Preparation of Compound I Synthetic Precursors Preparation of S2

(3S,4R)-3-amino-4-hydroxy-pyrrolidin-2-one (S2)

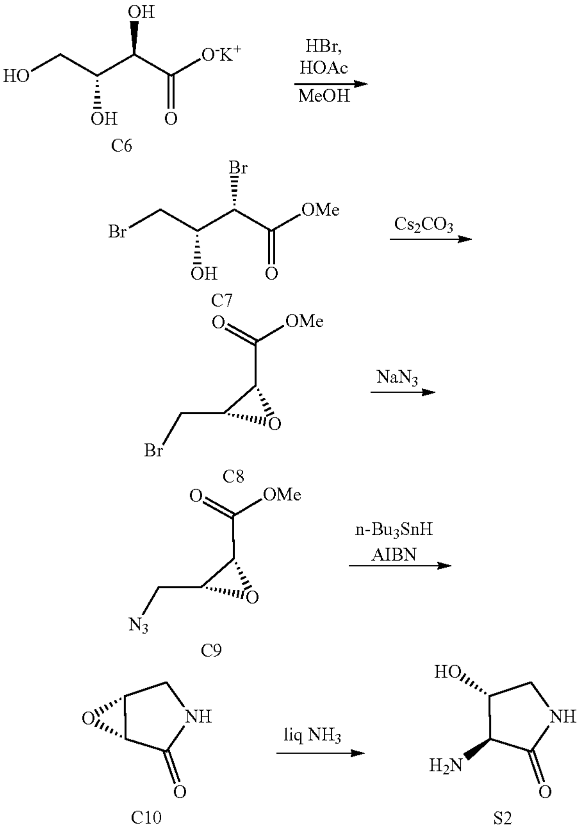

C6 C7 C8 C9 C10 S2

Step 1. Synthesis of methyl (2S,3R)-2,4-dibromo-3-hydroxy-butanoate (C7)

Potassium (2R,3R)-2,3,4-trihydroxybutanoate C6 (10 g, 57.1 mmol) was stirred with HBr in acetic acid (154 g, 103 mL of 30% w/w, 570.8 mmol) for 16 hours. Anhydrous MeOH (250 mL) was added and the mixture heated at reflux for 4 hours. The mixture was concentrated to dryness and the residue dissolved in EtOAc (100 mL). The solution was washed with water (50 mL) and brine (50 mL), then dried over $Na_2SO_4$, and concentrated in vacuo. Purification by silica gel chromatography (Gradient: 15-20% EtOAc in hexane) afforded the product as a colorless liquid (13 g, 83%). $^1H$ NMR (400 MHz, $CDCl_3$) δ 4.71 (d, J=3.4 Hz, 1H), 4.17-4.14 (m, 1H), 3.82 (s, 3H), 3.53-3.44 (m, 2H).

Step 1. Alternative procedure for synthesis of methyl (2S,3R)-2,4-dibromo-3-hydroxy-butanoate (C7)

Potassium (2R,3R)-2,3,4-trihydroxybutanoate C6 (280 g) was stirred with a 33% solution of HBr in acetic acid (1 L)

at room temperature for 24 hours. The reaction mixture was then poured into MeOH (5 L). The mixture was stirred at room temperature for 8 hours, then at 65° C. for 4 hours. The mixture was concentrated, the residue was dissolved in MeOH (1.2 L) and then concentrated sulfuric acid (30 mL) was slowly added. The mixture was heated under reflux for 6 hours, then concentrated. The residue was taken up with EtOAc (400 mL). The resulting solution was washed with water (250 mL), dried over $Na_2SO_4$, filtered, and concentrated in vacuo to give the product as an oil which solidified upon storage at 4° C. (375 g, 74%).

Step 2. Synthesis of methyl (2R,3S)-3-(bromomethyl)oxirane-2-carboxylate (C8)

Methyl (2R,3R)-2,4-dibromo-3-hydroxy-butanoate C7 (524.8 g, 1.9 mol) was dissolved in acetone (4.5 L) in a 12 L round-bottomed flask equipped with an overhead stirrer. The reaction was cooled to 0° C. in an ice-bath and $Cs_2CO_3$ (994 g, 3.1 mol) was added. The reaction was stirred for 30 minutes at 0° C. and then for 2 hours at room temperature. The mixture was filtered, washed with acetone, and then concentrated in vacuo to afford a dark grey oil residue. The product was dissolved in $CH_2Cl_2$ and filtered over a short plug of silica gel, eluting with $CH_2Cl_2$ (approx. 1 L). The filtrate was concentrated in vacuo to afford the product as a clear yellow oil (377.3 g, quantitative). $^1H$ NMR (300 MHz, $CDCl_3$) δ 3.83 (s, 3H), 3.71-3.61 (m, 2H), 3.61-3.53 (m, 1H), 3.46 (dd, J=9.9, 6.6 Hz, 1H) ppm. $^{13}C$ NMR (75 MHz, $CDCl_3$) δ 167.58, 55.89, 53.52, 52.77, 26.83 ppm.

Step 2. Alternative procedure for synthesis of methyl (2R,3S)-3-(bromomethyl)oxirane-2-carboxylate (C8)

To a solution of methyl (2R,3R)-2,4-dibromo-3-hydroxy-butanoate C7 (200 g, 0.73 mol) in acetone (2.0 L) was added anhydrous $K_2CO_3$ (151.1 g, 1.1 mol), while the reaction temperature was maintained at 0-5° C. The reaction was stirred at 0-5° C. for 2 hours, then gradually warmed to room temperature over 4 hours The reaction mixture was filtered and the filtrate was concentrated under reduced pressure. The residue was distilled under vacuum 75-80° C./200-300 Pa to give the product as a colorless liquid (105 g, 74%).

Step 3. Synthesis of methyl (2R,3R)-3-(azidomethyl)oxirane-2-carboxylate (C9)

Methyl (2R,3S)-3-(bromomethyl)oxirane-2-carboxylate C8 (52.6 g, 269.7 mmol) was dissolved in DMF (500 mL) in a 3 L round-bottomed flask equipped with a magnetic stir bar. $NaN_3$ (25.3 g, 388.4 mmol) was added and the mixture was stirred at room temperature for 1 hour. The reaction was poured into water, and extracted with EtOAc. The extract was washed with water, dried over $MgSO_4$, and concentrated in vacuo to afford a dark red oil. The oil residue was dissolved in $CH_2Cl_2$ and filtered over a plug of silica gel, eluting with $CH_2Cl_2$. The filtrate was concentrated in vacuo to afford the product as a clear, light red oil (40.8 g, 96%). $^1H$ NMR (300 MHz, $CDCl_3$) δ 3.87-3.74 (m, 3H), 3.67-3.55 (m, 2H), 3.47 (dd, J=13.3, 5.1 Hz, 1H), 3.38 (ddd, J=6.3, 5.0, 4.4 Hz, 1H). $^{13}C$ NMR (75 MHz, $CDCl_3$) δ 167.76, 54.81, 52.67, 51.32, 48.74.

Step 4. Synthesis of (1R,5R)-6-oxa-3-azabicyclo [3.1.0]hexan-2-one (C10)

A 2 L 3-neck flask with overhead stirrer was charged with methyl (2R,3R)-3-(azidomethyl)oxirane-2-carboxylate C9 (67 g, 402.5 mmol) in toluene (500 mL), stirred for 10 minutes, and then warmed to 80° C. $Bu_3SnH$ (220 mL, 817.8 mmol) and AIBN (2 g, 12.2 mmol) were dissolved in toluene (500 mL) and then added to the reaction over 3 hours using an additional funnel. The resulting reaction mixture was stirred at 80-87° C. for 1 hour, then cooled to ambient temperature, and concentrated under reduced pressure. The residue was partitioned between acetonitrile (2 L) and pentane (1 L), stirred for 10 minutes, and then the acetonitrile phase (bottom) was separated. The acetonitrile phase was washed with pentane (2×500 mL) and concentrated in vacuo to afford a light yellow solid. The solid residue was triturated with pentane (~200 mL) to afford the product as a yellow solid which was used without further purification (52 g, 98%). $^1H$ NMR (300 MHz, $CDCl_3$) δ 5.89 (s, 1H), 4.00 (q, J=2.5 Hz, 1H), 3.74-3.50 (m, 2H), 3.44 (dd, J=12.4, 2.4 Hz, 1H). $^{13}C$ NMR (75 MHz, $CDCl_3$) δ 173.24, 53.28, 52.18, 44.00.

Step 5. Synthesis of (3S,4R)-3-amino-4-hydroxy-pyrrolidin-2-one (S2)

A Parr vessel containing (1R,5R)-6-oxa-3-azabicyclo [3.1.0]hexan-2-one C10 (60 g, 605.5 mmol) and $NH_3$ (1.5 L, 58.6 mol) was pressurized to 200 psi and allowed to stir at 18° C. for 2 days. $NH_3$ was released from the vessel to provide a grey solid. Heptane was added and the mixture stirred for 30 minutes. The solid was filtered, and then the filter cake was isolated, and then EtOAc and heptane to the solid. The mixture was concentrated in vacuo to afford the product (55 g, 78%). $^1H$ NMR (300 MHz, $D_2O$) δ 4.13 (q, J=7.2 Hz, 1H), 3.53 (dd, J=10.4, 7.4 Hz, 1H), 3.36 (d, J=7.5 Hz, 1H), 3.05 (dd, J=10.4, 6.8 Hz, 1H).

Alternative Preparation of S2

(3S,4R)-3-amino-4-hydroxypyrrolidin-2-one hydrochloride (S2)

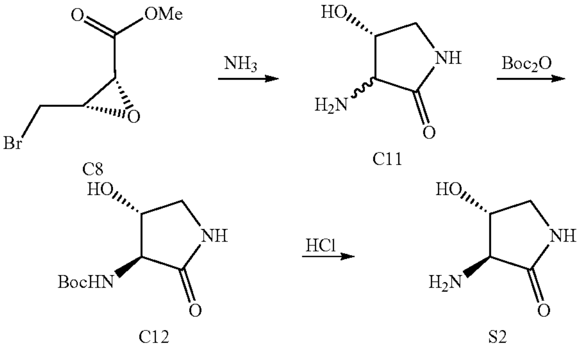

C8 C11 C12 S2

Step 1 & 2. Synthesis of N-Boc-(3S,4R)-3-amino-4-hydroxypyrrolidin-2-one (C12)

At −60° C., ammonia gas was condensed into an autoclave containing a frozen solution of methyl (2R,3S)-3-

(bromomethyl)oxirane-2-carboxylate C8 (81 g, 0.42 mol) in 1,4-dioxane (160 mL) until approx. 400 mL of liquid was collected. The autoclave was closed, allowed to warm gradually to room temperature, and then heated at 50-60° C. for 2 hours. The autoclave was then cooled back to −60° C. and depressurized. The reaction mixture was warmed gradually to allow the liquid ammonia to evaporate, leaving a viscous residue. The residue was taken up with MeOH (500 mL) and the suspension was treated with a 28% solution of sodium methoxide in MeOH (86 g, 0.42 mol). The mixture was stirred at room temperature for 30 minutes, then concentrated. The residue was dissolved in water (500 mL), then $Na_2CO_3$ (89 g, 0.84 mol) and a solution of $Boc_2O$ (110 g, 0.5 mol) in THF (200 mL) was added. The mixture was stirred at room temperature for 10 hours. The aqueous phase was then saturated with NaCl, and extracted with THE (3×200 mL). The combined organic phases were dried over $Na_2SO_4$ and concentrated in vacuo. The residue was triturated with warm MTBE (200 mL) and the precipitated solid was collected by filtration, washed with MTBE, and dried under vacuum to afford the product as a white solid (28 g, 31% yield).

Step 3. Synthesis of (3S,4R)-3-amino-4-hydroxypyrrolidin-2-one hydrochloride (S2)

To solution of N-Boc-(3S,4R)-3-amino-4-hydroxypyrrolidin-2-one C12 (28 g, 129 mmol) in EtOH (300 mL) heated at 50-60° C. was added a solution of HCl in EtOH (5.0 M, 75 mL). The reaction mixture was kept at 50-60° C. for 2 hours. The suspension was cooled to room temperature and the solid was collected by filtration, washed with EtOH and dried in vacuo to afford the product as an off-white solid (18 g, 90%). $^1H$ NMR (500 MHz, DMSO-$d_6$) δ 8.73 (brs, 3H), 8.28 (s, 1H), 6.03 (s, 1H), 4.42-4.37 (m, 1H), 3.74 (d, J=6.8 Hz, 1H), 3.48-3.39 (m, 1H), 3.03-3.00 (m, 1H).

Preparation of S12

(3-[5,7-difluoro-2-(4-fluorophenyl)-1H-indol-3-yl] propanoic acid) (S12)

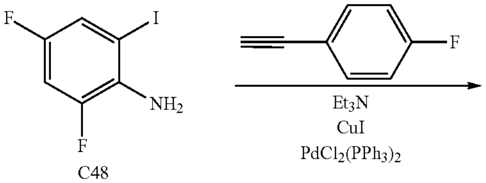

C48

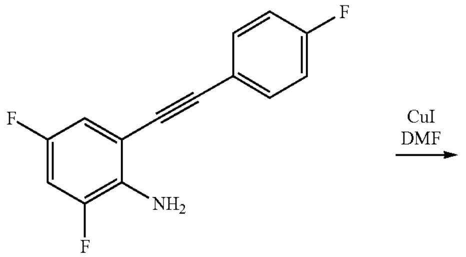

C49

-continued

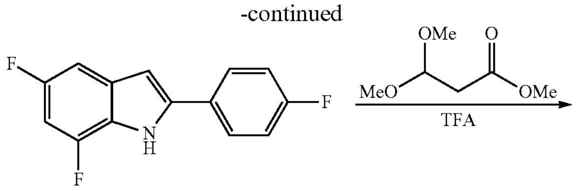

C50

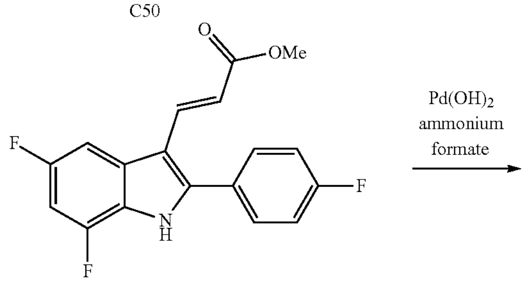

C51

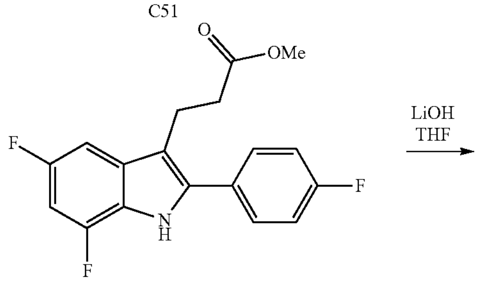

C52

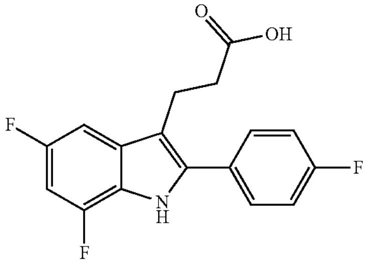

S12

Step 1. Synthesis of 2,4-difluoro-6-[2-(4-fluorophenyl)ethynyl]aniline (C49)

To a flask containing 2,4-difluoro-6-iodo-aniline C48 (134 g, 525.5 mmol) was added $NEt_3$ (1.3 L), followed by DMF (250 mL), 1-ethynyl-4-fluoro-benzene (83.5 g, 695.1 mmol), CuI (20.5 g, 107.6 mmol), and $PdCl_2(PPh_3)_2$ (25 g, 35.6 mmol). The mixture was allowed to stir at room temperature for 2 hours. Solvent was removed under reduced pressure and water (500 mL) was added. The mixture was extracted with ethyl acetate, filtered, and concentrated in vacuo. The product mixture was filtered through a silica gel plug (Eluent: $CH_2Cl_2$), followed by a second silica plug filtration (Eluent: 30-40% EtOAc in Heptane). Silica gel chromatography (Gradient: 0-20% EtOAc in heptane) afforded the product as a pale yellow solid (87 g, 60%). $^1H$ NMR (300 MHz, $CDCl_3$) δ 7.58-7.45 (m, 2H), 7.14-7.02 (m, 2H), 6.92 (ddd, J=8.8, 2.8, 1.7 Hz, 1H), 6.87-6.71 (m, 1H), 4.15 (s, 2H). LCMS m z 248.0 $[M+H]^+$.

Step 2. Synthesis of 5,7-difluoro-2-(4-fluorophenyl)-1H-indole (C50)

To a solution of 2,4-difluoro-6-[2-(4-fluorophenyl)ethynyl]aniline C49 (46 g, 167.5 mmol) in DMF (600 mL) was added CuI (1.9 g, 10.0 mmol) and the reaction was heated to reflux. Water (800 mL) was added and the mixture extracted with MTBE. The mixture was then washed with saturated NaCl solution, dried over $Na_2SO_4$, and then concentrated in vacuo to afford the product, which was used in subsequent steps without further purification (41 g, 87%). $^1H$ NMR (300 MHz, $CDCl_3$) δ 8.43 (s, 1H), 7.72-7.58 (m, 2H), 7.27-7.15 (m, 2H), 7.09 (dd, J=9.0, 2.1 Hz, 1H), 6.85-6.63 (m, 2H). LCMS m z 248.0 $[M+H]^+$.

Step 3. Synthesis of methyl (E)-3-[5,7-difluoro-2-(4-fluorophenyl)-1H-indol-3-yl]prop-2-enoate (C51)

A 12 L flask with overhead stirrer was charged with 5,7-difluoro-2-(4-fluorophenyl)-1H-indole C50 (300 g, 1.2 mol), $CH_2Cl_2$ (3 L), methyl 3,3-dimethoxypropanoate (195 mL, 1.4 mol), and TFA (300 mL, 3.9 mol). The reaction was heated to reflux for 4 hours. Additional $CH_2Cl_2$ was added to facilitate stirring. Upon cooling to room temperature, the solid product was filtered, washed with minimal $CH_2Cl_2$, and dried to afford the product (388 g, 96%). $^1H$ NMR (400 MHz, DMSO-$d_6$) δ 12.66 (s, 1H), 7.77-7.57 (m, 4H), 7.56-7.37 (m, 2H), 7.19 (ddd, J=11.0, 9.7, 2.1 Hz, 1H), 6.47 (d, J=16.1 Hz, 1H), 3.69 (s, 3H). LCMS m z 332.4 $[M+H]^+$.

Step 4. Synthesis of methyl 3-[5,7-difluoro-2-(4-fluorophenyl)-1H-indol-3-yl]propanoate (C52)

To a suspension of methyl (E)-3-[5,7-difluoro-2-(4-fluorophenyl)-1H-indol-3-yl]prop-2-enoate C51 (80 g, 236.5 mmol) in EtOH (1.5 L) under a nitrogen atmosphere was added $Pd(OH)_2$ (6 g of 20% w/w 8.5 mmol) and ammonium formate (160 g, 2.5 mol). The mixture was heated at reflux for about 3 hours, then filtered to remove catalyst. The filtrate was concentrated in vacuo to afford the product as an off-white solid, which was used in subsequent steps without further purification (82 g, 100%). $^1H$ NMR (300 MHz, $CDCl_3$) δ 8.18 (s, 1H), 7.65-7.47 (m, 2H), 7.27-7.14 (m, 2H), 7.14-7.00 (m, 1H), 6.76 (ddd, J=10.8, 9.4, 2.2 Hz, 1H), 3.65 (s, 3H), 3.27-3.04 (m, 2H), 2.75-2.49 (m, 2H). LCMS m z 334.3 $[M+H]^+$.

Step 5. Synthesis of 3-[5,7-difluoro-2-(4-fluorophenyl)-1H-indol-3-yl]propanoic acid (S12)

LiOH (67 g, 2.8 mol) was added to a solution of methyl 3-[5,7-difluoro-2-(4-fluorophenyl)-1H-indol-3-yl]propanoate C52 (217 g, 651.1 mmol) in THE (1 L) and water (100 mL). The mixture was heated at reflux for 2 hours, then allowed to cool overnight. THE was removed by concentration under reduced pressure, and water was added (approx. 1 L). The mixture was cooled on an ice bath and HCl (250 mL of 11.7 M, 2.9 mol) was added to adjust pH to about 4. EtOAc (300 mL) was added, and the aqueous layer extracted with further EtOAc (100 mL). Combined organic extracts were dried over sodium sulfate ($Na_2SO_4$) and filtered through a plug of silica gel, rinsing with EtOAc. The filtrate was concentrated in vacuo to afford an orange oil (50-75 mL). Heptanes (~50 mL) were added, and the mixture was chilled on dry ice. Upon agitation, a crystalline solid formed. The mixture was allowed to stir on an ice-bath until to allow completion of the crystallization process. The solid was filtered, washed with heptane, and air dried to afford the product (208 g, 96%). $^1H$ NMR (300 MHz, $CDCl_3$) δ 8.15 (s, 1H), 7.60-7.46 (m, 2H), 7.27-7.15 (m, 2H), 7.09 (dd, J=9.1, 2.2 Hz, 1H), 6.77 (ddd, J=10.8, 9.4, 2.2 Hz, 1H), 3.26-3.05 (m, 2H), 2.78-2.57 (m, 2H). LCMS m z 320.0 $[M+H]^+$.

Alternative Preparation of S12

Step 3. Synthesis of methyl (E)-3-[5,7-difluoro-2-(4-fluorophenyl)-1H-indol-3-yl]prop-2-enoate (C51)

A reactor was charged with 5,7-difluoro-2-(4-fluorophenyl)-1H-indole C50 (4.0 kg, 16.5 mol), $CH_2Cl_2$ (37 L), and methyl 3,3-dimethoxypropanoate (2.6 L, 18.1 mol), followed by TFA (3.9 L, 51.0 mol) at ambient temperature. The resulting mixture was heated to reflux for 6 hours. The batch was then cooled to 20° C., charged with n-heptane (2 vol), and filtered. The filter cake was dried under vacuum at 45° C. to afford the product in about 90% yield. $^1H$ NMR (300 MHz, DMSO-$d_6$) δ 12.63 (s, 1H), 7.76-7.54 (m, 4H), 7.55-7.39 (m, 2H), 7.18 (ddd, J=11.1, 9.7, 2.2 Hz, 1H), 6.46 (d, J=16.1 Hz, 1H), 3.69 (s, 3H). LCMS m z 332.1 $[M+H]^+$.

Step 4. Synthesis of methyl 3-[5,7-difluoro-2-(4-fluorophenyl)-1H-indol-3-yl]propanoate (C52)

Methyl (E)-3-[5,7-difluoro-2-(4-fluorophenyl)-1H-indol-3-yl]prop-2-enoate C51 (1.5 kg, 9.06 mol) was slurried with THE (7 L) in a vessel. $Pd(OH)_2$ (10 g of 20% w/w, about 50% water, 0.014 mol) was charged. The mixture was purged with $N_2$ three times, then once with $H_2$, and the vessel pressurized to 50 psi with $H_2$. The mixture was agitated at 20° C. until $H_2$ uptake ceased. After 1.5 hours, the mixture was purged with $N_2$ (×3) and filtered through Solka-Floc using a THE (2 vol) rinse. The resulting filtrate was concentrated in vacuo at 45° C. (to 1.5 vol), charged with cyclohexane (1 vol), and concentrated again (to 1.5 vol) at 45° C. The slurry was cooled to 15-20° C. and filtered. The filter cake was then washed with cold cyclohexane (1 vol) and dried under vacuum at 45° C. to afford the product in 95% yield.

Step 5. Synthesis of 3-[5,7-difluoro-2-(4-fluorophenyl)-1H-indol-3-yl]propanoic acid (S12)

A mixture of methyl 3-[5,7-difluoro-2-(4-fluorophenyl)-1H-indol-3-yl]propanoate C52 (9 kg, 27 mmol) in 2-MeTHF (54 L, 6 vol) and MeOH (8.1 L, 0.9 vol) was charged with 20% KOH (2 equiv, 54 mol). The mixture was stirred at 35° C. for 6 hours. The mixture was then distilled under vacuum to 27 L (3 vol) and cooled to 10-15° C. Water (7.5 L) and 2-MeTHF (16 L) were charged, and the resulting biphasic mixture was pH adjusted with 6 M HCl to a pH of about 2. The temperature was adjusted to 20° C., and the phases separated. The organic phase was washed with water (15 L), filtered through Celite® with 2-MeTHF rinse (18 L, 2 vol), and concentrated under vacuum to 18 L (2 vol). 18 L (2 vol) of n-heptane was charged and the batch again concentrated under vacuum to 18 L (3 vol). This cycle was repeated once more and the batch was seeded. 16 L (1.8 vol) n-heptane was charged and the temperature adjusted to 20° C. The slurry was stirred for 2 hours, filtered, and the cake was washed with 2×18 L (2×2 vol) n-heptane. The filter cake was dried under vacuum at 45° C. to afford the desired product in 90% yield. $^1H$ NMR (300 MHz, $CDCl_3$) δ 8.28 (s, 1H), 7.53 (ddd, J=8.7, 5.4, 2.8 Hz, 2H), 7.27-7.13 (m, 2H), 7.08 (dd, J=9.1, 2.1 Hz, 1H), 6.76 (ddd, J=11.3, 9.4, 2.2 Hz, 1H), 3.91-3.69

(m, 4H), 3.28-3.07 (m, 2H), 2.79-2.53 (m, 2H), 2.00-1.74 (m, 3H). LCMS m z 320.4 $[M+H]^+$.

2. Synthesis of Compound I

3-[5,7-difluoro-2-(4-fluorophenyl)-1H-indol-3-yl]-N-[(3S,4R)-4-hydroxy-2-oxo-pyrrolidin-3-yl]propanamide (Compound I)

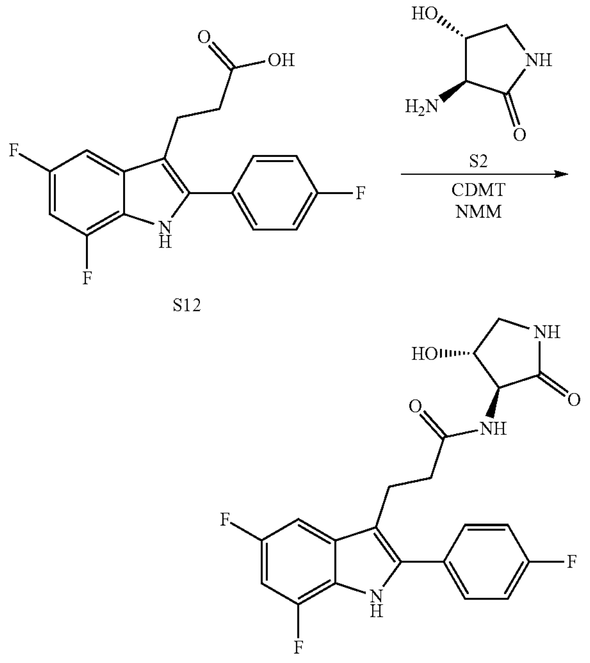

S12

Compound I

Synthesis of 3-[5,7-difluoro-2-(4-fluorophenyl)-1H-indol-3-yl]-N-[(3S,4R)-4-hydroxy-2-oxo-pyrrolidin-3-yl]propanamide (Compound I)

A 2 L 3-neck RB flask with magnetic stirrer, temperature probe and nitrogen inlet was charged with 3-[5,7-difluoro-2-(4-fluorophenyl)-1H-indol-3-yl]propanoic acid S12 (90.5 g, 283.5 mmol) and (3S,4R)-3-amino-4-hydroxy-pyrrolidin-2-one S2 (39.9 g, 343.6 mmol) in DMF (1.65 L), and stirred for 15 minutes. CDMT (61.1 g, 348 mmol) was added. The mixture was then cooled to about 2° C. on an ice bath. N-methylmorpholine was added (131 mL, 1.2 mol) drop-wise over 20 minutes and the mixture was heated at 30° C. overnight. The reaction mixture was added into about 4.5 L of ice water and extracted with EtOAc (1.2 L×4). The combined organic layers were washed with 1.2 L of 1 M HCl (×3), then water (1.2 L) and brine (1.2 L). The combined organic layers were dried over $Na_2SO_4$, filtered, and concentrated. The mixture was washed through a silica gel plug (1.8 L of silica gel), first eluting with 25% EtOAc in dichloromethane (8 L) to remove impurities, followed by hot EtOAc (8 L) to elute the product. The EtOAc filtrate was concentrated in vacuo. TBME was then added (400 mL), and the mixture allowed to stir overnight. Filtration of the resulting solid afforded the product as a white solid (62 g, 52%). $^1H$ NMR (300 MHz, $CD_3OD$) δ 7.70-7.58 (m, 2H), 7.29-7.13 (m, 3H), 6.73 (ddd, J=11.1, 9.6, 2.2 Hz, 1H), 4.34 (td, J=7.6, 6.8 Hz, 1H), 4.21 (d, J=7.8 Hz, 1H), 3.56 (dd, J=9.9, 7.6 Hz, 1H), 3.20-3.04 (m, 3H), 2.65-2.53 (m, 2H). LCMS m z 418.2 $[M+H]^+$. Optical rotation: $[\alpha]_D^{20.7}=-14.01$ (c=1.0, 10 mg in 1 mL of MeOH).

Alternative Procedure for Synthesis of Compound I

Step 1. Synthesis of methyl (E)-3-[5,7-difluoro-2-(4-fluorophenyl)-1H-indol-3-yl]prop-2-enoate (C51)

A solution of 5,7-difluoro-2-(4-fluorophenyl)-1H-indole C50 (100 g, 1.0 equiv) in dichloromethane (850 mL, 8.5 vol) was agitated at 22° C. Methyl 3,3-dimethoxypropionate (63 mL, 1.1 equiv) was charged followed by trifluoroacetic acid (96 mL, 3.1 equiv), which was rinsed forward with dichloromethane (25 mL, 0.25 vol). The batch was heated to 38° C. and stirred at that temperature. After 4 hours, the batch was cooled to 22° C. and charged with n-heptane (200 mL, 2 vol). The mixture was stirred for at least 1 hour at 22° C. The slurry was filtered, and the reactor and the filter cake were washed with n-heptane (1×2 vol (200 mL) and 1×3 vol (300 mL)). The resulting solid was dried under vacuum with nitrogen bleed at 45° C. to afford the product C51 (127.7 g, 95% yield).

Step 2. Synthesis of methyl 3-[5,7-difluoro-2-(4-fluorophenyl)-1H-indol-3-yl]propanoate (C52)

To a hydrogenator was charged methyl (E)-3-[5,7-difluoro-2-(4-fluorophenyl)-1H-indol-3-yl]prop-2-enoate C51 (100.4 g, 1.0 equiv) followed by $Pd(OH)_2/C$ (0.014 equiv). The vessel was sealed and three vacuum/purge cycles with $N_2$ were performed. 2-MeTHF (2000 mL, 20 vol) was charged using residual vacuum and the resulting mixture was stirred at 22° C. The vessel was sealed and three vacuum/purge cycles with $N_2$ were performed, followed by one vacuum purge cycle with hydrogen ($H_2$). The temperature was adjusted to 22° C., and the vessel pressurized with 20 psi $H_2$. The mixture was agitated at 22° C. for 4 hours. Three vacuum/purge cycles with nitrogen (N2) were performed. The batch was filtered through a pad of Hyflo®, and the filter cake was rinsed with 2-MeTHF (2×300 mL, 2×3 vol). The combined filtrates were placed under vacuum and distilled at ≤45.0° C. to 2.0 to 3.0 total volumes. The batch temperature was adjusted to 22° C., and the vessel was charge with n-heptane (1000 mL, 10 vol) over at least 1 hour. A vacuum was applied and the filtrate distilled at ≤45.0° C. to 3.5 to 4.5 total volumes. The slurry was cooled to 22° C. and allowed to stir for at least than 1 hour. The slurry was filtered and the filter cake was washed with n-heptane (1×1 vol (100 mL) and 1×0.5 vol (50 mL)). The solids were dried under vacuum with nitrogen bleed at 45° C. to afford the product C52 (91.9 g, 91% yield).

Step 3. Synthesis of 3-[5,7-difluoro-2-(4-fluorophenyl)-1H-indol-3-yl]propanoic acid (S12)

A mixture of methyl 3-[5,7-difluoro-2-(4-fluorophenyl)-1H-indol-3-yl]propanoate C52 (80.0 g, 1.0 equiv) and 2-MeTHF (480 mL, 6 vol) was agitated at 22° C. and treated with methanol (72 mL, 0.9 vol). A solution of KOH (27.1 g, 2.0 equiv) in water (107 mL, 1.3 vol) was charged over approximately 20 minutes. The resulting mixture was heated to an internal temperature of 35° C. and stirred for 3 hours. The temperature was adjusted to 22° C. A vacuum was applied and the mixture was distilled at ≤45° C. to 3.0 total volumes. The internal temperature was adjusted to 12° C.

The mixture was then charged with water (64 mL, 0.8 vol) and 2-MeTHF (304 mL, 3.8 vol). 6N HCl (75 mL, 0.9 vol) was slowly charged into the mixture with vigorous agitation until the batch attained a pH<3. The internal temperature was adjusted to 22° C., and the biphasic mixture was stirred for at least 0.5 hours. The stirring was stopped, and the phases were allowed to separate for no less than 0.5 hours. The lower aqueous phase was removed. Water (160 mL, 2 vol) was charged to the reactor at 22° C., and the biphasic mixture stirred for at least 0.5 hours. The stirring was stopped, and the phases allowed to separate over at least 0.5 hours. The lower aqueous phase was removed, and the batch was filtered through a pad of Hyflo®. The reactor and filter cake were rinsed with 2-MeTHF (160 mL, 2 vol). A vacuum was applied and the combined filtrates distilled at ≤40.0° C. to 2-3 total volumes. The vessel was charged with n-heptane (160 mL, 2 vol), a vacuum was applied, and the filtrate was distilled at ≤40.0° C. to 2 total volumes, a step repeated one additional time. The mixture was then charged with additional n-heptane (144 mL, 1.8 vol). The internal temperature was adjusted to 40° C. and the mixture stirred for at least 2 hours. The internal temperature was adjusted to 22° C. over a minimum of 5 hours and the mixture stirred for no less than 16 hours. The slurry was filtered. The filter cake was washed with n-heptane (3×40 mL, 3×0.5 vol). The solids were dried under vacuum with nitrogen bleed at 45° C. to afford product S12 (72.6 g, 95% yield).

Step 4. Synthesis of 3-[5,7-difluoro-2-(4-fluorophenyl)-1H-indol-3-yl]-N-[(3S,4R)-4-hydroxy-2-oxo-pyrrolidin-3-yl]propanamide (Compound I)

A mixture of S12 (50.0 g, 1.0 equiv), (3S,4R)-3-amino-4-hydroxypyrrolidin-2-one hydrochloride S2 (25.1 g, 1.05 equiv), and CDMT (30.3 g, 1.1 equiv) in DMF (250 mL, 5 vol) was agitated and cooled to 0° C. The reactor was charged with NMM (60 mL, 3.5 equiv) over no less than 1 hour, while maintaining the internal temperature at ≤5° C. The batch was stirred at about 5° C. for no less than 1 hour. The batch was warmed to 22° C. over at least 1 hour and stirred at 22° C. for 16 hours. The batch was cooled to 0° C. Water (250 mL, 5 vol) was charged, while keeping the internal temperature <20° C. The mixture was charged with a 90/10 mixture of EtOAc/IPA (1000 mL, 20 vol). 6N HCl (40 mL, 0.8 vol) was then charged, while maintaining an internal temperature <10° C., until a pH of about 1-3 was achieved. The internal temperature was adjusted to 22° C. and the biphasic mixture stirred for no less than 0.5 hours. Stirring was stopped and the phases allowed to separate for no less than 0.5 hours. The lower aqueous phase was removed. The aqueous layer was back extracted with a 90/10 mixture of EtOAc/IPA (2×250 mL, 2×5 vol) at 22° C. The combined organic phases from extractions were washed with water (5×500 mL, 5×10 vol) at 22° C., by mixing for no less than 0.5 hours and settling for no less than 0.5 hours for each wash. The batch was polish filtered. A vacuum was applied and the organic phase distilled at <50° C. to 9.5-10.5 total volumes. The mixture was charged with EtOAc (500 mL, 10 vol), vacuum was applied, and the organic phase distilled at <50° C. to 9.5-10.5 total volumes, a step repeated one more time. The mixture was charged with EtOAc (300 mL, 6 vol) and n-heptane (200 mL, 4 vol). The resulting slurry was heated to 50° C. and stirred for no less than 17 hours. The mixture was then cooled to 22° C. over 2 hours, and stirred for no less than 1 hour. The slurry was filtered. The filter cake was washed with 1:1 EtOAc/n-heptane (2×150 mL, 2×3 vol). The solids were dried under vacuum with nitrogen bleed at ≤45° C. to afford Compound I (52.6 g, 80% yield).

Re-Crystallization of Compound I

Compound I (37.6 g, 1.0 equiv) was charged to a reactor followed by a 3:1 mixture of IPA/water (240 mL, 6.4 vol). The slurry was heated to an internal temperature of 75° C. The batch was cooled to an internal temperature of 55° C. and stirred at that temperature for at least 0.5 hours. The batch was seeded with 0.5 wt % of a previously generated batch of Compound I, as a suspension in a mixture of 3:1 IPA/water (4 mL, 0.1 vol). The mixture was stirred at 55° C. for no less than 1.5 hours. Water (218 mL, 5.8 vol) was added over minimum period of 5 hours, while maintaining the temperature at 55° C. The slurry was cooled to 22° C. over no less than 5 hours and stirred for no less than 2 hours. The slurry was filtered. The filter cake was washed with 2:3 IPA/water (2×114 mL, 2×3 vol). The solids were dried under vacuum with nitrogen bleed at ≤45° C. to afford Compound I (34.5 g, 92% yield).

Form A of Compound I 12.3 kg of Compound I was charged to the reactor, followed by a 3:1 mixture of 2-propanol/water. Agitation was initiated, and the mixture was heated to 75° C. to achieve complete dissolution. The mixture was cooled to 55° C. over 1 hour and agitated at that temperature for 30 minutes. Agitation was continued for 1.5 hours. Water (5.8 vol) was charged over 5 hours at 55° C., after which the mixture was cooled to 22° C. over 6 hours. The mixture was agitated at 22° C. for 2 hours, then filtered under vacuum. The resulting wet cake was washed with a 3:1 mixture of 2-propanol/water (2.74 vol×2) and pulled dry under vacuum. The wet cake was further dried under vacuum with nitrogen bleed at 45° C. to yield 11.2 kg of Form A.

Hydrate Form A of Compound I 200 mg of Compound I was charged with 10 mL of water. The slurry was cooled to 5° C. and allowed to stir. Hydrate A was observed after 3 days of stirring.

Hydrate Form B of Compound I 1 g of Compound I was charged with 50 mL of water. The slurry was cooled to 5° C. and allowed to stir. Hydrate B was observed after 18 hours of stirring.

Hydrate Form C of Compound I

A solution of Compound I in MeOH was sealed into a system with water vapor, allowing the vapor to interact with the solution. The precipitate was isolated and analyzed to be Hydrate Form C.

Hydrate Form D of Compound I

A suspension of Compound I Form A was magnetically stirred at 50° C. for 2 to 5 days in EtOH before the solid was isolated and analyzed. The resulting solid was Hydrate Form D.

Hydrate Form E of Compound I

A clear solution of Compound I in MeOH was covered using parafilm with 3 to 4 pinholes and kept at room temperature, allowing the solvent to evaporate slowly. The resulting form was Hydrate Form E.

Hydrate Form F of Compound I

A saturated solution of Compound I in ACN was cooled from 50° C. to 5° C. at a rate of 0.1° C./min. The precipitate was equilibrated at 5° C. before isolation and analysis. The resulting solid was Hydrate Form F.

MTBE Solvate of Compound I

MTBE was added into a clear solution of Compound I in MeOH. The precipitate was stirred at room temperature/5° C. before isolation and analysis. The resulting solid was the MTBE solvate.

DMF Solvate of Compound I

Water was added into a clear solution of Compound I in DMF. The precipitate was stirred at room temperature/5° C. before isolation and analysis. The resulting solid was the DMF solvate.

Amorphous Form of Compound I

The amorphous form of Compound I was made by spray drying a solution of Compound I at about 7% solid load in 95:5 w/w acetone:water.

Example 2: Compound I Form A—Synthetic Procedure without Seeding

A 40 mL solution of Compound I (5 g) in 2-methyltetrahydrofuran was charged in a 100 mL round bottom flask. The solution was distilled to 15 mL under 150 mbar vacuum at 50° C. The following distillation process was then repeated three times: 40 mL of 2-methyltetrahydrofuran was charged to the flask, then the resulting solution was distilled to 15 mL under 150 mbar vacuum at 50° C.

The distilled solution was transferred to a 100 mL reactor with overhead stirrer. 30 mL 2-methyltetrahydrofuran was used to rinse the flask and transferred to the reactor. 5 mL methanol was charged into the reactor. The solution was heated to 62.5° C. Then 10 mL heptane was charged over 30 minutes. The batch was held at 62.5° C. for 35 minutes. Then 40 mL heptane was charged over 4 hours. Solids crystallized out during the heptane charge. The slurry was cooled to 25° C. over 4 hours and held at 25° C. for 12 hours. The resulting solids were collected by vacuum filtration. The wet cake was transferred to a vacuum oven at 45° C. with a slight nitrogen bleed for 24 hours to yield 3.09 g of Compound I Form A.

Example 3: Compound I Form A—Synthetic Procedure with Seeding 5 g of Compound I was charged with 45 mL 2-methyltetrahydrofuran and 5 mL methanol in a 100 mL reactor with overhead stirrer. The slurry was heated to 62.5° C. and held for 20 minutes. Then 15 mL heptane was charged over 1 hour. The batch was then seeded with 25 mg of Compound I Form A and held at 62.5° C. for 1 hour. Then 35 mL heptane was charged over 5.5 hours. The slurry was cooled to 25° C. for over 8 hours and held at 25° C. for 35 hours. The resulting solids were collected by vacuum filtration. The wet cake was transferred to a vacuum oven at 45° C. with a slight nitrogen bleed for 52 hours to yield 4.37 g of product. The solid obtained was Compound I Form A.

Example 4: Compound I Form A—Alternative Synthetic Procedure with Seeding 5 g of Compound I was charged with 40 mL 2-methyltetrahydrofuran and 10 mL ethanol in a 100 mL reactor with overhead stirrer. The slurry was heated to 62.5° C. and held at this temperature for 20 minutes. Then 5 mL heptane was charged over 5 minutes. Then the batch was seeded with 60 mg of Compound I Form A and held at 62.5° C. for 1 hour. Then 20 mL heptane was charged over 8 hours. Then 25 mL heptane was charged over 4 hours. The slurry was cooled to 25° C. for over 4 hours and held at 25° C. for 4 hours. The resulting solids were collected by vacuum filtration. The wet cake was transferred to a vacuum oven at 45° C. with a slight nitrogen bleed for 27.3 hours to yield 3.67 g of Compound I Form A.

Example 5: Solid Forms of Compound I

Solid State NMR Experimental—Applies to all Solid Forms of Compound I Disclosed Herein A Bruker-Biospin 400 MHz wide-bore spectrometer equipped with Bruker-Biospin 4 mm HFX probe was used. Samples were packed into 4 mm $ZrO_2$ rotors and spun under Magic Angle Spinning (MAS) condition with spinning speed typically set to 12.5 kHz. The proton relaxation time was measured using $^1$H MAS $T_1$ saturation recovery relaxation experiment in order to set up proper recycle delay of the $^{13}$C cross-polarization (CP) MAS experiment. The fluorine relaxation time was measured using $^{19}$F MAS $T_1$ saturation recovery relaxation experiment in order to set up proper recycle delay of the $^{19}$F MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

1. Compound I Ethanol Solvate Form A

A. Synthetic Procedure 100 mg of Compound I Form A was added to 1 mL of anhydrous ethanol to make a slurry at ambient temperature. The slurry was then cooled to 5° C. and stirred for 2 weeks. The wet cake isolated was Compound I Ethanol Solvate Form A.

B. X-Ray Powder Diffraction

The powder, X-ray powder diffraction (XRPD), diffractogram of Compound I Ethanol Solvate Form A was acquired at room temperature in reflection mode using a Bruker Advance equipped with Vantec-1 detector. Sample was analyzed on a silicon sample holder from 3-40° 2-theta on continuous mode with step size of 0.0144531° and time per step of 0.25 seconds. Sample was spinning at 15 rpm. The XRPD diffractogram for Compound I Ethanol Solvate Form A is provided in FIG. 1 and the data is summarized below in Table 1.

TABLE 1

| Peak list from XRPD diffractogram of Compound I Ethanol Solvate Form A | | |
|---|---|---|
| XRPD Peaks. | Angle (Degrees 2-Theta ±0.2) | Intensity % |
| 1 | 14.7 | 100.0 |
| 2 | 24.8 | 87.9 |
| 3 | 18.1 | 54.9 |
| 4 | 24.4 | 49.9 |
| 5 | 14.8 | 47.2 |
| 6 | 23.5 | 33.3 |
| 7 | 7.7 | 32.1 |
| 8 | 21.5 | 31.6 |
| 9 | 14.4 | 30.0 |
| 10 | 7.3 | 20.2 |
| 11 | 22.0 | 17.3 |
| 12 | 25.9 | 17.0 |
| 13 | 13.7 | 14.5 |
| 14 | 23.9 | 14.2 |
| 15 | 27.5 | 12.2 |
| 16 | 22.2 | 12.1 |
| 17 | 19.2 | 12.1 |
| 18 | 29.1 | 11.2 |
| 19 | 30.5 | 10.7 |
| 20 | 26.3 | 10.6 |
| 21 | 20.5 | 10.6 |
| 22 | 16.8 | 10.5 |

C. Solid-State NMR

The $^{13}C$ CPMAS of Compound I Ethanol Solvate Form A (FIG. 2) was acquired at 275K with 10 kHz spinning and using adamantane as a reference. The peaks are listed in Table 2 below.

TABLE 2

| Peak list from $^{13}C$ CPMAS of Compound I Ethanol Solvate Form A | | |
|---|---|---|
| Peak # | Chem Shift [ppm] | Intensity [rel] |
| 1 | 179.4 | 31.8 |
| 2 | 176.2 | 36.1 |
| 3 | 174.3 | 32.0 |
| 4 | 171.9 | 28.5 |
| 5 | 162.8 | 10.6 |
| 6 | 160.7 | 18.3 |
| 7 | 157.4 | 12.8 |
| 8 | 155.1 | 18.1 |
| 9 | 149.6 | 16.8 |
| 10 | 147.1 | 25.0 |
| 11 | 135.4 | 39.0 |
| 12 | 132.6 | 30.4 |
| 13 | 131.2 | 63.7 |
| 14 | 128.0 | 100.0 |
| 15 | 126.4 | 50.2 |
| 16 | 120.6 | 47.3 |
| 17 | 116.7 | 65.5 |
| 18 | 112.4 | 48.8 |
| 19 | 109.1 | 45.9 |
| 20 | 99.1 | 35.9 |
| 21 | 96.7 | 25.4 |
| 22 | 76.0 | 25.7 |
| 23 | 73.0 | 42.3 |
| 24 | 60.9 | 26.5 |
| 25 | 58.0 | 84.9 |
| 26 | 57.5 | 99.1 |
| 27 | 44.7 | 37.5 |
| 28 | 37.7 | 41.9 |
| 29 | 37.0 | 45.4 |
| 30 | 25.0 | 31.1 |
| 31 | 22.6 | 39.2 |
| 32 | 18.9 | 53.1 |
| 33 | 18.0 | 80.4 |

The $^{19}F$ MAS of Compound I Ethanol Solvate Form A (FIG. 3) was acquired at 275K with 10 kHz spinning and using adamantane as a reference. The peaks are listed in Table 3 below.

TABLE 3

| Peak list from $^{19}F$ MAS of Compound I Ethanol Solvate Form A | | |
|---|---|---|
| Peak # | Chem Shift [ppm] | Intensity [rel] |
| 1 | −111.5 | 8.0 |
| 2 | −113.0 | 3.0 |
| 3 | −122.9 | 12.5 |
| 4 | −126.0 | 12.4 |
| 5 | −131.2 | 10.9 |
| 6 | −136.0 | 9.2 |

2. Compound I Ethanol Solvate Form B

A. Synthetic Procedure 100 mg of Compound I Form A was added to 1 mL of anhydrous ethanol to make a slurry at ambient temperature. The slurry was then cooled to 5° C. and stirred for 2 weeks. The wet cake was isolated and vacuum dried at 45° C. overnight. The dried solid was Compound I Ethanol Solvate Form B.

B. X-Ray Powder Diffraction

The powder, X-ray powder diffraction (XRPD), diffractogram of Compound I Ethanol Solvate Form B was acquired at room temperature in reflection mode using a Bruker Advance equipped with Vantec-1 detector. The sample was analyzed on a silicon sample holder from 3-40° 2-theta on continuous mode with a step size of 0.0144531° and time per step of 0.25 seconds. The sample was spinning at 15 rpm. The XRPD diffractogram for Compound I Ethanol Solvate Form B is provided in FIG. 4 and the data is summarized below in Table 4.

TABLE 4

| Peak list from XRPD diffractogram of Compound I Ethanol Solvate Form B | | |
|---|---|---|
| XRPD Peaks | Angle (Degrees 2-Theta ±0.2) | Intensity % |
| 1 | 15.3 | 100.0 |
| 2 | 15.6 | 95.2 |
| 3 | 15.1 | 65.2 |
| 4 | 7.6 | 58.3 |
| 5 | 24.0 | 47.4 |
| 6 | 4.9 | 46.4 |
| 7 | 8.3 | 45.6 |
| 8 | 16.8 | 39.4 |
| 9 | 8.1 | 33.0 |
| 10 | 9.9 | 30.0 |
| 11 | 9.8 | 27.0 |
| 12 | 20.2 | 25.4 |
| 13 | 17.0 | 23.3 |
| 14 | 18.1 | 21.8 |
| 15 | 19.5 | 21.6 |
| 16 | 19.2 | 20.0 |
| 17 | 26.0 | 19.3 |
| 18 | 18.9 | 18.7 |
| 19 | 27.0 | 18.0 |
| 20 | 11.4 | 17.6 |
| 21 | 13.7 | 16.8 |
| 22 | 23.2 | 14.5 |

TABLE 4-continued

| Peak list from XRPD diffractogram of Compound I Ethanol Solvate Form B | | |
|---|---|---|
| XRPD Peaks | Angle (Degrees 2-Theta ±0.2) | Intensity % |
| 23 | 24.5 | 14.2 |
| 24 | 22.8 | 13.1 |
| 25 | 4.1 | 10.0 |

C. Thermogravimetric Analysis

Thermal gravimetric analysis of Compound I Ethanol Solvate Form B was measured using the TA TGA Q5000 from TA Instruments. The sample was scanned from 25° C. to 350° C. with a heating rate of 10° C. per minute under a nitrogen purge.

The TGA thermogram (FIG. 5) showed multiple weight loss events from ambient temperature to 135° C. to a total of about 3% of initial weight.

D. Differential Scanning Calorimetry Analysis

Differential scanning calorimetry analysis of Compound I Ethanol Solvate Form B was measured using the TA Q2000 DSC from TA Instruments. The sample was placed in an aluminum pan, along with an empty aluminum reference pan in a calorimeter cell. The calorimeter cell was closed and scanned from 25° C. to 360° C. with a heating rate of 10° C. per minute under a nitrogen flow.

The thermogram (FIG. 6) showed multiple endothermic and exothermic peaks around 78° C., 128° C., 148° C., and 197° C.

3. Compound I Citric Acid Cocrystal Form A

A. Synthetic Procedure 100 mg of Compound I Form A and 50 mg citric acid was added with 20 μL of solvent mixture (84 w % 2-propanol with 16 w % water) into a steel ball mill vessel. The ball mill was shaken at 15 Hz for 30 minutes. The solid analyzed was Compound I citric acid cocrystal Form A.

B. X-Ray Powder Diffraction

The powder, X-ray powder diffraction (XRPD), diffractogram of Compound I citric acid cocrystal Form A was acquired at room temperature in reflection mode using a Bruker Advance equipped with Vantec-1 detector. The sample was analyzed on a silicon sample holder from 3-40° 2-theta on continuous mode with step size of 0.0144531° and time per step of 0.25 seconds. Sample was spinning at 15 rpm.

The XRPD diffractogram for Compound I citric acid cocrystal Form A is provided in FIG. 7 and the data is summarized below in Table 5.

TABLE 5

| Peak list from XRPD diffractogram of Compound I Citric Acid Cocrystal Form A | | |
|---|---|---|
| XRPD Peaks | Angle (Degrees 2-Theta ±0.2) | Intensity % |
| 1 | 18.8 | 100.0 |
| 2 | 21.9 | 91.8 |
| 3 | 23.5 | 82.0 |
| 4 | 4.7 | 55.7 |
| 5 | 18.1 | 50.6 |
| 6 | 21.5 | 34.2 |
| 7 | 27.0 | 19.9 |

TABLE 5-continued

| Peak list from XRPD diffractogram of Compound I Citric Acid Cocrystal Form A | | |
|---|---|---|
| XRPD Peaks | Angle (Degrees 2-Theta ±0.2) | Intensity % |
| 8 | 22.5 | 19.1 |
| 9 | 17.7 | 17.7 |
| 10 | 20.4 | 15.6 |
| 11 | 25.2 | 13.7 |
| 12 | 29.0 | 13.6 |

C. Thermogravimetric Analysis

Thermal gravimetric analysis of Compound I citric acid cocrystal Form A was measured using the TA TGA Q5000 from TA Instruments. The sample was scanned from 25° C. to 350° C. with a heating rate of 10° C. per minute under a nitrogen purge.

The TGA thermogram (FIG. 8) showed a gradual weight loss from ambient temperature until thermal degradation.

D. Differential Scanning Calorimetry Analysis

Differential scanning calorimetry analysis of Compound I citric acid cocrystal Form A was measured using the TA Q2000 DSC from TA Instruments. The sample was placed in an aluminum pan, along with an empty aluminum reference pan in a calorimeter cell. The calorimeter cell was closed and scanned from 25° C. to 360° C. with a heating rate of 10° C. per minute under a nitrogen flow.

The thermogram (FIG. 9) showed an endothermic peak around 185° C.

4. Compound I Form B

A. Synthetic Procedure 50 mg of Compound I Amorphous Form was placed in a petri dish and exposed to the heptane vapor at ambient temperature about one month. The solid obtained was Compound I Form B.

B. X-Ray Powder Diffraction

The powder, X-ray powder diffraction (XRPD), diffractogram of Compound I Form B was acquired at room temperature in reflection mode using a Bruker Advance equipped with Vantec-1 detector. Sample was analyzed on a silicon sample holder from 3-40° 2-theta on continuous mode with step size of 0.0144531° and time per step of 0.25 seconds. Sample was spinning at 15 rpm. The XRPD diffractogram for Compound I Form B is provided in FIG. 10 and the data is summarized below in Table 6.

TABLE 6

| Peak list from XRPD diffractogram of Compound I Form B | | |
|---|---|---|
| XRPD Peaks | Angle (Degrees 2-Theta ±0.2) | Intensity % |
| 1 | 19.9 | 100.0 |
| 2 | 23.1 | 63.5 |
| 3 | 11.3 | 44.9 |
| 4 | 22.0 | 40.3 |
| 5 | 27.1 | 35.5 |
| 6 | 11.6 | 33.8 |
| 7 | 17.0 | 31.2 |
| 8 | 14.3 | 28.2 |
| 9 | 24.4 | 27.2 |
| 10 | 12.8 | 24.6 |
| 11 | 11.8 | 24.6 |
| 12 | 28.7 | 22.9 |
| 13 | 16.2 | 20.4 |
| 14 | 13.5 | 18.7 |

TABLE 6-continued

| Peak list from XRPD diffractogram of Compound I Form B | | |
|---|---|---|
| XRPD Peaks | Angle (Degrees 2-Theta ±0.2) | Intensity % |
| 15 | 5.6 | 18.4 |
| 16 | 12.2 | 17.4 |
| 17 | 15.1 | 13.0 |
| 18 | 18.3 | 11.4 |

C. Differential Scanning Calorimetry Analysis

Differential scanning calorimetry analysis of Compound I Form B was measured using the TA Q2000 DSC from TA Instruments. The sample was placed in an aluminum pan, then along with an empty aluminum reference pan in a calorimeter cell. The calorimeter cell was closed and scanned from 25° C. to 300° C. with a heating rate of 2° C. per minute under a nitrogen flow.

The thermogram (FIG. 11) showed multiple endothermic and exothermic peaks around 69° C., 190° C., and 195° C.

5. Mixtures of Compound I Form A and Compound I Form B

A. Synthetic Procedure

Compound I was slurried in heptane for about 5 days at 5° C., and the resulting solid was isolated. The solid obtained was a mixture of Compound I Form A and Compound I Form B (about 64% Form A with about 36% Form B).

B. Solid State NMR (SSNMR)

Figure 12:
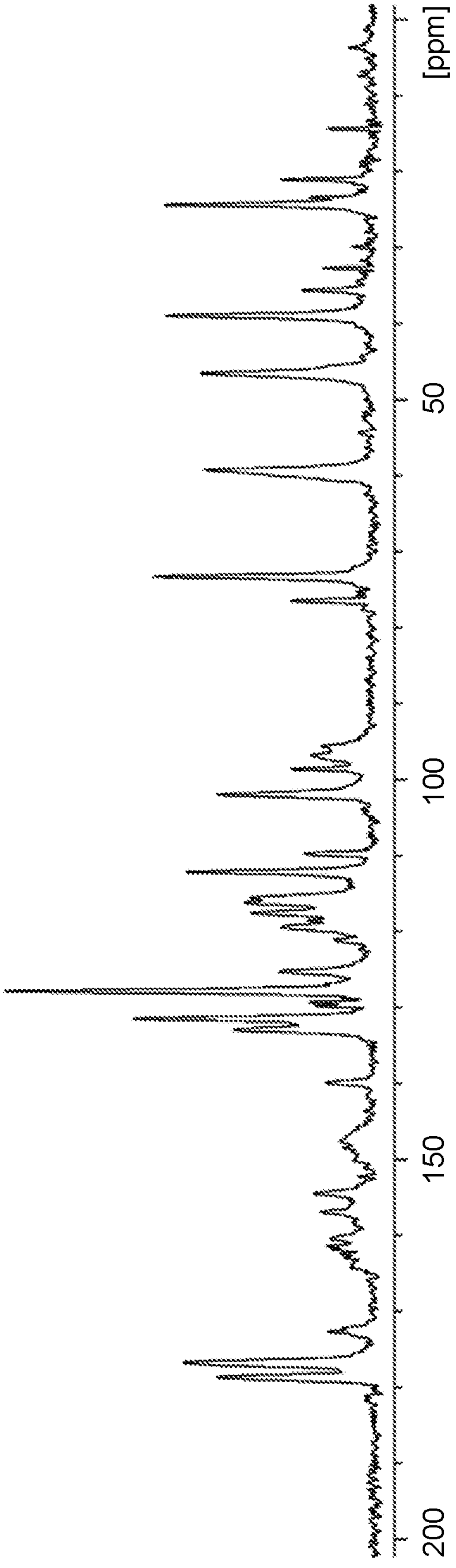
FIG. 12 depicts a solid state $^{13}C$ NMR spectrum of a mixture of Form A of Compound I and Form B of Compound I.

The $^{13}C$ CPMAS on Compound I (about 64% Form A with about 36% Form B) (FIG. 12) was acquired at 275K with 12.5 kHz spinning and using adamantane as a reference. The peaks are listed below in Table 7.

TABLE 7

| Peak list from $^{13}C$ CPMAS of Compound I (Mixture of Form A and Form B) | | |
|---|---|---|
| Peak # | Chem Shift [ppm] | Intensity [rel] |
| 1 | 178.5 | 42.51 |
| 2 | 176.6 | 51.58 |
| 3 | 172.6 | 12.5 |
| 4 | 163.8 | 6.07 |
| 5 | 162.8 | 7.94 |
| 6 | 162.3 | 8.91 |
| 7 | 161.8 | 11.1 |
| 8 | 161.3 | 12.91 |
| 9 | 160.3 | 11.72 |
| 10 | 156.8 | 14.38 |
| 11 | 154.3 | 16.15 |
| 12 | 148.4 | 8.23 |
| 13 | 147.5 | 9.07 |
| 14 | 139.8 | 12.78 |
| 15 | 132.9 | 38.05 |
| 16 | 131.4 | 65.14 |
| 17 | 129.7 | 15.96 |
| 18 | 129.2 | 17.4 |
| 19 | 127.7 | 100 |
| 20 | 125.2 | 25.53 |
| 21 | 121.0 | 10.5 |
| 22 | 119.3 | 24.82 |
| 23 | 118.4 | 17.68 |
| 24 | 117.5 | 33.39 |
| 25 | 116.1 | 35.2 |
| 26 | 115.5 | 33.31 |
| 27 | 112.1 | 50.85 |
| 28 | 109.7 | 18.71 |
| 29 | 101.9 | 42.65 |
| 30 | 98.5 | 22.26 |

TABLE 7-continued

| Peak list from $^{13}C$ CPMAS of Compound I (Mixture of Form A and Form B) | | |
|---|---|---|
| Peak # | Chem Shift [ppm] | Intensity [rel] |
| 31 | 96.7 | 16.92 |
| 32 | 95.5 | 14.06 |
| 33 | 76.4 | 22.25 |
| 34 | 73.2 | 59.32 |
| 35 | 59.1 | 45.45 |
| 36 | 46.4 | 46.68 |
| 37 | 38.8 | 56.54 |
| 38 | 35.5 | 19.36 |
| 39 | 32.6 | 13.76 |
| 40 | 29.8 | 5.56 |
| 41 | 24.2 | 56.48 |
| 42 | 23.3 | 17.3 |
| 43 | 22.3 | 4.13 |
| 44 | 20.9 | 25.11 |
| 45 | 14.2 | 12.39 |

The $^{13}C$ CPMAS on Compound I Form B (FIG. 13) was acquired at 275K with 12.5 kHz spinning and using adamantane as a reference, based on mathematical subtraction of Form A from the mixture of about 6400 Form A with about 36% Form B. The peaks are listed below in Table 8.

TABLE 8

| Peak list from $^{13}C$ CPMAS of Compound I (Form B) | | |
|---|---|---|
| Peak # | Chem Shift [ppm] | Intensity [rel] |
| 1 | 177.0 | 38.57 |
| 2 | 172.6 | 41.56 |
| 3 | 164.3 | 11.88 |
| 4 | 161.3 | 27.63 |
| 5 | 139.8 | 42.99 |
| 6 | 132.9 | 40.16 |
| 7 | 132.0 | 31.83 |
| 8 | 131.2 | 100 |
| 9 | 129.7 | 49.78 |
| 10 | 129.2 | 52.21 |
| 11 | 127.7 | 27.25 |
| 12 | 126.7 | 21.25 |
| 13 | 125.3 | 20.89 |
| 14 | 121.0 | 27.68 |
| 15 | 118.4 | 29.29 |
| 16 | 116.1 | 82.63 |
| 17 | 109.7 | 61.68 |
| 18 | 98.5 | 65.19 |
| 19 | 95.5 | 32.17 |
| 20 | 76.4 | 74.54 |
| 21 | 60.0 | 47.59 |
| 22 | 59.0 | 21.43 |
| 23 | 47.2 | 21.09 |
| 24 | 46.3 | 27.13 |
| 25 | 45.5 | 27.35 |
| 26 | 35.5 | 62.43 |
| 27 | 20.9 | 83.51 |

Figure 14:
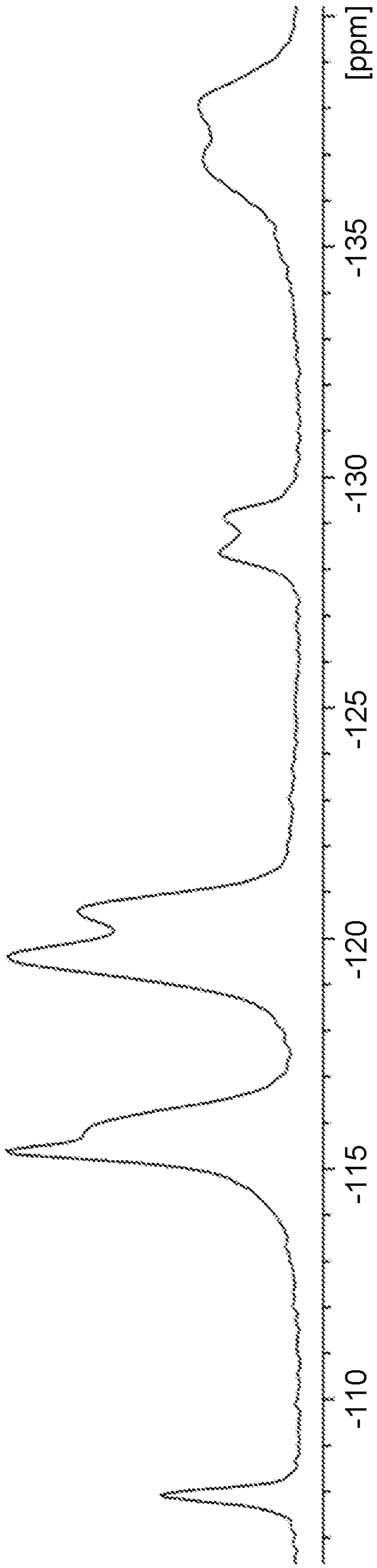
FIG. 14 depicts a solid state $^{19}F$ NMR spectrum of a mixture of Form A of Compound I and Form B of Compound I.

The $^{19}F$ MAS of Compound I (about 64% Form A mixed with about 36% Form B) (FIG. 14) was acquired at 275K with 12.5 kHz spinning and using adamantane as a reference. The peaks are listed below in Table 9.

TABLE 9

| Peak list from $^{19}$F MAS of Compound I (Mixture of Form A and Form B) | | |
|---|---|---|
| Peak # | Chem Shift [ppm] | Intensity [rel] |
| 1 | −107.9 | 5.9 |
| 2 | −115.4 | 12.5 |
| 3 | −115.8 | 9.13 |
| 4 | −119.6 | 12.42 |
| 5 | −120.6 | 9.44 |
| 6 | −128.4 | 3.4 |
| 7 | −129.1 | 3.21 |
| 8 | −136.9 | 4.1 |
| 9 | −138.1 | 4.31 |

The $^{19}$F MAS of Compound I Form B (FIG. 15), as determined based on mathematical subtraction of the spectra of Form A from the spectra of a solid form mixture comprising about 64% Form A and about 36% Form B, was acquired at 275K with 12.5 kHz spinning and using adamantane as a reference. The peaks are listed below in Table 10.

TABLE 10

| Peak list from $^{19}$F MAS of Compound I (Form B) | | |
|---|---|---|
| Peak # | Chem Shift [ppm] | Intensity [rel] |
| 1 | −107.9 | 9.03 |
| 2 | −115.3 | 10.87 |
| 3 | −120.6 | 12.5 |
| 4 | −128.4 | 5.2 |
| 5 | −129.1 | 4.89 |

Other Embodiments

This disclosure provides merely non-limiting exemplary embodiments of the disclosure. One skilled in the art will readily recognize from the disclosure and claims that various changes, modifications, and variations can be made therein without departing from the spirit and scope of the disclosure as defined in the following claims.

What is claimed is:

1. A solid form of Compound I:

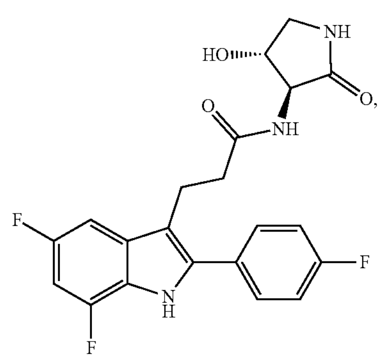

(I)

wherein the solid form is selected from:

(a) Ethanol solvate Form A;

(b) Ethanol solvate Form B;

(c) Citric acid cocrystal Form A; and (d) Form B.

2. The solid form of Compound I according to claim 1, wherein the solid form is Ethanol solvate Form A, characterized by an X-ray powder diffractogram having a signal at 14.4±0.2 and/or 21.5±0.2 two-theta.

3. The solid form of Compound I according to claim 1, wherein the solid form is Ethanol solvate Form A, characterized by an X-ray powder diffractogram having (a) a signal at 14.4±0.2 and/or 21.5±0.2 two-theta; and (b) a signal at 23.5±0.2 and/or 24.8±0.2 two-theta.

4. The solid form of Compound I according to claim 1, wherein the solid form is Ethanol solvate Form A, characterized by an X-ray powder diffractogram substantially similar to that in FIG. 1.

5. The solid form of Compound I according to claim 1, wherein the solid form is Ethanol solvate Form A, characterized by a $^{13}$C NMR spectrum having one or more signals selected from 18.0±0.2 ppm, 57.5±0.2 ppm, 58.0±0.2 ppm, 116.7±0.2 ppm, and 128.0±0.2 ppm.

6. The solid form of Compound I according to claim 1, wherein the solid form is Ethanol solvate Form A, characterized by a $^{19}$F NMR spectrum having a signal at one or more ppm values selected from −136.0±0.2 ppm, −131.2±0.2 ppm, −126.0±0.2 ppm, −122.9±0.2 ppm, −113.0±0.2 ppm, and −111.5±0.2 ppm.

7. The solid form of Compound I according to claim 1, wherein the solid form is Ethanol solvate Form B, characterized by an X-ray powder diffractogram having a signal at 11.4±0.2 and/or 15.3±0.2 two-theta.

8. The solid form of Compound I according to claim 1, wherein the solid form is Ethanol solvate Form B, characterized by an X-ray powder diffractogram having (a) a signal at 11.4±0.2 and/or 15.3±0.2 two-theta; and (b) a signal at 19.5±0.2 two-theta.

9. The solid form of Compound I according to claim 1, wherein the solid form is Ethanol solvate Form B, characterized by an X-ray powder diffractogram substantially similar to that in FIG. 4.

10. The solid form of Compound I according to claim 1, wherein the solid form is Citric acid cocrystal Form A, characterized by an X-ray powder diffractogram having a signal at one or more two-theta values selected from 4.7±0.2, 18.8±0.2, 21.9±0.2, and 23.5±0.2.

11. The solid form of Compound I according to claim 1, wherein the solid form is Citric acid cocrystal Form A, characterized by an X-ray powder diffractogram having a signal at two or more two-theta values selected from 4.7±0.2, 18.8±0.2, 21.9±0.2, and 23.5±0.2.

12. The solid form of Compound I according to claim 1, wherein the solid form is Citric acid cocrystal Form A, characterized by an X-ray powder diffractogram substantially similar to that in FIG. 7.

13. The solid form of Compound I according to claim 1, wherein the solid form is Form B, characterized by an X-ray powder diffractogram having a signal at two or more two-theta values selected from 11.8±0.2, 12.2±0.2, and 13.5±0.2.

14. The solid form of Compound I according to claim 1, wherein the solid form is Form B, characterized by an X-ray powder diffractogram substantially similar to that in FIG. 10.

15. The solid form of Compound I according to claim 1, wherein the solid form is Form B, characterized by a $^{19}$F NMR spectrum having a signal at three or more ppm values selected from −129.1±0.2 ppm, −128.4±0.2 ppm, −120.6±0.2 ppm, −115.3±0.2 ppm, and −107.9±0.2 ppm.

16. The solid form of Compound I according to claim 1, wherein the solid form is Form B, characterized by a $^{19}$F NMR spectrum having signals at −129.1±0.2 ppm, −128.4±0.2 ppm, −120.6±0.2 ppm, −115.3±0.2 ppm, and −107.9±0.2 ppm.

17. The solid form of Compound I according to claim 1, wherein the solid form is Form B, characterized by a $^{19}F$ NMR spectrum substantially similar to that in FIG. 15.

18. A pharmaceutical composition comprising the solid form of Compound I according to claim 1 and a pharmaceutically acceptable carrier.

19. A method of treating APOL1 mediated kidney disease comprising administering to a patient in need thereof the solid form of Compound I according to claim 1.

20. The method according to claim 19, wherein the APOL1 mediated kidney disease is selected from ESKD, NDKD, FSGS, HIV-associated nephropathy, arterionephrosclerosis, lupus nephritis, microalbuminuria, and chronic kidney disease.

21. The method according to claim 19, wherein the APOL1 mediated kidney disease is associated with APOL1 genetic alleles selected from homozygous G1: S342G:I384M and homozygous G2: N388del:Y389del.

22. The method according to claim 19, wherein the APOL1 mediated kidney disease is associated with compound heterozygous G1: S342G:I384M and G2: N388del:Y389del APOL1 genetic alleles.

23. A method of inhibiting APOL1 activity comprising contacting said APOL1 with the solid form of Compound I according to claim 1.

24. A method of preparing ethanol solvate Form A of Compound I:

(I)

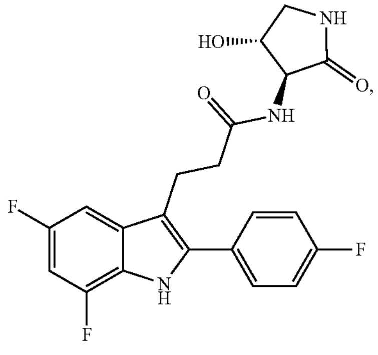

comprising:

mixing Compound I Form A with anhydrous ethanol;

cooling to 5° C. and stirring for about 2 weeks; and isolating ethanol solvate Form A of Compound I.

25. A method of preparing ethanol solvate Form B of Compound I:

(I)

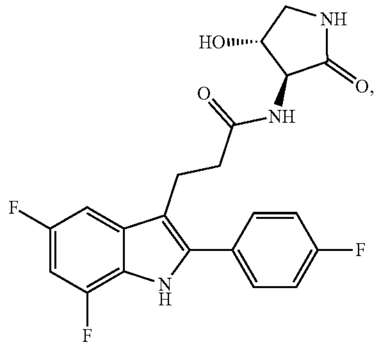

comprising:

mixing Compound I Form A with anhydrous ethanol;

cooling to 5° C. and stirring for about 2 weeks;

isolating a wet cake;

drying under vacuum at 45° C.; and isolating ethanol solvate Form B of Compound I.

26. A method of preparing citric acid cocrystal Form A of Compound I:

(I)

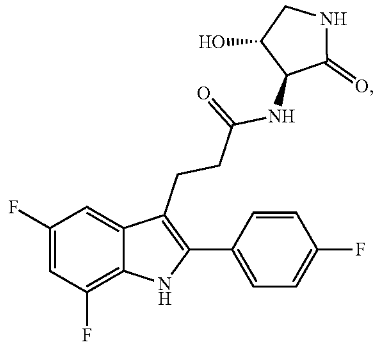

comprising:

combining Compound I Form A and citric acid in a ball mill vessel with propanol/water;

shaking at 15 Hz for about 30 minutes; and isolating citric acid cocrystal Form A of Compound I.

27. A method of preparing Form A of Compound I:

(I)

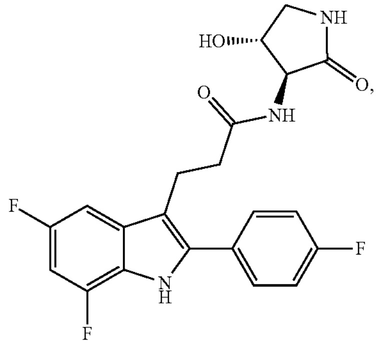

selected from:

(a) a method comprising:

repeated distillation of Compound I in 2-methyltetrahydrofuran;

heating to 62.5° C. in a solvent comprising methanol for about 35 minutes;

cooling to 25° C.; and isolating Form A of Compound I;

(b) a method comprising:

mixing Compound I in 2-methyltetrahydrofuran and a solvent comprising methanol;

heating to 62.5° C. for about 20 minutes;

charging with heptane over about 1 hour;

adding seed crystals of Form A of Compound I;

holding at 62.5° C. for about 1 hour;

charging with heptane over about 5.5 hours;

cooling to 25° C.; and isolating Form A of Compound I; or (c) a method comprising:

mixing Compound I in 2-methyltetrahydrofuran and a solvent comprising ethanol;

heating to 62.5° C. for about 20 minutes;

charging with heptane over about 5 minutes;

adding seed crystals of Form A of Compound I;

holding at 62.5° C. for about 1 hour;

charging with heptane over about 12 hours;

cooling to 25° C.; and isolating Form A of Compound I.

28. A method of preparing Form B of Compound I:

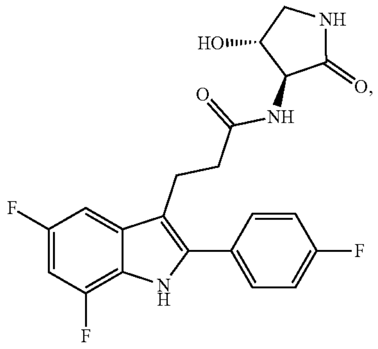

(I)

comprising:

exposing Compound I Amorphous Form to heptane vapor at ambient temperature for about 1 month; and isolating Form B of Compound I.

* * * * *